US012590071B2

(12) United States Patent
Pae et al.

(10) Patent No.: US 12,590,071 B2
(45) Date of Patent: Mar. 31, 2026

(54) HYDRAZONE DERIVATIVE IN WHICH TERMINAL AMINE GROUP IS SUBSTITUTED WITH ARYL GROUP OR HETEROARYL GROUP, AND USE THEREOF

(71) Applicant: KOREA INSTITUTE OF SCIENCE AND TECHNOLOGY, Seoul (KR)

(72) Inventors: Ae Nim Pae, Seoul (KR); Yun Kyung Kim, Seoul (KR); Sang Min Lim, Seoul (KR); Sungsu Lim, Seoul (KR); Jihye Seong, Seoul (KR); Jae Wook Lee, Seoul (KR); Ji Yeon Song, Seoul (KR); Seulgi Shin, Seoul (KR); Hyean Jeong Jeong, Seoul (KR); Woo Seung Son, Seoul (KR); Haeun Lee, Seoul (KR); Da Mi Lim, Seoul (KR); Seok Kyu Kim, Seoul (KR); Jee Yun Ahn, Seoul (KR); Chae Won Kim, Seoul (KR); Ashwini Machhindra Londhe, Seoul (KR); Lizaveta Gotina, Seoul (KR); Hyojin Kim, Seoul (KR); Hye Yeon Lee, Seoul (KR); Nam Gyung Kim, Seoul (KR); Eunji Cha, Seoul (KR); Kunhee Kim, Seoul (KR); Ji Woong Lim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 1250 days.

(21) Appl. No.: 17/415,382

(22) PCT Filed: Dec. 26, 2018

(86) PCT No.: PCT/KR2018/016679
§ 371 (c)(1),
(2) Date: Jan. 24, 2022

(87) PCT Pub. No.: WO2020/130214
PCT Pub. Date: Jun. 25, 2020

(65) Prior Publication Data

US 2022/0396553 A1 Dec. 15, 2022

(30) Foreign Application Priority Data

Dec. 19, 2018 (KR) ........................ 10-2018-0165400

(51) Int. Cl.
*C07D 241/42* (2006.01)
*C07C 255/66* (2006.01)
(Continued)

(52) U.S. Cl.
CPC .......... *C07D 241/42* (2013.01); *C07C 255/66* (2013.01); *C07D 209/14* (2013.01);
(Continued)

(58) Field of Classification Search
CPC .. C07D 241/42; C07D 209/14; C07D 215/38; C07D 231/12; C07D 231/56;
(Continued)

(56) References Cited

U.S. PATENT DOCUMENTS

| | | | |
|---|---|---|---|
| 9,962,384 | B1 | 5/2018 | Kim et al. |
| 2006/0276433 | A1 | 12/2006 | Kawagoe et al. |
| 2015/0202186 | A1 | 7/2015 | Durón et al. |

FOREIGN PATENT DOCUMENTS

| | | | |
|---|---|---|---|
| GB | 2228004 | A | 8/1990 |
| JP | 07206800 | A | 8/1995 |

(Continued)

OTHER PUBLICATIONS

Pluta R et al. Tau Protein-Targeted Therapies in Alzheimer's Disease: Current State and Future Perspectives. In: Huang X, editor. Alzheimer's Disease: Drug Discovery [Internet]. Brisbane (AU): Exon Publications; Dec. 18, 2020. Chapter 4. Available from: https://www.ncbi.nlm.nih.gov/books/NBK566118/ (Year: 2020).*
Ting, H. P., David F. Wilson, and Britton Chance. "Effects of uncouplers of oxidative phosphorylation on the specific conductance of bimolecular lipid membranes." Archives of Biochemistry and Biophysics 141, No. 1 (1970): 141-146.) (Year: 1970).*
National Center for Biotechnology Information. PubChem Compound Summary for CID 14930586, 1,3-Benzothiazol-2-ylcarbonohydrazonoyl dicyanide. https://pubchem.ncbi.nlm.nih.gov/compound/1_3-Benzothiazol-2-ylcarbonohydrazonoyl-dicyanide. Created Feb. 9, 2007. (Year: 2007).*
Alexander L. Kolb, et al., J. Am. Soc. Nephrol., 29, 2018, 1154-1164.

(Continued)

*Primary Examiner* — James H Alstrum-Acevedo
*Assistant Examiner* — Carolyn L. Ladd
(74) *Attorney, Agent, or Firm* — CANTOR COLBURN LLP

(57) ABSTRACT

A compound represented by Formula 3 as described herein, or a pharmaceutically acceptable salt thereof, and a method of making a Formula 3 compound.

In Formula 3: $R_1$ is hydrogen; and

Cy is unsubstituted benzothiazol-6-yl, benzothiazol-5-yl, quinolin-3-yl, indolyl, pyrrolopyridinyl, oxodihydrobenzothiazolyl, or oxodihydrobenzoxazolyl; or substituted benzothiazol-6-yl, benzothiazol-5-yl, indazolyl, quinolin-3-yl, indolyl, pyrrolopyridinyl, oxodihydrobenzothiazolyl, oxodihydrobenzoxazolyl, or oxodihydrobenzoimidazolyl, each of which is substituted with: (i) methyl, ethyl, propyl, butyl, isopropyl, isobutyl, methoxy, ethoxy, fluoro, chloro, bromo, trifluoroethyl, difluoromethyl, trifluoromethoxy, dimethylcarbamoyl, phenoxy, isopropoxy, methylamino or dimethylamino; or (ii) phenyl, pyridinyl, furanyl, or thiophenyl unsubstituted or substituted with at least one of methyl, fluoro, and dimethylamino.

A compound of Formula 4 as described herein, or a pharmaceutically salt thereof.

14 Claims, No Drawings

(51) Int. Cl.

| | |
|---|---|
| ***C07D 209/14*** | (2006.01) |
| ***C07D 215/38*** | (2006.01) |
| ***C07D 231/12*** | (2006.01) |
| ***C07D 231/56*** | (2006.01) |
| ***C07D 237/14*** | (2006.01) |
| ***C07D 239/26*** | (2006.01) |
| ***C07D 239/30*** | (2006.01) |
| ***C07D 239/34*** | (2006.01) |
| ***C07D 277/28*** | (2006.01) |
| ***C07D 277/82*** | (2006.01) |
| ***C07D 417/04*** | (2006.01) |
| ***C07D 417/12*** | (2006.01) |
| ***C07D 471/04*** | (2006.01) |
| ***C07D 487/04*** | (2006.01) |

(52) U.S. Cl.

CPC ......... *C07D 215/38* (2013.01); *C07D 231/12* (2013.01); *C07D 231/56* (2013.01); *C07D 237/14* (2013.01); *C07D 239/26* (2013.01); *C07D 239/30* (2013.01); *C07D 239/34* (2013.01); *C07D 277/28* (2013.01); *C07D 277/82* (2013.01); *C07D 417/04* (2013.01); *C07D 417/12* (2013.01); *C07D 471/04* (2013.01); *C07D 487/04* (2013.01)

(58) Field of Classification Search

CPC .. C07D 237/14; C07D 239/26; C07D 239/30; C07D 239/34; C07D 277/28; C07D 277/82; C07D 417/04; C07D 417/12; C07D 471/04; C07D 487/04; C07C 255/66

See application file for complete search history.

(56) References Cited

FOREIGN PATENT DOCUMENTS

| | | | |
|---|---|---|---|
| JP | H07206800 | A | 8/1995 |
| JP | 2006514043 | A | 4/2006 |
| JP | 2008511602 | A | 4/2008 |
| JP | 2008513364 | A | 5/2008 |
| KR | 100628407 | B1 | 9/2006 |
| KR | 1020080070848 | A | 7/2008 |
| KR | 1020180050130 | A | 5/2018 |
| WO | 9959597 | A1 | 11/1999 |
| WO | 0177080 | A2 | 10/2001 |
| WO | 03045379 | A1 | 6/2003 |
| WO | 2012080729 | A2 | 6/2012 |
| WO | 2019216589 | A1 | 11/2019 |

OTHER PUBLICATIONS

Levijoki, J. et al., "Further evidence for the cardiac troponin C mediated calcium sensitization by levosimendan: structure-response and binding analysis with analogs of levosimendan", Journal of Molecular Cell Cardiology, 2000, 32, 479-491.
S. Torii, et al., Cell Death Discovery (2015) 1, 15015, 12 pp.
STN°] Database Registry[Online](CAS Registry No. 155387-78-3,May 27, 1994.
STN°] Database Registry[Online](CAS Registry No. 302936-41-0,Nov. 15, 2000.
STN°] Database Registry[Online](CAS Registry No. 501662-84-6,Apr. 4, 2003.
STN°] Database Registry[Online](CAS Registry No. 663922-38-1,Mar. 17, 2004.
Tsai, P. C. et al., "Synthesis and solvatochromic properties of 3,6-bishetarylazodyes derived from pyrazolo[1,5-a] pyrimidine", Dyes and Pigments, 2008, 76, 575-581.
A. M. Kamal El-Dean, et. al., "Synthesis of Phrazolotriazines via Cyclization of Hydrazones", Afinidad LV, 1998, 476, p. 295-298.
Abdel Hafez, Ali A., et al. New Heterocyclo-Substituted Pyrazolo[3, 4,-b] Pyridine Derivatives (1993): 1198-1202.
AU Office Action issued in 2018453188 by the CIPO dated Oct. 28, 2022, 10 pp.
AU Office Action issued in 2018453188 by the CIPO dated Dec. 22, 2022, 9 pp.
CAS Registry Number: 2322621-06-5 and CAS Registry No. 2059491-82-4, Dec. 2022, 1 pg.
CAS Registry No. 453583-11-4, 2022, 1 pg.
Etify Abdel-Ghafar Bakhite, Synthesis of New Pyrazolo[3,4-b]quinolines, Thieno[2,3-b]quinolines and Related Condensed Heterocyclic Systems, Journal of the Chinese Chemical Society, 2001, 48, 1175-1183.
Kamal El-Dean, A. M., et al., Synthesis of some fusedpyrazolo[3,4-b] pyridine heterocyclic compounds, Indian Journal of Chemistry (1991), pp. 878-882.
Salem, et. al., Novel Pyrazolo[3,4-b]pyridine Derivatives: Synthesis, Characterization, Antimicrobial and Antiproliferative Profile, Bio. Pharm. Bull., 2016, v39, p. 473-483.
Bo Liu, et al., Synthesis of Some New Biological Active Hydrazono Derivatives of 2-Aminobenzothiazoles, Journal of Chinese Pharmaceutical Sciences, 1993, 2 (2), 5 pp.
Extended European Search Report issued in EP 18944116 dated Sep. 1, 2022, 10 pp.
RN 366802-69-9 Registry, May 27, 1994, 1 page.
RN 503183-54-8 Registry, Apr. 16, 2003, 1 page.
RN 503183-55-9 Registry, Apr. 16, 2003, 1 page.
Office Action issued in JP 2021-536264, dated Aug. 16, 2022, 6 pp.
Liu Bo, et al, Synthesis of Some New Benzothiazolylazopyrazoles and Benzothiazolyl-pyrimidines, 1994, vol. 14, p. 151-155.
Bloom, G. "The Trigger and Bullet in Alzheimer Disease Pathogenesis", JAMA Neurology, 2014, vol. 71(4), p. 505-508.
Kaiser et al. "Self-Organizing Maps for Identification of New Inhibitors of P-Glycoprotein", J. Med. Chem. 2007, 50, 1698-1702.
Office Action issued in AU 2018453188, dated Jan. 10, 2022, 12 pp.
A M Kamai El-Dean et al., "Synthesis of some fused pyrazolo[3, 4-b]pyridine heerocyclic compounds," Indian Journal of Chemistry, Sep. 1991, pp. 878-882, vol. 30B.
A.M. Kamal El-Dean et al., "Synthesis of Pyrazolotriazines via Cyclization of Hydrazones," Assiut University, Afinidad LV, 1998, pp. 295-298, vol. 476.
Ali A. Abdel Hafez et al., "New Heterocyclo-Substituted Pyrazolo[3,4-b]pyridine Derivatives," Collect. Czech. Chem. Commun., 1993, pp. 1198-1202, vol. 58.
English Description (RN 137017-19-7), Excerpt from the Office Action issued by the Russian Patent Office dated Sep. 28, 2022 of Russian Patent No. 2021118119/04.
Etify Abdel-Ghafar Bakhite, "Syn the sis of New Pyrazolo[3,4-b]quinolines, Thieno[2,3-b]quinolines and Related Con densed Heterocyclic Sys tems," Jour nal of the Chinese Chem i cal So ci ety, 2001, pp. 1175-1183, vol. 48.
Jan Lasovsky et al., "Chemiluminescence enhanced by intramicellar energy transfer," Journal of Luminescence, 1995, pp. 25-32, vol. 65.
Jan Slouka, "Acta Universitatispalackianne olomucensis facultas rerum naturalium chemica XXVIII," Acta Upol, Fac. Rer. Nat., 1989, pp. 175-181, vol. 94.
Office Action issued by the Russian Patent Office dated Sep. 28, 2022 of Russian Patent No. 2021118119/04.
Rafat M. Mohareb et al., "Synthesis and cytotoxicity evaluation of thiazole derivatives obtained from 2-amino-4,5,6,7-tetrahydrobenzo[b]thiophene- 3-carbonitrile," Acta Pharm., Original research paper, Oct. 30, 2017, pp. 495-510, vol. 67.

* cited by examiner

HYDRAZONE DERIVATIVE IN WHICH TERMINAL AMINE GROUP IS SUBSTITUTED WITH ARYL GROUP OR HETEROARYL GROUP, AND USE THEREOF

CROSS-REFERENCE TO RELATED APPLICATIONS

This application is a national stage application of PCT/KR2018/016679, filed Dec. 26, 2018, which claims priority to and the benefit of KR 10-2018-0165400 filed on Dec. 19, 2018, both of which are hereby incorporated by reference in their entirety.

TECHNICAL FIELD

The present invention relates to novel hydrazone derivatives in which a terminal amine group is substituted with an aryl group or a heteroaryl group, and uses thereof.

BACKGROUND

Tau protein (tau (T) protein), which is a microtubule-associated protein (MAP) mainly expressed in axons of nerve cells with a molecular weight of 50,000 to 70,000, serves to stabilize microtubules, and represents molecular diversity through phosphorylation. In humans, tau protein is formed into six isoforms by the insertion of 29 or 58 amino acid residues at the N-terminus and the alternative splicing of mRNA of 3 or 4 repeating structures (referred to as microtubule binding domain) at the C-terminus.

In healthy nerves, tau protein stabilizes microtubules by promoting growth from axons and nerve cell polarization. When pathological hyperphosphorylation occurs, tau protein separates from microtubules, resulting in insoluble aggregation. Further, a structural skeleton inducing the aggregation of tau protein has been proposed, and evidence has been provided that insoluble filaments are formed from 10 soluble monomers, and that these filaments are bound into high-dimensional structures called neurofibrillary tangles (NFTs). Human full-length tau protein comprises a microtubule binding domain consisting of four repetitive conserved sequences. Among these repetitive sequences, positively charged residues have an important function in binding to highly negatively charged microtubules (20 to 30 electrons per αβ-tubulin dimer). The binding affinity to tau microtubules is also actively regulated by the phosphorylation of tau protein, and this phosphorylation causes dynamic rearrangement of microtubule networks. When tau protein is phosphorylated abnormally excessively, the balance of this dynamic rearrangement is disrupted, and the affinity to microtubules is rapidly decreased.

The hyperphosphorylation and/or aggregation of tau proteins cause abnormal accumulation of these tau proteins in nerve cells, which is pointed to as a cause of various neurodegenerative diseases and the like. Tau protein aggregates are mainly found in the cell bodies and dendrites of nerve cells, and these tau protein aggregates are called neurofibrillary tangles (NFTs) and neuropil threads. Examination of the microstructures of neurofibrillary tangles (NFTs) reveals that such microstructures thereof consist of paired helical filaments (PHFs) in which tau proteins are entangled like fine threads and are aggregated and hyperphosphorylated, unlike normal tau protein. An abnormal tau protein aggregation phenomenon appears also in tauopathy. In this case, although it is not known exactly what role the aggregation of tau protein plays in the progress of tauopathy, this tau protein aggregation phenomenon appears similar to an aggregation phenomenon that is common in general neurodegenerative diseases.

As such, although it is known that hyperphosphorylation and/or aggregation of tau protein causes various neurodegenerative diseases comprising Alzheimer's disease and tauopathy, the specific mechanism how these abnormal tau species cause changes in the signaling pathway and elicit neurotoxicity has not yet been verified, and there are no effective treatment methods or therapeutic agents yet available to treat these diseases.

DISCLOSURE

Technical Problem

The present inventors have made many efforts to discover novel small-molecule compounds capable of inhibiting the aggregation and/or hyperphosphorylation of tau protein. As a result, they found that a series of hydrazone derivatives in which the terminal amine group is substituted with an aryl group or a heteroaryl group effectively inhibits the aggregation of tau protein, and does not exhibit cytotoxicity at effective concentrations. Based on this finding, the present invention was completed.

Technical Solution

A first aspect of the present invention is to provide a compound represented by Formula 1 below or a pharmaceutically acceptable salt thereof:

Formula 1

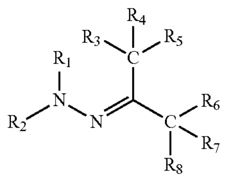

in Formula 1 above, $R_1$ is hydrogen or $C_{1-6}$ alkyl;

$R_2$ is unsubstituted or substituted $C_{6-14}$ aryl, 5- to 14-membered heteroaryl, or 5- to 14-membered heterocyclyl;

$R_3$ to $R_5$ are i) all hydrogen, ii) form a triple bond together with one N, iii) $R_3$ and $R_4$ form a double bond together with NH, O, or S to form imine, oxo, or thioxo, respectively, and $R_5$ is $C_{1-6}$ alkoxy, amino, $C_{1-6}$ alkylamino, di($C_{1-6}$ alkyl)amino, or 5- to 14-membered heterocyclyl, or iv) $R_3$ to $R_5$ are connected to a heteroatom O, N, or S by a single or double bond, and comprise carbon and the heteroatom connected thereto to form unsubstituted or substituted 5- to 14-membered heteroaryl or heterocyclyl; and $R_6$ to $R_5$ are i) all hydrogen, ii) form a triple bond together with one N, iii) $R_6$ and $R_7$ form a double bond together with NH, O, or S to form imine, oxo, or thioxo, respectively, and $R_8$ is $C_{1-6}$ alkoxy, amino, $C_{1-6}$ alkylamino, di($C_{1-6}$ alkyl)amino, or 5- to 14-membered heterocyclyl, or iv) $R_6$ to $R_5$ are connected to a heteroatom O, N, or S by a single or double bond, and comprise carbon and the heteroatom connected thereto to form unsubstituted or substituted 5- to 14-membered heteroaryl or heterocyclyl;

wherein the heteroaryl or heterocyclyl comprises at least one of O, N, and S, the substituted aryl, heteroaryl, or heterocyclyl may comprise $C_{1-6}$ alkyl; $C_{1-6}$ alkoxy; halogen; $C_{1-6}$ perfluoroalkyl; $C_{1-6}$ perfluoroalkoxy; $C_{1-6}$ haloalkyl; carbamoyl; carboxamido; $C_{6-10}$ aryloxy; unsubstituted $C_{6-14}$ aryl, 5- to 14-membered heteroaryl, or 5- to 14-membered heterocyclyl; or $C_{6-14}$ aryl, 5- to 14-membered heteroaryl, or 5- to 14-membered heterocyclyl substituted with at least one selected from the group consisting of $C_{1-6}$ alkyl, $C_{1-6}$ alkoxy, halogen, nitro, $C_{1-6}$ alkoxycarbonyl, $C_{1-6}$ perfluoroalkyl, $C_{1-6}$ perfluoroalkoxy, $C_{1-6}$ haloalkyl, amino, $C_{1-6}$ alkylamino, di($C_{1-6}$ alkyl)amino, and $C_{1-6}$ alkoxycarbonyl, as a substituent, and the carbamoyl and carboxamido may be substituted with at least one selected from the group consisting of $C_{1-6}$ alkyl, and aryl and heteroaryl unsubstituted or substituted with $C_{1-6}$ alkoxy, hydroxy, cyano, or $C_{1-6}$ alkyl.

A second aspect of the present invention is to provide a method of preparing the compound of the first aspect, comprising the step of reacting sodium nitrite, an amino derivative of $R_2$ ($R_2$—$NH_2$), and

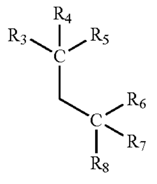

in the presence of acid to form an imine bond.

A third aspect of the present invention is to provide a method of preparing the compound of the first aspect, comprising the steps of:

a1) preparing an aniline derivative

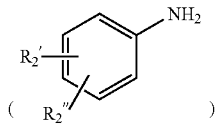

substituted with aryl or heteroaryl unsubstituted or substituted with $R_2$' or $R_2$"; and a2) reacting sodium nitrite, the aniline derivative

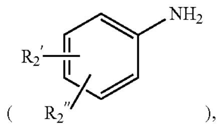

, and malononitrile in the presence of acid to form an imine bond.

A fourth aspect of the present invention is to provide a method of preparing the compound of the first aspect, comprising the step of reacting sodium nitrite, a 5-to 14-membered heteroaryl or 5- to 14-membered heterocyclyl derivative containing an amine group, and malononitrile in the presence of acid to form an imine bond.

A fifth aspect of the present invention is to provide a method of preparing the compound of the first aspect, comprising the steps of:

reacting carboxylic acid of $R_2$" or an anhydride thereof with

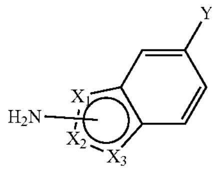

(here, Y is an unprotected or protected amine or nitro group) to form an amide bond; and reacting sodium nitrite, a heterocycle derivative comprising $R_2$" connected to a carboxamido group obtained from the previous step, and malononitrile in the presence of acid to form an imine bond.

A sixth aspect of the present invention is to provide a method of preparing the compound of the first aspect, comprising the steps of:

reacting sodium nitrite, an amino derivative of $R_2$ ($R_2$—$NH_2$), and

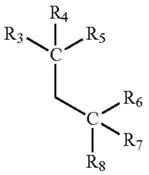

to form an imine bond; and adjusting the pH of the reaction solution to 5 to 7 using a base.

A seventh aspect of the present invention is to provide a composition for inhibiting the aggregation of tau protein comprising the compound of the present invention as an active ingredient.

An eighth aspect of the present invention is to provide a composition for inhibiting the hyperphosphorylation of tau protein comprising the compound of the present invention as an active ingredient.

A ninth aspect of the present invention is to provide a pharmaceutical composition for preventing or treating diseases caused by the aggregation or hyperphosphorylation of tau protein comprising the compound of the present invention as an active ingredient.

A tenth aspect of the present invention is to provide a method for preventing or treating diseases caused by the aggregation or hyperphosphorylation of tau protein, the method comprising the step of administering the pharmaceutical composition of the present invention to a subject in need thereof.

Advantageous Effects

According to the present invention, since the novel hydrazone derivative in which a terminal amine group is substituted with an aryl group or a heteroaryl group can effectively inhibit the aggregation and/or hyperphosphorylation of tau protein, this hydrazone derivative can be usefully used in the prevention or treatment of diseases caused thereby, such as Alzheimer's disease and various tauopathies.

BEST MODE OF THE INVENTION

A first aspect of the present invention is to provide a compound represented by Formula 1 below or a pharmaceutically acceptable salt thereof:

Formula 1

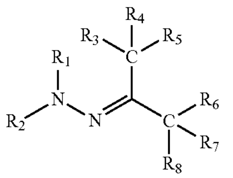

in Formula 1 above, $R_1$ is hydrogen or $C_{1-6}$ alkyl;

$R_1$ is unsubstituted or substituted $C_{6-14}$ aryl, 5- to 14-membered heteroaryl, or 5- to 14-membered heterocyclyl;

$R_3$ to $R_5$ are i) all hydrogen, ii) form a triple bond together with one N, iii) $R_3$ and $R_4$ form a double bond together with NH, O, or S to form imine, oxo, or thioxo, respectively, and $R_5$ is $C_{1-6}$ alkoxy, amino, $C_{1-6}$ alkylamino, di($C_{1-6}$ alkyl)amino, or 5- to 14-membered heterocyclyl, or iv) $R_3$ to $R_5$ are connected to a heteroatom O, N, or S by a single or double bond, and comprise carbon and the heteroatom connected thereto to form unsubstituted or substituted 5- to 14-membered heteroaryl or heterocyclyl; and $R_6$ to $R_8$ are i) all hydrogen, ii) form a triple bond together with one N, iii) $R_6$ and $R_7$ form a double bond together with NH, O, or S to form imine, oxo, or thioxo, respectively, and $R_8$ is $C_{1-6}$ alkoxy, amino, $C_{1-6}$ alkylamino, di($C_{1-6}$ alkyl)amino, or 5- to 14-membered heterocyclyl, or iv) $R_6$ to $R_5$ are connected to a heteroatom O, N, or S by a single or double bond, and comprise carbon and the heteroatom connected thereto to form unsubstituted or substituted 5- to 14-membered heteroaryl or heterocyclyl;

wherein the heteroaryl or heterocyclyl comprises at least one of O, N, and S, the substituted aryl, heteroaryl, or heterocyclyl may comprise $C_{1-6}$ alkyl; $C_1$-6 alkoxy; halogen; $C_{1-6}$ perfluoroalkyl; $C_{1-6}$ perfluoroalkoxy; $C_{1-6}$ haloalkyl; carbamoyl; carboxamido; $C_{6-10}$ aryloxy; unsubstituted $C_{6-14}$ aryl, 5- to 14-membered heteroaryl, or 5- to 14-membered heterocyclyl; or $C_{6-14}$ aryl, 5- to 14-membered heteroaryl, or 5- to 14-membered heterocyclyl substituted with at least one selected from the group consisting of $C_{1-6}$ alkyl, $C_{1-6}$ alkoxy, halogen, nitro, $C_{1-6}$ alkoxycarbonyl, $C_{1-6}$ perfluoroalkyl, $C_{1-6}$ perfluoroalkoxy, $C_{1-6}$ haloalkyl, amino, $C_{1-6}$ alkylamino, di($C_{1-6}$ alkyl)amino, and $C_{1-6}$ alkoxycarbonyl, as a substituent, and the carbamoyl and carboxamido may be substituted with at least one selected from the group consisting of $C_{1-6}$ alkyl, and aryl and heteroaryl unsubstituted or substituted with $C_{1-6}$ alkoxy, hydroxy, cyano, or $C_{1-6}$ alkyl.

Specifically, in the compound of the present invention, $R_1$ is hydrogen or methyl;

$R_2$ is unsubstituted or substituted phenyl, benzothiazolyl, carbazolyl, indazolyl, quinolinyl, indolyl, pyrrolopyridinyl, benzoisoxazolyl, dihydrobenzothiazolyl, oxodihydrobenzothiazolyl, benzoxazolyl, oxodihydrobenzoxazolyl, benzoimidazolyl, or oxodihydrobenzoimidazolyl;

$R_3$ to $R_5$ form —C≡N, —$CH_3$, —$CO_2Me$, —$CO_2Et$, —$CONH_2$, —$CSNH_2$,

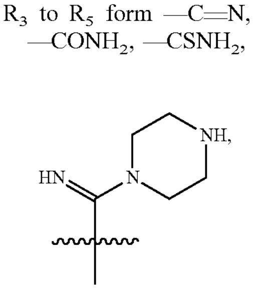

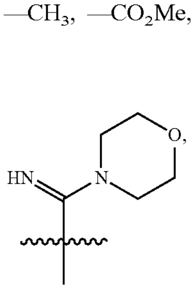

or

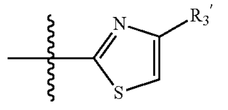

(here, $R_3$' is $C_{1-6}$ alkyl) together with C coupled therewith; and $R_6$ to $R_8$ form —CEN, —$CH_3$, —$CO_2Me$, —$CO_2Et$, —$CONH_2$, —$CSNH_2$,

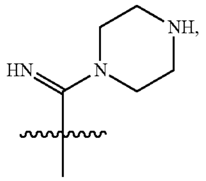

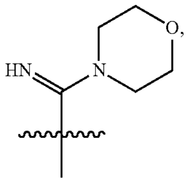

or

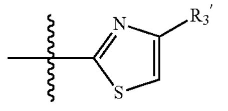

(here, $R_3$' is $C_{1-6}$ alkyl), wherein the heteroaryl and heterocyclyl comprises at least one O, N, or S, the substituted phenyl, benzothiazolyl, carbazolyl, indazolyl, quinolinyl, indolyl, pyrrolopyridinyl, benzoisoxazolyl, dihydrobenzothiazolyl, oxodihydrobenzothiazolyl, benzoxazolyl, oxodihydrobenzoxazolyl, benzoimidazolyl, or oxodihydrobenzoimidazolyl may comprise methyl, ethyl, propyl, isopropyl, trifluoromethyl, trifluoroethyl, methoxy, ethoxy, trifluoromethoxy, fluoro, chloro, bromo, morpholinyl, carbamoyl, carboxamido, phenoxy, or phenyl, piperidinyl, thiazolyl, pyridinyl, pyridazinyl, pyrazinyl, pyrimidinyl, triazolyl, pyrazolyl, benzothiazolyl, naphthyl, pyrazolopyrimidinyl, imidazopyrimidinyl, quinoxalnyl, imidazopyridinyl, isoquinolinyl, indazolyl, indolyl, furanyl, thiophenyl, oxotetrahydropyridazinyl, or oxodihydropyridazinyl, unsubstituted, or substituted with at least one selected from the group consisting of methyl, ethyl, ethynyl, methoxy, fluoro, chloro, bromo, nitro, dimethylamino, methoxycarbonyl, ethoxycarbonyl, and trifluoromethyl, as a substituent, and the carbamoyl and carboxamido may be substituted with at least one selected from the group consisting of methyl, ethyl, and phenyl, pyridinyl, pyrimidinyl, and pyrazinyl, unsubstituted or substituted with methyl, methoxy, hydroxy, or cyano.

For example, the compound of the present invention may be represented by Formula 2 below:

Formula 2

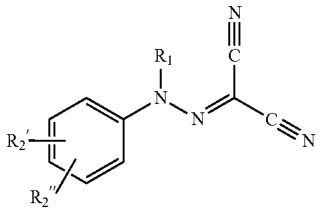

in Formula 2 above, $R_1$ is hydrogen or $C_{1-6}$ alkyl;

$R_2$' and $R_2$" are each independently hydrogen, $C_{1-6}$ alkyl, $C_{1-6}$ alkoxy, halogen, $C_{1-6}$ perfluoroalkyl, $C_{1-6}$ perfluoroalkoxy, $C_{1-6}$ haloalkyl, carbamoyl unsubstituted or substituted with $C_{1-6}$ alkyl, or $C_{6-14}$ aryl, 5- to 14-membered heteroaryl or 5- to 14-membered heterocyclyl unsubstituted or substituted with at least one selected from the group consisting of $C_{1-6}$ alkyl, $C_{1-6}$ alkoxy, halogen, nitro, $C_{1-6}$ alkoxycarbonyl, $C_{1-6}$ perfluoroalkyl, $C_{1-6}$ perfluoroalkoxy, $C_{1-6}$ haloalkyl, amino, $C_{1-6}$ alkylamino, di($C_{1-6}$ alkyl)amino, $C_{1-6}$ alkoxycarbonyl, and $C_{6-10}$ aryloxy.

Specifically, in Formula 2 above, $R_1$ is hydrogen or methyl;

$R_2$' is hydrogen, fluoro, methoxy, or morpholinyl; and $R_2$" is methyl, ethyl, propyl, isopropyl, trifluoromethyl, trifluoroethyl, methoxy, ethoxy, trifluoromethoxy, fluoro, chloro, bromo, morpholinyl, carbamoyl, carboxamido, phenoxy, or thiazolyl, pyridinyl, pyridazinyl, pyrazinyl, pyrimidinyl, triazolyl, pyrazolyl, benzothiazolyl, naphthyl, pyrazolopyrimidinyl, imidazopyrimidinyl, quinoxalinyl, imidazopyridinyl, isoquinolinyl, indazolyl, indolyl, oxotetrahydropyridazinyl, or oxodihydropyridazinyl unsubstituted or substituted with at least one selected from the group consisting of methyl, ethyl, ethynyl, methoxy, fluoro, chloro, bromo, nitro, dimethylamino, ethoxycarbonyl, and trifluoromethyl.

For example, the compound of the present invention may be represented by Formula 3 below:

Formula 3

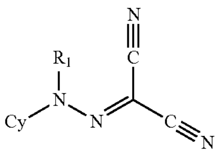

in Formula 3 above, $R_1$ is hydrogen or $C_{1-6}$ alkyl;

Cy is unsubstituted or substituted 5- to 14-membered heteroaryl or 5- to 14-membered heterocyclyl; and the substituted 5- to 14-membered heteroaryl or 5- to 14-membered heterocyclyl is unsubstituted or is substituted with $C_{1-6}$ alkyl; $C_{1-6}$ alkoxy; halogen; $C_{1-6}$ perfluoroalkyl; $C_{1-6}$ perfluoroalkoxy; $C_{1-6}$ haloalkyl; carbamoyl unsubstituted or substituted with $C_{1-6}$ alkyl; $C_{6-10}$ aryloxy; or $C_{6-14}$ aryl, 5- to 14-membered heteroaryl or 5- to 14-membered heterocyclyl unsubstituted or substituted with at least one selected from the group consisting of $C_{1-6}$ alkyl, halogen, and di($C_{1-6}$ alkyl)amino.

Specifically, in Formula 3 above, $R_1$ is hydrogen;

Cy is unsubstituted or substituted benzothiazolyl, carbazolyl, indazolyl, quinolinyl, indolyl, pyrrolopyridinyl, oxodihydrobenzothiazolyl, oxodihydrobenzoxazolyl, or oxodihydrobenzoimidazolyl; and the substituted 5- to 14-membered heteroaryl or 5- to 14-membered heterocyclyl is unsubstituted or is substituted with methyl, ethyl, propyl, butyl, isopropyl, isobutyl, methoxy, ethoxy, fluoro, chloro, bromo, trifluoroethyl, difluoromethyl, trifluoromethoxy, dimethylcarbamoyl, phenoxy, or phenyl, pyridinyl, furanyl, or thiophenyl unsubstituted or substituted with at least one selected from the group consisting of methyl, fluoro, and dimethylamino.

For example, the compound of the present invention may be represented by Formula 4 below:

Formula 4

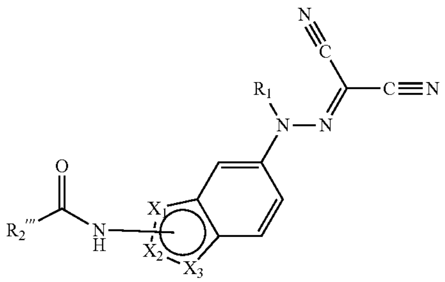

in Formula 4 above, $X_1$ to $X_3$ are different from each other, are each selected from C, N, O, and S, and are each connected to a carboxamido group through a C site;

$R_1$ is hydrogen or $C_{1-6}$ alkyl; and $R_2$" is $C_{1-6}$ alkyl, or aryl or heteroaryl unsubstituted or substituted with at least one selected from the group consisting of $C_{1-6}$ alkoxy, hydroxy, cyano, and $C_{1-6}$ alkyl.

Specifically, in Formula 4 above, $X_1$ to $X_3$ are sequentially N, C, and S or O, N, and C, and are connected to a carboxamido group through a C site;

$R_1$ is hydrogen; and $R_2$" is methyl, or phenyl, pyridinyl, pyrazinyl, or pyrimidinyl unsubstituted or substituted with at least one selected from the group consisting of methoxy, hydroxy, cyano, and methyl.

For example, the compound of the present invention may be represented by Formula 5 below:

Formula 5

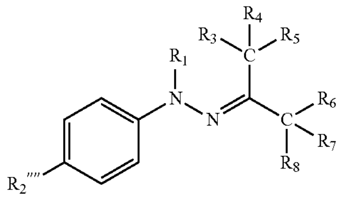

in Formula 5 above, $R_1$ is hydrogen or $C_{1-6}$ alkyl;

$R_2$" is 5- to 14-membered heteroaryl or 5- to 14-membered heterocyclyl unsubstituted or substituted with $C_{1-6}$ alkyl; and $R_3$ to $R_5$ are i) all hydrogen, ii) all form a triple bond together with one N, iii) $R_3$ and $R_4$ form a double bond together with NH, O, or S to form imine, oxo, or thioxo, respectively, and $R_5$ is $C_{1-6}$ alkoxy, amino, $C_{1-6}$ alkylamino, di($C_{1-6}$ alkyl)amino, or 5- to 14-membered heterocyclyl, or iv) $R_3$ to $R_5$ are connected to a heteroatom O, N, or S by a single or double bond, and comprise carbon and the heteroatom connected thereto to form unsubstituted or substituted 5- to 14-membered heteroaryl or heterocyclyl.

Specifically, in Formula 5 above, $R_1$ is hydrogen;

$R_2$" is pyrimidinyl or oxotetrahydropyridazinyl unsubstituted or substituted with at least one substituent selected from the group consisting of methyl, ethyl, propyl, butyl, isopropyl, isobutyl, and difluoromethyl;

$R_3$ to $R_5$ form —CEN, —$CH_3$, —$CO_2Me$, —$CO_2Et$, —$CONH_2$, —$CSNH_2$,

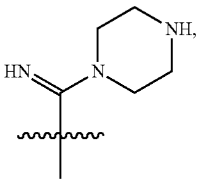

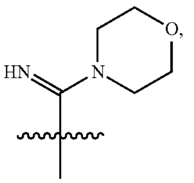

or

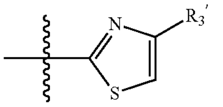

(here, $R_3$' is methyl) together with C connected thereto.

More specifically, the compound may be 1. (4-(pyrimidin-2-yl)phenyl)carbonohydrazonoyl dicyanide,
2. (4-(5-fluoropyrimidin-2-yl)phenyl)carbonohydrazonoyl dicyanide,
3. (4-(5-fluoro-4-methylpyrimidin-2-yl)phenyl)carbonohydrazonoyl dicyanide,
4. (4-(5-methylpyrimidin-2-yl)phenyl)carbonohydrazonoyl dicyanide,
5. (4-(5-ethylpyrimidin-2-yl)phenyl)carbonohydrazonoyl dicyanide,
6. (4-(4-ethylpyrimidin-2-yl)phenyl)carbonohydrazonoyl dicyanide,
7. (4-(5-chloropyrimidin-2-yl)carbonohydrazonoyl dicyanide,
8. (4-(5-methoxypyrimidin-2-yl)-phenyl)carbonohydrazonoyl dicyanide,
9. (4-(2,4-dimethylthiazol-5-yl)phenyl)carbonohydrazonoyl dicyanide,
10. (4-(pyridin-2-yl)phenyl)carbonohydrazonoyl dicyanide,
11. (4-(2-methylthiazol-5-yl)phenyl)carbonohydrazonoyl dicyanide,
12. (4-(4-methylthiazol-5-yl)phenyl)carbonohydrazonoyl dicyanide,
13. biphenyl-4-ylcarbonohydrazonoyl dicyanide,
14. (4'-methylbiphenyl-4-yl)carbonohydrazonoyl dicyanide,
15. (4-(pyridin-3-yl)phenyl)carbonohydrazonoyl dicyanide,
16. (4-(pyridin-4-yl)phenyl)carbonohydrazonoyl dicyanide,
17. (4-(pyridazin-3-yl)phenyl)carbonohydrazonoyl dicyanide,
18. (4-(5-methylthiazol-2-yl)phenyl)carbonohydrazonoyl dicyanide,
19. ethyl 2-(4-(2-(dicyanomethylene)hydrazinyl)phenyl) thiazole-5-carboxylate,
20. (4-(thiazol-5-yl)phenyl)carbonohydrazonoyl dicyanide,
21. (3'-fluoro-4'-nitrobiphenyl-4-yl)carbonohydrazonoyl dicyanide,
22. (4-(6-fluoropyridin-3-yl)phenyl)carbonohydrazonoyl dicyanide,
23. (2',4'-dimethylbiphenyl-4-yl)carbonohydrazonoyl dicyanide,
24 methyl 4'-(2-(dicyanomethylene)hydrazinyl)-2-fluorobiphenyl-4-carboxylate,
25. (2'-methyl-4'-nitrobiphenyl-4-yl)carbonohydrazonoyl dicyanide,
26. (2',4'-dichlorobiphenyl-4-yl)carbonohydrazonoyl dicyanide,
27. (2'-methoxy-4'-methylbiphenyl-4-yl)carbonohydrazonoyl dicyanide,
28. (4-(pyrazin-2-yl)phenyl)carbonohydrazonoyl dicyanide,
29. (4-(5-(trifluoromethyl)pyrimidin-2-yl)phenyl)carbonohydrazonoyl dicyanide,
30. (4-(4,6-dimethylpyrimidin-2-yl)phenyl)carbonohydrazonoyl dicyanide,
31. (4-(4-methylpyrimidin-2-yl)phenyl)carbonohydrazonoyl dicyanide,
32. (4-(pyrimidin-5-yl)phenyl)carbonohydrazonoyl dicyanide,
33. (4-(1-methyl-1H-1,2,4-triazol-5-yl)phenyl)carbonohydrazonoyl dicyanide,
34. (4-(1-methyl-1H-1,2,4-triazol-3-yl)phenyl)carbonohydrazonoyl dicyanide,
35. (4-(1H-pyrazol-1-yl)phenyl)carbonohydrazonoyl dicyanide,
36. (4-(4-methyl-1H-pyrazol-1-yl)phenyl)carbonohydrazonoyl dicyanide,
37. (2-fluoro-4-(4-methylpyrimidin-2-yl)phenyl)carbonohydrazonoyl dicyanide,
38. (2-fluoro-4-(pyrimidin-2-yl)phenyl)carbonohydrazonoyl dicyanide,
39. (3-fluoro-4-(pyrimidin-2-yl)phenyl)carbonohydrazonoyl dicyanide,
40. (3-fluoro-4-(4-methylpyrimidin-2-yl)phenyl)carbonohydrazonoyl dicyanide,
41. (2-methoxy-4-(5-methylpyrimidin-2-yl)phenyl)carbonohydrazonoyl dicyanide,
42. (2-methoxy-4-(4-methylpyrimidin-2-yl)phenyl)carbonohydrazonoyl dicyanide,
43. (2-methoxy-4-(pyrimidin-2-yl)phenyl)carbonohydrazonoyl dicyanide,
44. (4-(5-fluoropyrimidin-2-yl)-2-morpholinophenyl)carbonohydrazonoyl dicyanide,
45. methyl (4-(pyrimidin-2-yl)phenyl)carbonohydrazonoyl dicyanide,
46. (3-(5-fluoropyrimidin-2-yl)phenyl)carbonohydrazonoyl dicyanide,
47. (5-(5-fluoropyrimidin-2-yl)-2-morpholinophenyl)carbonohydrazonoyl dicyanide,
48. (4-(benzo[d]thiazol-6-yl)phenyl)carbonohydrazonoyl dicyanide,
49. (4-(naphthalen-2-yl)phenyl)carbonohydrazonoyl dicyanide,
50. (4-(pyrazolo[1,5-a]pyrimidin-6-yl)phenyl)carbonohydrazonoyl dicyanide,
51. (4-(imidazo[1,2-a]pyrimidin-6-yl)phenyl)carbonohydrazonoyl dicyanide,
52. (4-(quinoxalin-2-yl)phenyl)carbonohydrazonoyl dicyanide,
53. (4-(imidazo[1,2-a]pyridin-6-yl)phenyl)carbonohydrazonoyl dicyanide, 54. (4-(isoquinolin-3-yl)phenyl)carbonohydrazonoyl dicyanide,
55. (4-(2-methyl-2H-indazol-4-yl)phenyl)carbonohydrazonoyl dicyanide,
56. (4-(2-methyl-2H-indazol-5-yl)phenyl)carbonohydrazonoyl dicyanide,
57. (4-(2-methyl-2H-indazol-7-yl)phenyl)carbonohydrazonoyl dicyanide,
58. (4-(1H-indol-5-yl)phenyl)carbonohydrazonoyl dicyanide,
59. (4-methoxybenzo[d]thiazol-2-yl)carbonohydrazonoyl dicyanide,
60. benzo[d]thiazol-6-ylcarbonohydrazonoyl dicyanide,
61. benzo[d]thiazol-5-ylcarbonohydrazonoyl dicyanide,
62. (9-ethyl-9H-carbazol-3-yl)carbonohydrazonoyl dicyanide,
63. (1-methyl-1H-indazol-6-yl)carbonohydrazonoyl dicyanide,
64. quinolin-3-ylcarbonohydrazonoyl dicyanide,
65. (2-methyl-2H-indazol-6-yl)carbonohydrazonoyl dicyanide,
66. (1-methyl-1H-indazol-5-yl)carbonohydrazonoyl dicyanide,
67. quinoline-6-ylcarbonohydrazonoyl dicyanide,
68. (1-methyl-1H-indol-5-yl)carbonohydrazonoyl dicyanide,
69. (1H-indazol-5-yl)carbonohydrazonoyl dicyanide,
70. (1H-indazol-6-yl)carbonohydrazonoyl dicyanide,
71. (1H-indol-5-yl)carbonohydrazonoyl dicyanide,
72. (1H-pyrrolo[2,3-b]pyridin-5-yl)carbonohydrazonoyl dicyanide,
73. (3-methyl-1H-indazol-6-yl)carbonohydrazonoyl dicyanide,
74. (3-methyl-1H-indazol-5-yl)carbonohydrazonoyl dicyanide,
75. (1H-indol-4-yl)carbonohydrazonoyl dicyanide,
76. (1-methyl-1H-pyrrolo[2,3-b]pyridin-5-yl)carbonohydrazonoyl dicyanide,
77. (1-propyl-1H-pyrrolo[2,3-b]pyridin-5-yl)carbonohydrazonoyl dicyanide,
78. (1-isopropyl-1H-pyrrolo[2,3-b]pyridin-5-yl)carbonohydrazonoyl dicyanide,
79. (1-ethyl-1H-pyrrolo[2,3-b]pyridin-5-yl)carbonohydrazonoyl dicyanide,
80. (1-(2,2,2-trifluoroethyl)-1H-pyrrolo[2,3-b]pyridin-5-yl)carbonohydrazonoyl dicyanide,
81. (2-methyl-1H-pyrrolo[2,3-b]pyridin-5-yl)carbonohydrazonoyl dicyanide,
82. (3-methyl-1H-pyrrolo[2,3-b]pyridin-5-yl)carbonohydrazonoyl dicyanide,
83. (3-chloro-1H-pyrrolo[2,3-b]pyridin-5-yl)carbonohydrazonoyl dicyanide,
84. (4-methoxy-1H-pyrrolo[2,3-b]pyridin-5-yl)carbonohydrazonoyl dicyanide,
85. (2-(dimethylcarbamoyl)-1H-pyrrolo[2,3-b]pyridin-5-yl)carbonohydrazonoyl dicyanide,
86. (2-(4-methoxybenzamido)benzo[d]thiazol-6-yl)carbonohydrazonoyl dicyanide,
87. (2-(2-hydroxybenzamido)benzo[d]thiazol-6-yl)carbonohydrazonoyl dicyanide,
88. (2-acetamidobenzo[d]thiazol-6-yl)carbonohydrazonoyl dicyanide,
89. (2-(3-cyanobenzamido)benzo[d]thiazol-6-yl)carbonohydrazonoyl dicyanide,
90. (2-(5-methylnicotinamido)benzo[d]thiazol-6-yl)carbonohydrazonoyl dicyanide,
91. (2-(3-hydroxypicolinamido)benzo[d]thiazol-6-yl)carbonohydrazonoyl dicyanide,
92. (2-(pyrazine-2-carboxamido)benzo[d]thiazol-6-yl)carbonohydrazonoyl dicyanide,
93. (2-(5-methylpyrazine-2-carboxamido)benzo[d]thiazol-6-yl)carbonohydrazonoyl dicyanide,
94. (2-(pyrimidine-5-carboxamido)benzo[d]thiazol-6-yl)carbonohydrazonoyl dicyanide,
95. (2-(2-methylpyrimidine-5-carboxamido)benzo[d]thiazol-6-yl)carbonohydrazonoyl dicyanide,
96. (2-(4-methylpyrimidine-5-carboxamido)benzo[d]thiazol-6-yl)carbonohydrazonoyl dicyanide,
97. (2-(3-methylpyrazine-2-carboxamido)benzo[d]thiazol-6-yl)carbonohydrazonoyl dicyanide,
98. (2-(6-methylpyrazine-2-carboxamido)benzo[d]thiazol-6-yl)carbonohydrazonoyl dicyanide,
99. (2-(pyrazine-2-carboxamido)benzo[d]thiazol-5-yl)carbonohydrazonoyl dicyanide,
100. (2-(5-methylpyrazine-2-carboxamido)benzo[d]thiazol-5-yl)carbonohydrazonoyl dicyanide,
101. (2-phenylbenzo[d]thiazol-6-yl)carbonohydrazonoyl dicyanide,
102. (2-(4-fluorophenyl)benzo[d]thiazol-6-yl)carbonohydrazonoyl dicyanide,
103. (2-(4-(dimethylamino)phenyl)benzo[d]thiazol-6-yl)carbonohydrazonoyl dicyanide,
104. (2-(pyridin-3-yl)benzo[d]thiazol-6-yl)carbonohydrazonoyl dicyanide,
105. (2-(6-methylpyridin-3-yl)benzo[d]thiazol-6-yl)carbonohydrazonoyl dicyanide,
106. (2-(6-fluoropyridin-3-yl)benzo[d]thiazol-6-yl)carbonohydrazonoyl dicyanide,
107. (2-(furan-2-yl)benzo[d]thiazol-6-yl)carbonohydrazonoyl dicyanide,
108. (2-(thiophen-2-yl)benzo[d]thiazol-6-yl)carbonohydrazonoyl dicyanide,
109. (2-(5-fluoropyridin-3-yl)benzo[d]thiazol-6-yl)carbonohydrazonoyl dicyanide,
110. (2-(5-methylpyridin-3-yl)benzo[d]thiazol-6-yl)carbonohydrazonoyl dicyanide,
111. (2-(pyridin-3-yl)benzo[d]thiazol-5-yl)carbonohydrazonoyl dicyanide,
112. (2-(5-methylpyridin-3-yl)benzo[d]thiazol-5-yl)carbonohydrazonoyl dicyanide,
113. benzo[d]thiazol-2-ylcarbonohydrazonoyl dicyanide,
114. (6-fluorobenzo[d]thiazol-2-yl)carbonohydrazonoyl dicyanide,
115. (6-chlorobenzo[d]thiazol-2-yl)carbonohydrazonoyl dicyanide,
116. (6-bromobenzo[d]thiazol-2-yl)carbonohydrazonoyl dicyanide,
117. (6-(trifluoromethyl)benzo[d]thiazol-2-yl)carbonohydrazonoyl dicyanide,
118. (4-chlorobenzo[d]thiazol-2-yl)carbonohydrazonoyl dicyanide,
119. (5-chlorobenzo[d]thiazol-2-yl)carbonohydrazonoyl dicyanide,
120. (5-bromobenzo[d]thiazol-2-yl)carbonohydrazonoyl dicyanide,
121. (6-methoxybenzo[d]thiazol-2-yl)carbonohydrazonoyl dicyanide,
122. (6-ethoxybenzo[d]thiazol-2-yl)carbonohydrazonoyl dicyanide,
123. (6-(trifluoromethoxy)benzo[d]thiazol-2-yl)carbonohydrazonoyl dicyanide,
124. (6-methylbenzo[d]thiazol-2-yl)carbonohydrazonoyl dicyanide, 125. (4-methylbenzo[d]thiazol-2-yl)carbonohydrazonoyl dicyanide,
126. (4,6-dimethylbenzo[d]thiazol-2-yl)carbonohydrazonoyl dicyanide,
127. (5,6-dimethylbenzo[d]thiazol-2-yl)carbonohydrazonoyl dicyanide,
128. (6-phenoxybenzo[d]thiazol-2-yl)carbonohydrazonoyl dicyanide,
129. (6-phenylbenzo[d]thiazol-2-yl)carbonohydrazonoyl dicyanide,
130. (3-(pyrazine-2-carboxamido)benzo[d]isoxazol-5-yl)carbonohydrazonoyl dicyanide,
131. (3-(5-methylpyrazine-2-carboxamido)benzo[d]isooxazol-5-yl)carbonohydrazonoyl dicyanide,
132. (3-(3-cyanobenzamido)benzo[d]isooxazol-5-yl)carbonohydrazonoyl dicyanide,
133. (3-(4-methoxybenzamido)benzo[d]isooxazol-5-yl)carbonohydrazonoyl dicyanide,
134. (2-oxo-2,3-dihydrobenzo[d]thiazol-6-yl)carbonohydrazonoyl dicyanide,
135. (3-methyl-2-oxo-2,3-dihydrobenzo[d]thiazol-6-yl)carbonohydrazonoyl dicyanide,
136. (2-methoxybenzo[d]thiazol-6-yl)carbonohydrazonoyl dicyanide,
137. (2-oxo-2,3-dihydrobenzo[d]oxazol-6-yl)carbonohydrazonoyl dicyanide,
138. (3-methyl-2-oxo-2,3-dihydrobenzo[d]oxazol-6-yl)carbonohydrazonoyl dicyanide,
139. (2-oxo-2,3-dihydro-1H-benzo[d]imidazol-5-yl)carbonohydrazonoyl dicyanide,
140. diethyl 2-(2-(4-(4-methyl-6-oxo-1,4,5,6-tetrahydropyridazin-3-yl)phenyl)hydrazono)malonate,
141. 2-imino-N'-(4-(4-methyl-6-oxo-1,4,5,6-tetrahydropyridazin-3-yl)phenyl)-2-(piperazin-1-yl)acetohydrazonoyl cyanide,
142. 2-imino-N'-(4-(4-methyl-6-oxo-1,4,5,6-tetrahydropyridazin-3-yl)phenyl)-2-morpholinoacetohydrazonoyl cyanide,
143. methyl 2-(2-(4-(4-methyl-6-oxo-1,4,5,6-tetrahydropyridazin-3-yl)phenyl)hydrazono) propanoate,
144. methyl-2-cyano-2-(2-(4-(pyrimidin-2-yl)phenyl)hydrazono)acetate,
145. 2-amino-2-oxo-N'-(4-(pyrimidin-2-yl)phenyl)acetohydrazonoyl cyanide,
146. ethyl-2-cyano-2-(2-(4-(pyrimidin-2-yl)phenyl)hydrazono)acetate,
147. 2-amino-N'-(4-(pyrimidin-2-yl)phenyl)-2-thioxoacetohydrazonoyl cyanide,
148. 4-methyl-N'-(4-(pyrimidin-2-yl)phenyl) thiazole-2-carbohydrazonoyl cyanide,
149. (4-(5-ethynylpyrimidin-2-yl)phenyl)carbohydrazonoyl dicyanide,
150. (4'-(dimethylamino)-3-fluorobiphenyl-4-yl)carbohydrazonoyl dicyanide,
151. (4'-(dimethylamino) biphenyl-4-yl)carbohydrazonoyl dicyanide,
152. (4-(6-(dimethylamino)pyridin-3-yl)phenyl)carbohydrazonoyl dicyanide,
153. (4-(6-oxo-1,6-dihydropyridazin-3-yl)phenyl)carbohydrazonoyl dicyanide,
154. (4-(4-methyl-6-oxo-1,6-dihydropyridazin-3-yl)phenyl)carbohydrazonoyl dicyanide,
155. (4-(5-methyl-6-oxo-1,6-dihydropyridazin-3-yl)phenyl)carbohydrazonoyl dicyanide,
156. (4-(1-methyl-6-oxo-1,6-dihydropyridazin-3-yl)phenyl)carbohydrazonoyl dicyanide,
157. (4-(1,4-dimethyl-6-oxo-1,6-dihydropyridazin-3-yl)phenyl)carbohydrazonoyl dicyanide,
158. (4-(1,5-dimethyl-6-oxo-1,6-dihydropyridazin-3-yl)phenyl)carbohydrazonoyl dicyanide,
159. (3-isopropyl-2-oxo-2,3-dihydrobenzo[d]thiazol-6-yl)carbohydrazonoyl dicyanide,
160. (3-(difluoromethyl)-2-oxo-2,3-dihydrobenzo[d]thiazol-6-yl)carbohydrazonoyl dicyanide,
161. (2-isopropoxybenzo[d]thiazol-6-yl)carbohydrazonoyl dicyanide,
162. (3-isopropyl-2-oxo-2,3-dihydrobenzo[d]oxazol-6-yl)carbohydrazonoyl dicyanide,
163. (3-(difluoromethyl)-2-oxo-2,3-dihydrobenzo[d]oxazol-6-yl)carbohydrazonoyl dicyanide,
164. (1,3-dimethyl-2-oxo-2,3-dihydro-1H-benzo[d]imidazol-5-yl)carbohydrazonoyl dicyanide,
165. (1,3-diisopropyl-2-oxo-2,3-dihydro-1H-benzo[d]imidazol-5-yl)carbohydrazonoyl dicyanide,
166. (1,3-bis(difluoromethyl)-2-oxo-2,3-dihydro-1H-benzo[d]imidazol-5-yl)carbohydrazonoyl dicyanide,
167. (2-(methylamino)benzo[d]thiazol-6-yl)carbohydrazonoyl dicyanide,
168. (2-(dimethylamino)benzo[d]thiazol-6-yl)carbohydrazonoyl dicyanide,
169. (4-(6-oxo-1,4,5,6-tetrahydropyridazin-3-yl)phenyl)carbohydrazonoyl dicyanide,
170. (4-(1-methyl-6-oxo-1,4,5,6-tetrahydropyridazin-3-yl)phenyl)carbohydrazonoyidicyanide, or
171. (4-(1,4-dimethyl-6-oxo-1,4,5,6-tetrahydropyridazin-3-yl)phenyl)carbohydrazonoyidicyanide.

Furthermore, these compounds may be compounds represented by the following formulas.

1

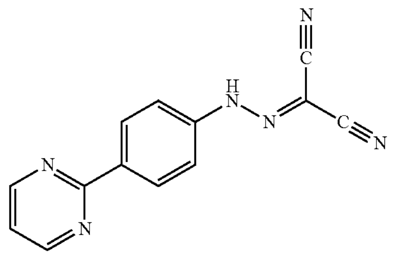 [SMILES: N#CC(C#N)=NNc1ccc(-c2ncccn2)cc1]

2

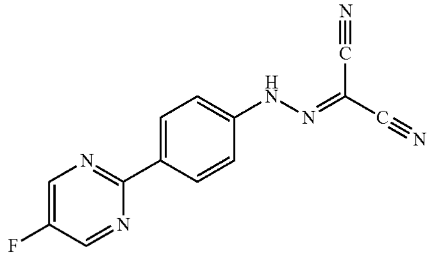 [SMILES: N#CC(C#N)=NNc1ccc(-c2ncc(F)cn2)cc1]

3

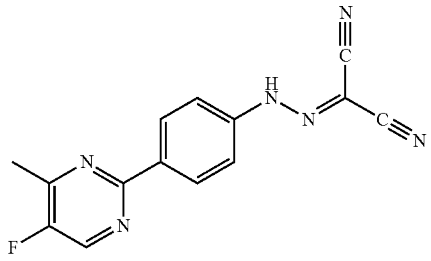 [SMILES: Cc1nc(-c2ccc(NN=C(C#N)C#N)cc2)ncc1F]

-continued
4
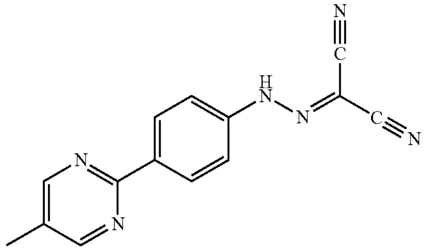 [SMILES: Cc1cnc(-c2ccc(NN=C(C#N)C#N)cc2)nc1]
5
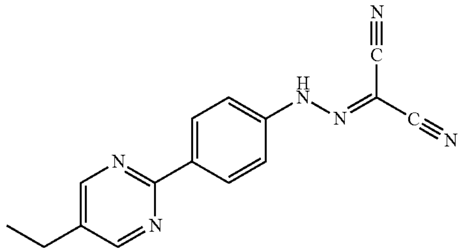 [SMILES: CCc1cnc(-c2ccc(NN=C(C#N)C#N)cc2)nc1]
6
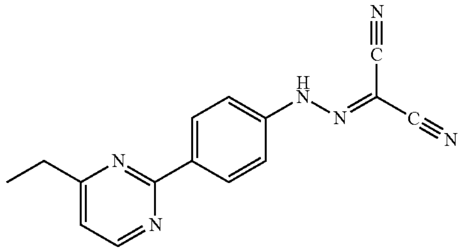 [SMILES: CCc1ccnc(-c2ccc(NN=C(C#N)C#N)cc2)n1]
7
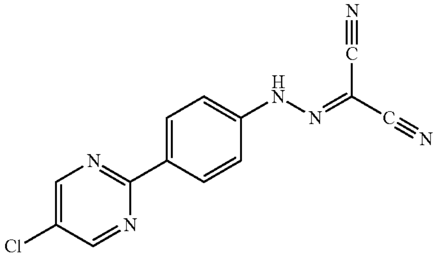 [SMILES: N#CC(C#N)=NNc1ccc(-c2ncc(Cl)cn2)cc1]
8
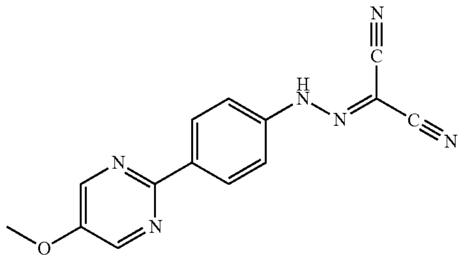 [SMILES: COc1cnc(-c2ccc(NN=C(C#N)C#N)cc2)nc1]
9
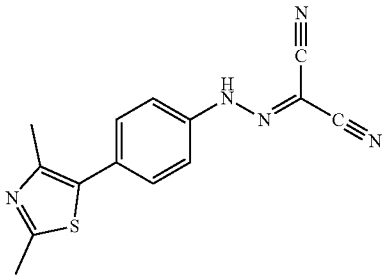 [SMILES: Cc1nc(C)c(-c2ccc(NN=C(C#N)C#N)cc2)s1]
-continued
10
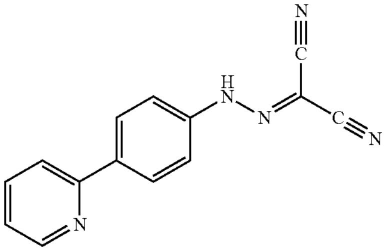 [SMILES: N#CC(C#N)=NNc1ccc(-c2ccccn2)cc1]
11
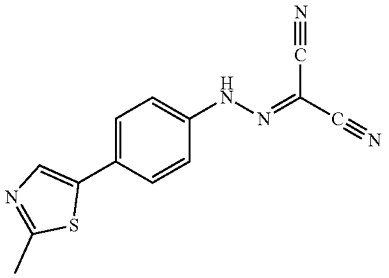 [SMILES: Cc1ncc(-c2ccc(NN=C(C#N)C#N)cc2)s1]
12
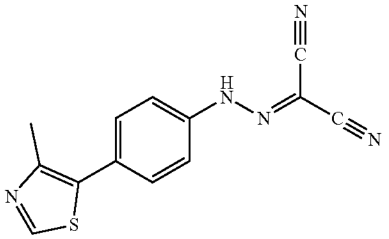 [SMILES: Cc1ncsc1-c1ccc(NN=C(C#N)C#N)cc1]
13
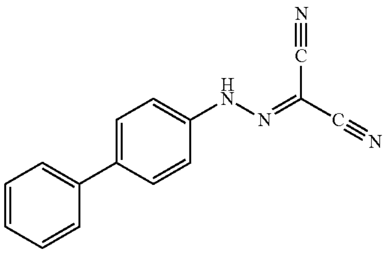
14
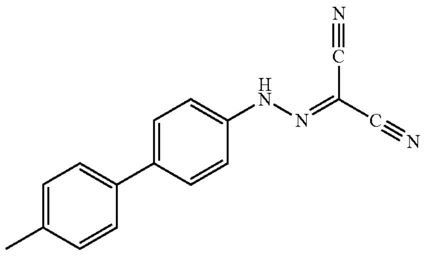 [SMILES: Cc1ccc(-c2ccc(NN=C(C#N)C#N)cc2)cc1]
15
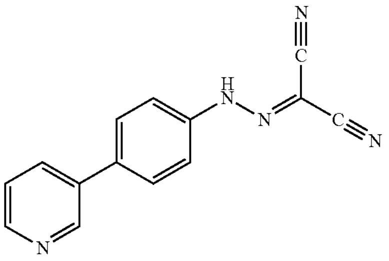 [SMILES: N#CC(C#N)=NNc1ccc(-c2cccnc2)cc1]

-continued
16
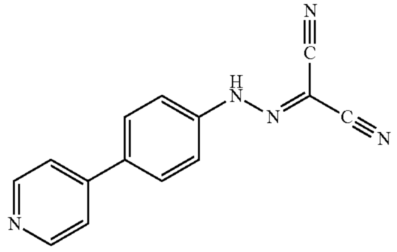 [SMILES: N#CC(C#N)=NNc1ccc(-c2ccncc2)cc1]
17
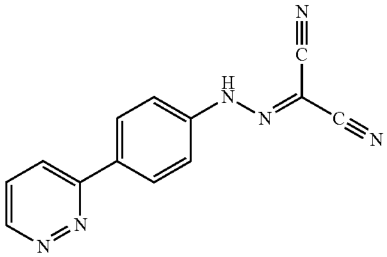 [SMILES: N#CC(C#N)=NNc1ccc(-c2cccnn2)cc1]
18
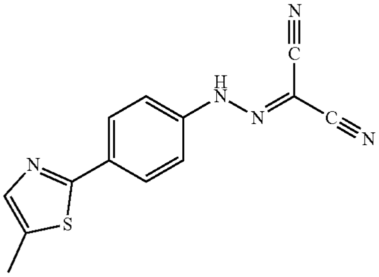 [SMILES: Cc1cnc(-c2ccc(NN=C(C#N)C#N)cc2)s1]
19
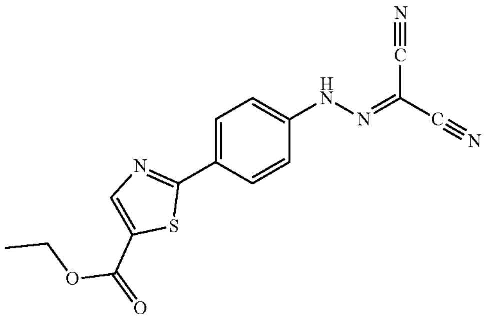 [SMILES: CCOC(=O)c1cnc(-c2ccc(NN=C(C#N)C#N)cc2)s1]
20
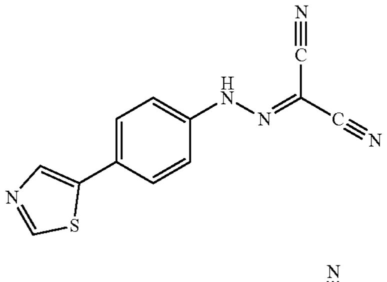
21
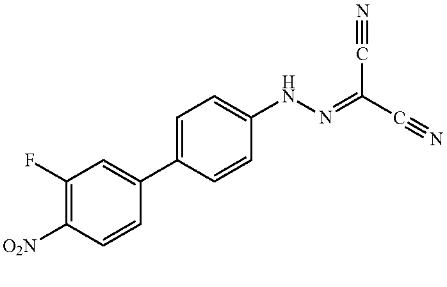 [SMILES: N#CC(C#N)=NNc1ccc(-c2ccc([N+](=O)[O-])c(F)c2)cc1]
-continued
22
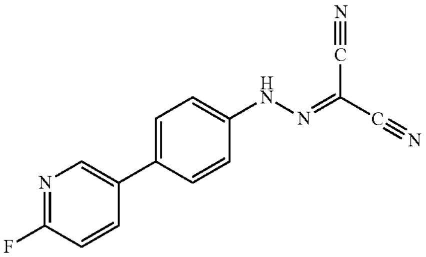 [SMILES: N#CC(C#N)=NNc1ccc(-c2ccc(F)nc2)cc1]
23
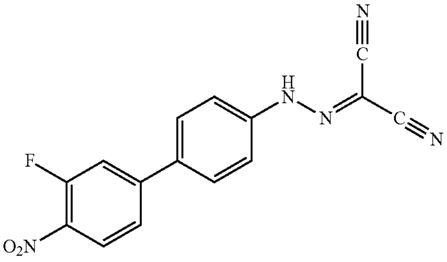 [SMILES: N#CC(C#N)=NNc1ccc(-c2ccc([N+](=O)[O-])c(F)c2)cc1]
24
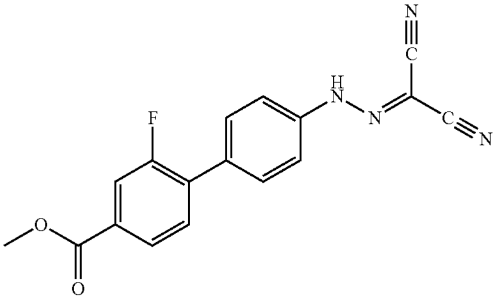 [SMILES: COC(=O)c1ccc(-c2ccc(NN=C(C#N)C#N)cc2)c(F)c1]
25
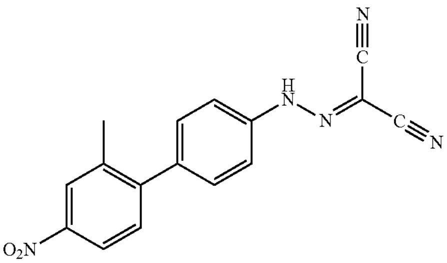 [SMILES: Cc1cc([N+](=O)[O-])ccc1-c1ccc(NN=C(C#N)C#N)cc1]
26
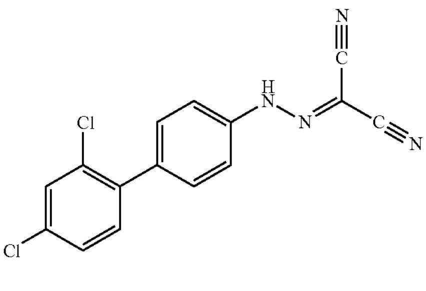 [SMILES: N#CC(C#N)=NNc1ccc(-c2ccc(Cl)cc2Cl)cc1]

-continued
27
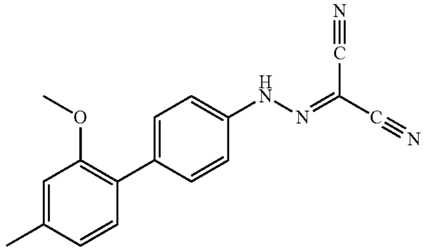 [SMILES: COc1cc(C)ccc1-c1ccc(NN=C(C#N)C#N)cc1]
28
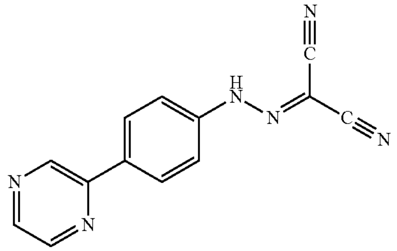 [SMILES: N#CC(C#N)=NNc1ccc(-c2cnccn2)cc1]
29
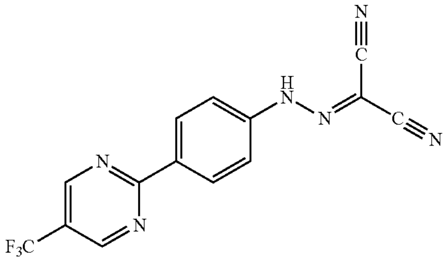 [SMILES: N#CC(C#N)=NNc1ccc(-c2ncc(C(F)(F)F)cn2)cc1]
30
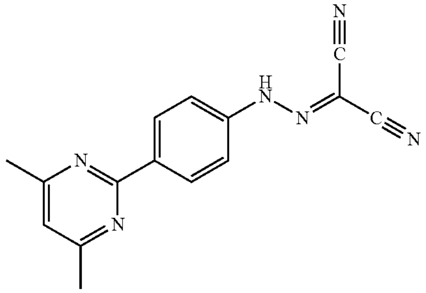 [SMILES: Cc1cc(C)nc(-c2ccc(NN=C(C#N)C#N)cc2)n1]
31
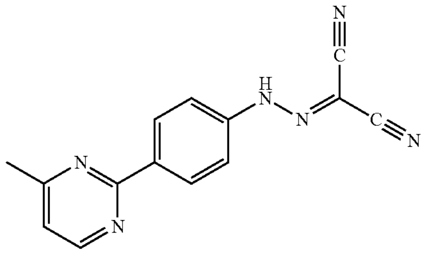 [SMILES: Cc1ccnc(-c2ccc(NN=C(C#N)C#N)cc2)n1]
32
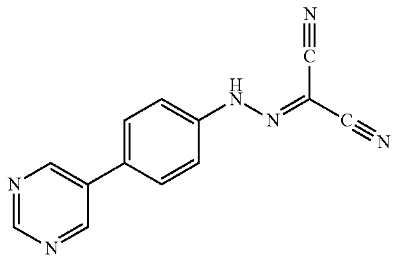 [SMILES: N#CC(C#N)=NNc1ccc(-c2cncnc2)cc1]
-continued
33
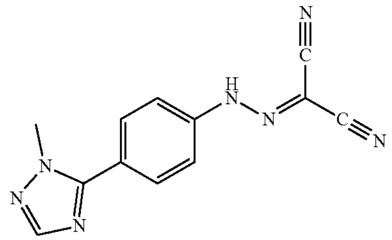 [SMILES: Cn1ncnc1-c1ccc(NN=C(C#N)C#N)cc1]
34
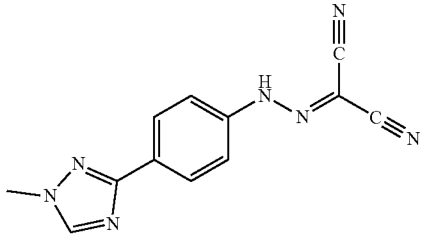 [SMILES: Cn1cnc(-c2ccc(NN=C(C#N)C#N)cc2)n1]
35
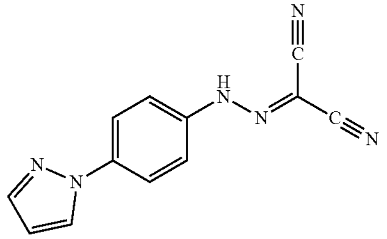 [SMILES: N#CC(C#N)=NNc1ccc(-n2cccn2)cc1]
36
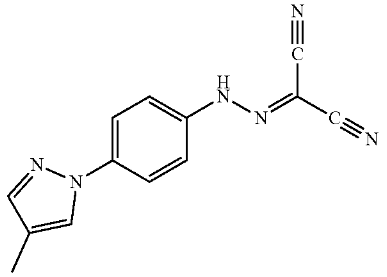 [SMILES: Cc1cnn(-c2ccc(NN=C(C#N)C#N)cc2)c1]
37
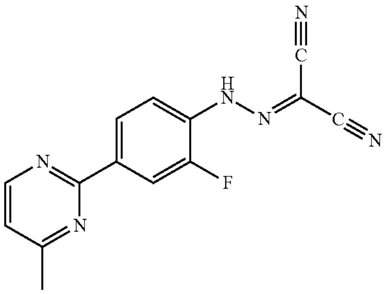 [SMILES: Cc1ccnc(-c2ccc(NN=C(C#N)C#N)c(F)c2)n1]
38
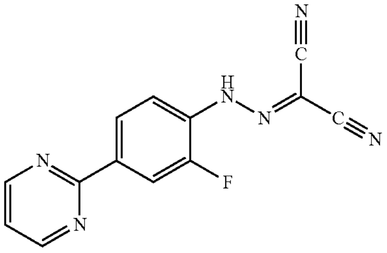 [SMILES: N#CC(C#N)=NNc1ccc(-c2ncccn2)cc1F]

-continued
39
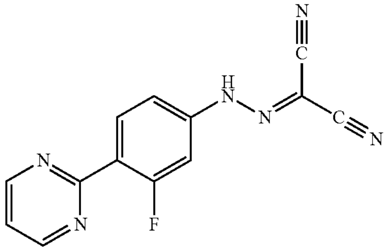 [SMILES: N#CC(C#N)=NNc1ccc(-c2ncccn2)c(F)c1]
40
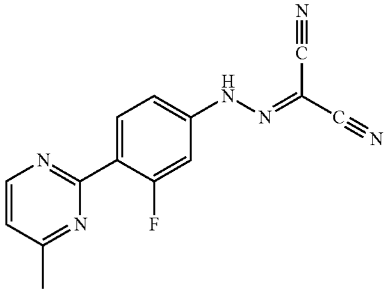 [SMILES: Cc1ccnc(-c2ccc(NN=C(C#N)C#N)cc2F)n1]
41
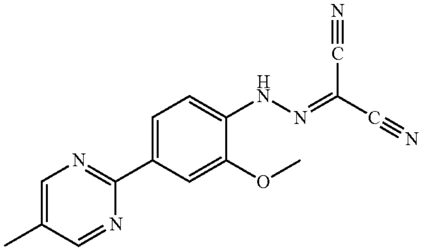 [SMILES: COc1cc(-c2ncc(C)cn2)ccc1NN=C(C#N)C#N]
42
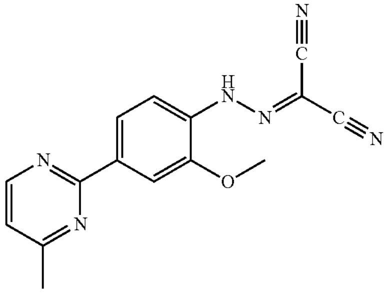 [SMILES: COc1cc(-c2nccc(C)n2)ccc1NN=C(C#N)C#N]
43
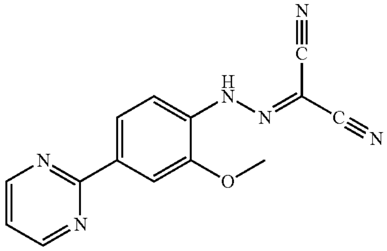 [SMILES: COc1cc(-c2ncccn2)ccc1NN=C(C#N)C#N]
44
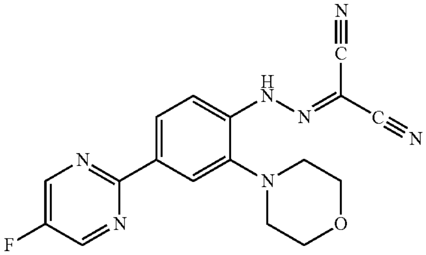 [SMILES: N#CC(C#N)=NNc1ccc(-c2ncc(F)cn2)cc1N1CCOCC1]
-continued
45
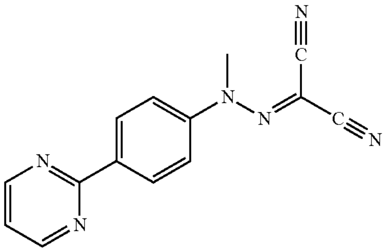 [SMILES: CN(N=C(C#N)C#N)c1ccc(-c2ncccn2)cc1]
46
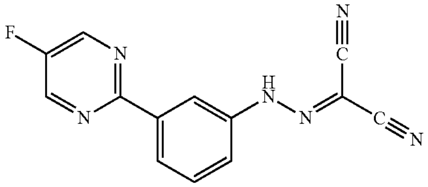 [SMILES: N#CC(C#N)=NNc1cccc(-c2ncc(F)cn2)c1]
47
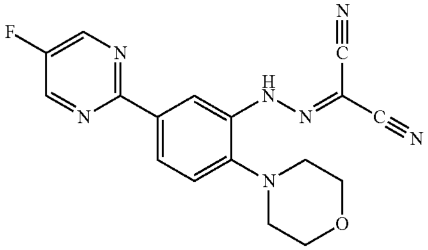 [SMILES: N#CC(C#N)=NNc1cc(-c2ncc(F)cn2)ccc1N1CCOCC1]
48
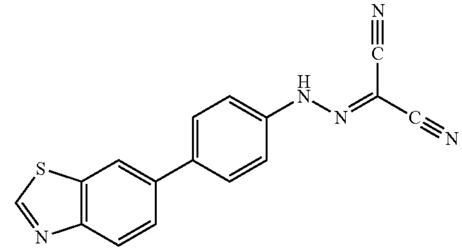 [SMILES: N#CC(C#N)=NNc1ccc(-c2ccc3ncsc3c2)cc1]
49
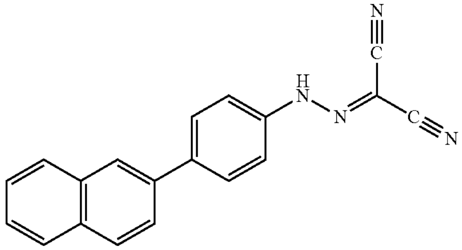 [SMILES: N#CC(C#N)=NNc1ccc(-c2ccc3ccccc3c2)cc1]
50
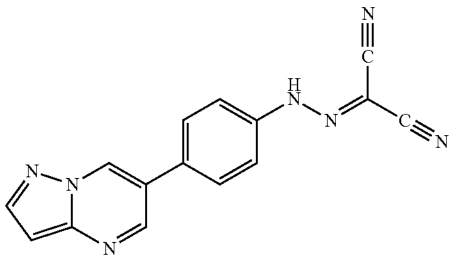 [SMILES: N#CC(C#N)=NNc1ccc(-c2cnc3ccnn3c2)cc1]

-continued
51
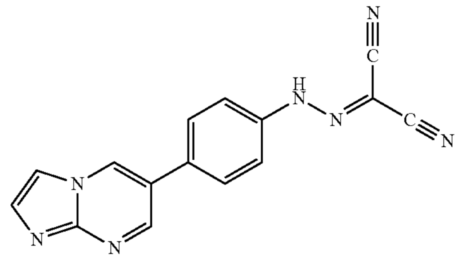 [SMILES: N#CC(C#N)=NNc1ccc(-c2cnc3nccn3c2)cc1]
52
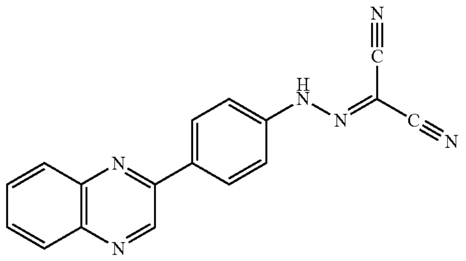 [SMILES: N#CC(C#N)=NNc1ccc(-c2cnc3ccccc3n2)cc1]
53
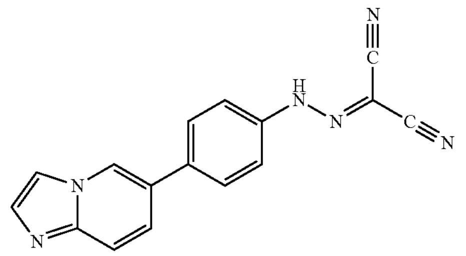 [SMILES: N#CC(C#N)=NNc1ccc(-c2ccc3nccn3c2)cc1]
54
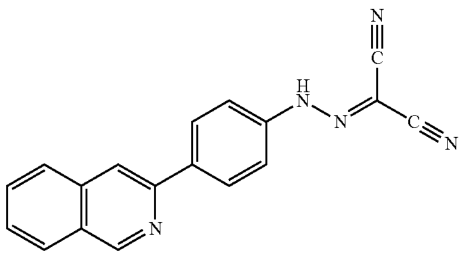 [SMILES: N#CC(C#N)=NNc1ccc(-c2cc3ccccc3cn2)cc1]
55
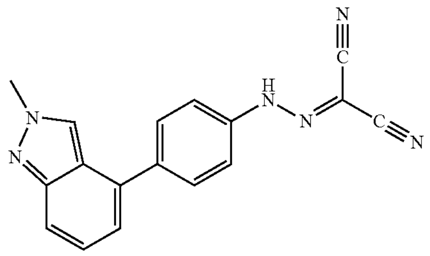 [SMILES: Cn1cc2c(-c3ccc(NN=C(C#N)C#N)cc3)cccc2n1]
56
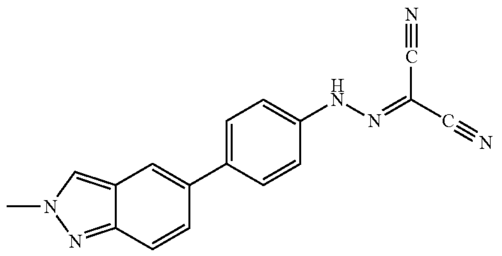 [SMILES: Cn1cc2cc(-c3ccc(NN=C(C#N)C#N)cc3)ccc2n1]
-continued
57
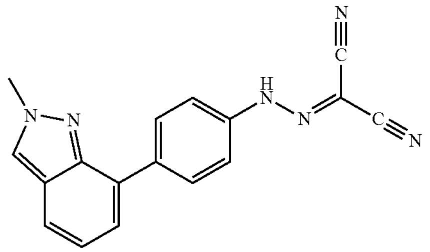 [SMILES: Cn1cc2cccc(-c3ccc(NN=C(C#N)C#N)cc3)c2n1]
58
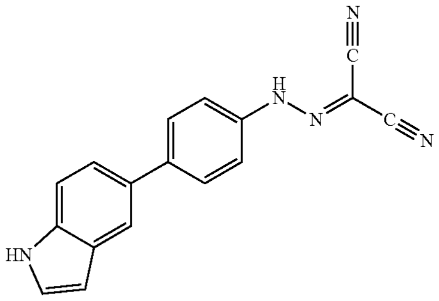 [SMILES: N#CC(C#N)=NNc1ccc(-c2ccc3[nH]ccc3c2)cc1]
59
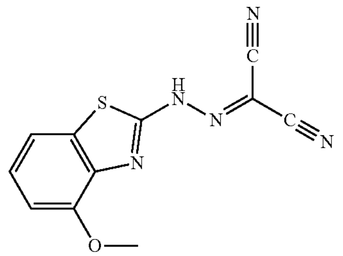 [SMILES: COc1cccc2sc(NN=C(C#N)C#N)nc12]
60
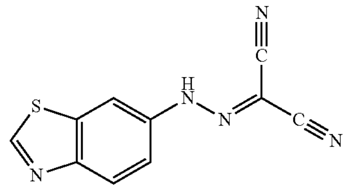 [SMILES: N#CC(C#N)=NNc1ccc2ncsc2c1]
61
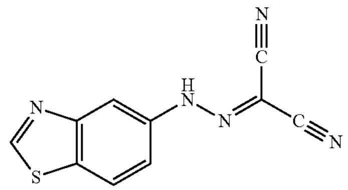 [SMILES: N#CC(C#N)=NNc1ccc2scnc2c1]
62
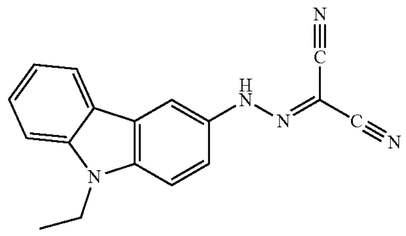 [SMILES: CCn1c2ccccc2c2cc(NN=C(C#N)C#N)ccc21]

-continued
63
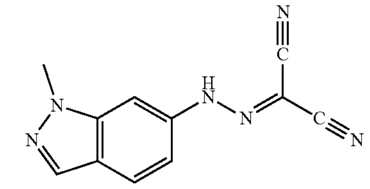 [SMILES: Cn1ncc2ccc(NN=C(C#N)C#N)cc21]
64
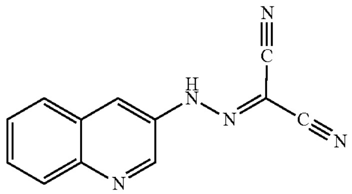 [SMILES: N#CC(C#N)=NNc1cnc2ccccc2c1]
65
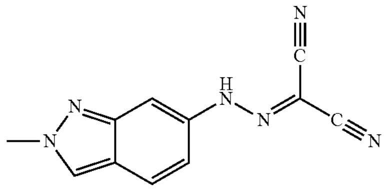 [SMILES: Cn1cc2ccc(NN=C(C#N)C#N)cc2n1]
66
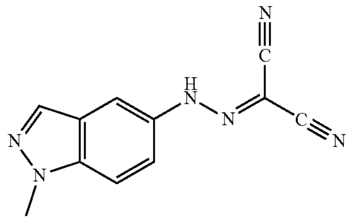 [SMILES: Cn1ncc2cc(NN=C(C#N)C#N)ccc21]
67
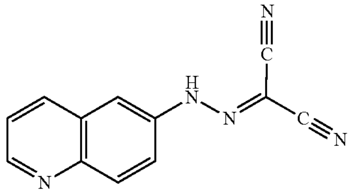 [SMILES: N#CC(C#N)=NNc1ccc2ncccc2c1]
68
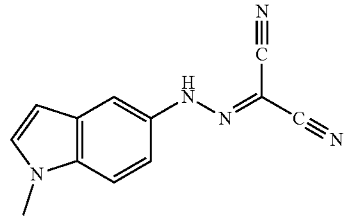 [SMILES: Cn1ccc2cc(NN=C(C#N)C#N)ccc21]
69
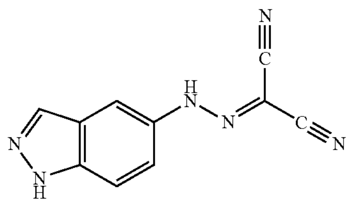 [SMILES: N#CC(C#N)=NNc1ccc2[nH]ncc2c1]
-continued
70
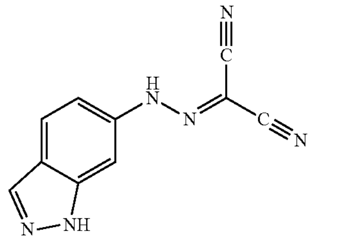 [SMILES: N#CC(C#N)=NNc1ccc2cn[nH]c2c1]
71
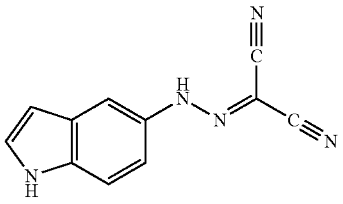 [SMILES: N#CC(C#N)=NNc1ccc2[nH]ccc2c1]
72
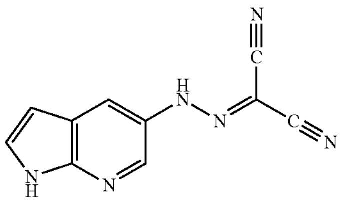 [SMILES: N#CC(C#N)=NNc1cnc2[nH]ccc2c1]
73
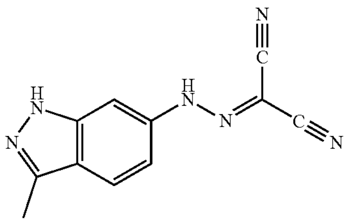 [SMILES: Cc1n[nH]c2cc(NN=C(C#N)C#N)ccc12]
74
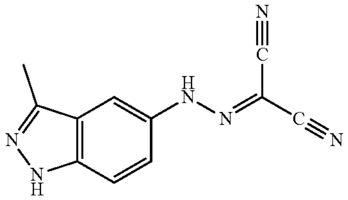 [SMILES: Cc1n[nH]c2ccc(NN=C(C#N)C#N)cc12]
75
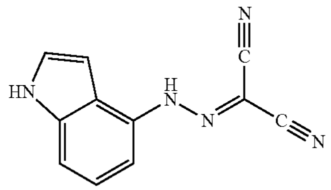 [SMILES: N#CC(C#N)=NNc1cccc2[nH]ccc12]
76
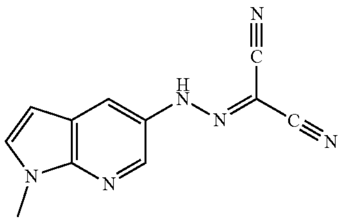 [SMILES: Cn1ccc2cc(NN=C(C#N)C#N)cnc21]

-continued
77
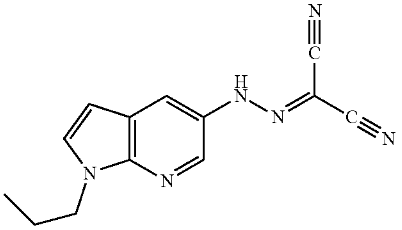 [SMILES: CCCn1ccc2cc(NN=C(C#N)C#N)cnc21]
78
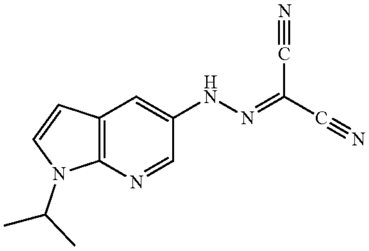 [SMILES: CC(C)n1ccc2cc(NN=C(C#N)C#N)cnc21]
79
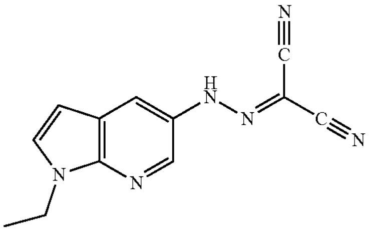 [SMILES: CCn1ccc2cc(NN=C(C#N)C#N)cnc21]
80
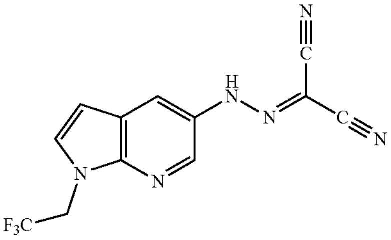 [SMILES: N#CC(C#N)=NNc1cnc2c(ccn2CC(F)(F)F)c1]
81
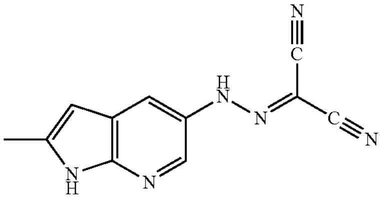 [SMILES: Cc1cc2cc(NN=C(C#N)C#N)cnc2[nH]1]
82
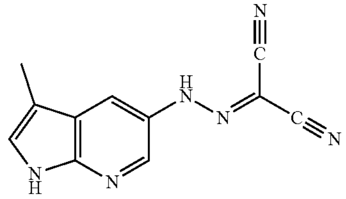 [SMILES: Cc1c[nH]c2ncc(NN=C(C#N)C#N)cc12]
83
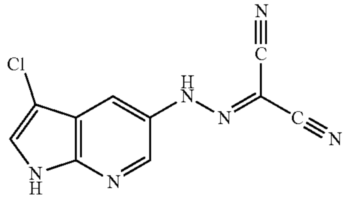 [SMILES: N#CC(C#N)=NNc1cnc2[nH]cc(Cl)c2c1]
-continued
84
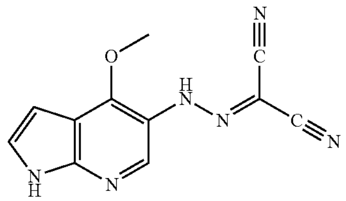 [SMILES: COc1c(NN=C(C#N)C#N)cnc2[nH]ccc12]
85
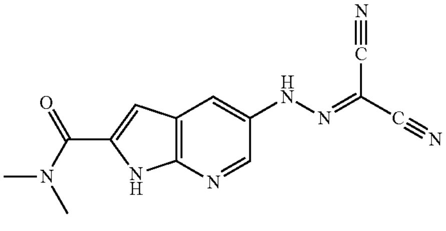 [SMILES: CN(C)C(=O)c1cc2cc(NN=C(C#N)C#N)cnc2[nH]1]
86
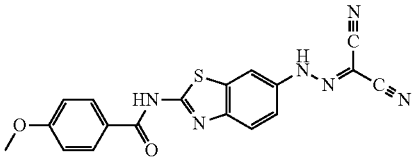 [SMILES: COc1ccc(C(=O)Nc2nc3ccc(NN=C(C#N)C#N)cc3s2)cc1]
87
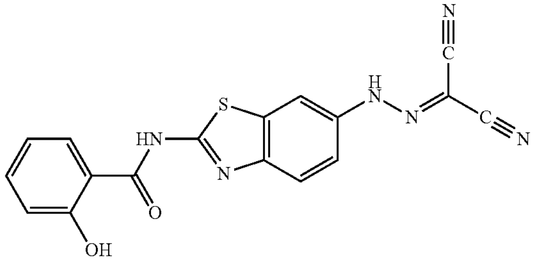 [SMILES: N#CC(C#N)=NNc1ccc2nc(NC(=O)c3ccccc3O)sc2c1]
88
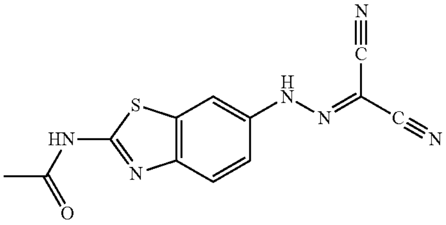 [SMILES: CC(=O)Nc1nc2ccc(NN=C(C#N)C#N)cc2s1]
89
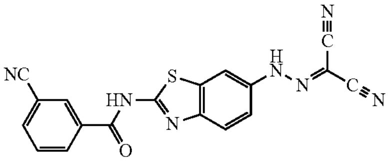 [SMILES: N#CC(C#N)=NNc1ccc2nc(NC(=O)c3cccc(C#N)c3)sc2c1]
90
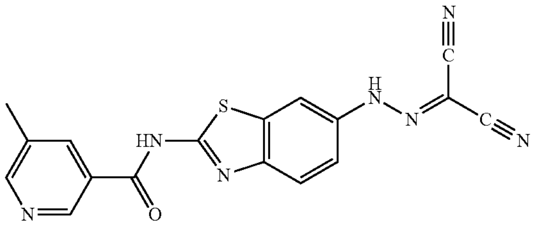 [SMILES: Cc1cncc(C(=O)Nc2nc3ccc(NN=C(C#N)C#N)cc3s2)c1]

-continued
91
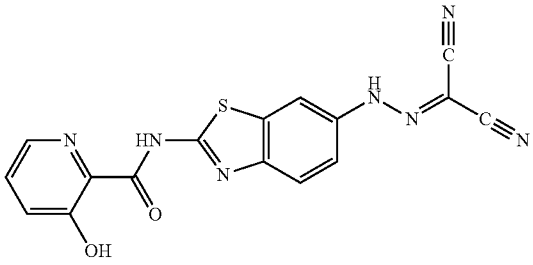 [SMILES: N#CC(C#N)=NNc1ccc2nc(NC(=O)c3ncccc3O)sc2c1]
92
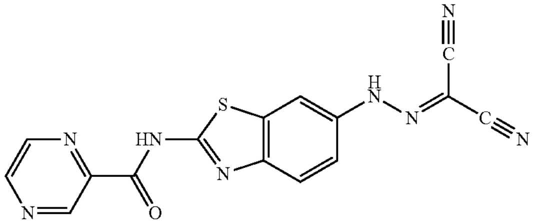 [SMILES: N#CC(C#N)=NNc1ccc2nc(NC(=O)c3cnccn3)sc2c1]
93
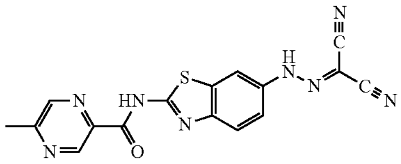 [SMILES: Cc1cnc(C(=O)Nc2nc3ccc(NN=C(C#N)C#N)cc3s2)cn1]
94
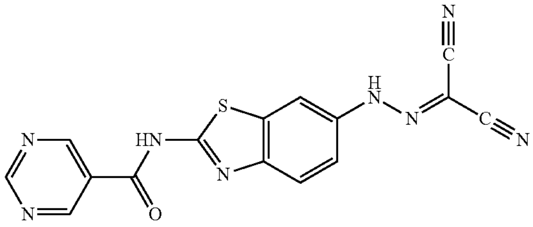 [SMILES: N#CC(C#N)=NNc1ccc2nc(NC(=O)c3cncnc3)sc2c1]
95
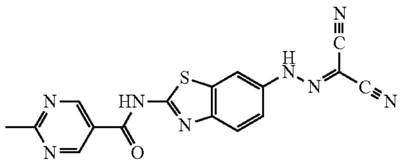 [SMILES: Cc1ncc(C(=O)Nc2nc3ccc(NN=C(C#N)C#N)cc3s2)cn1]
96
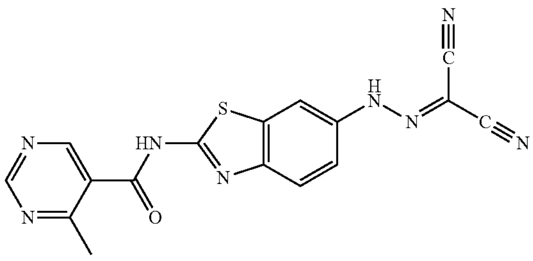 [SMILES: Cc1ncncc1C(=O)Nc1nc2ccc(NN=C(C#N)C#N)cc2s1]
97
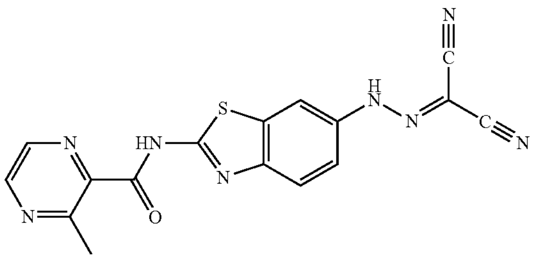 [SMILES: Cc1nccnc1C(=O)Nc1nc2ccc(NN=C(C#N)C#N)cc2s1]
-continued
98
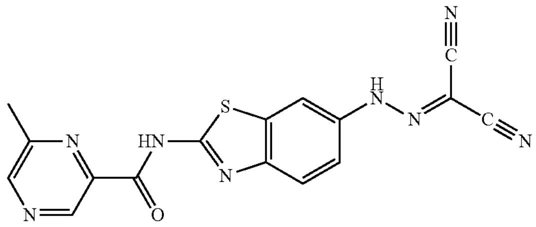 [SMILES: Cc1cncc(C(=O)Nc2nc3ccc(NN=C(C#N)C#N)cc3s2)n1]
99
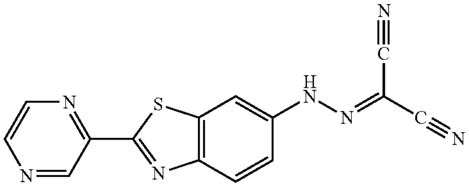 [SMILES: N#CC(C#N)=NNc1ccc2nc(-c3cnccn3)sc2c1]
100
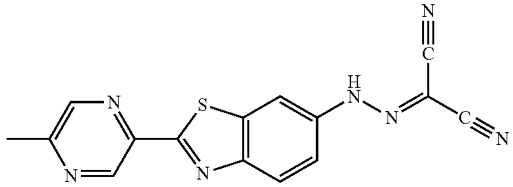 [SMILES: Cc1cnc(-c2nc3ccc(NN=C(C#N)C#N)cc3s2)cn1]
101
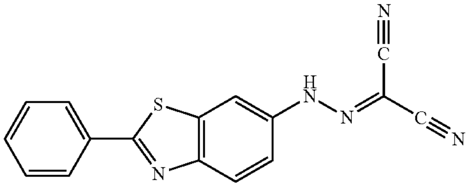 [SMILES: N#CC(C#N)=NNc1ccc2nc(-c3ccccc3)sc2c1]
102
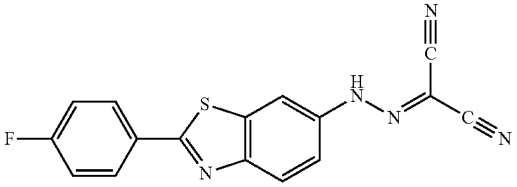 [SMILES: N#CC(C#N)=NNc1ccc2nc(-c3ccc(F)cc3)sc2c1]
103
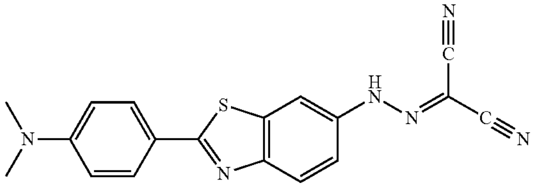 [SMILES: CN(C)c1ccc(-c2nc3ccc(NN=C(C#N)C#N)cc3s2)cc1]
104
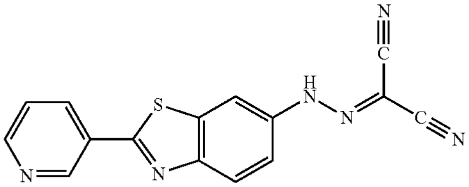
105
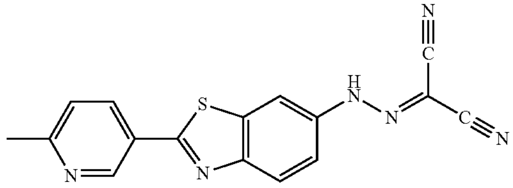

-continued
106
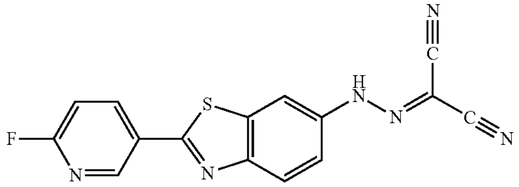 [SMILES: N#CC(C#N)=NNc1ccc2nc(-c3ccc(F)nc3)sc2c1]
107
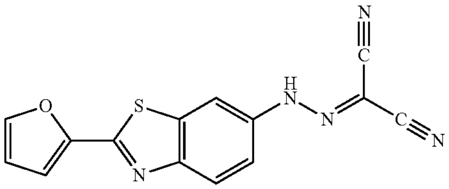 [SMILES: N#CC(C#N)=NNc1ccc2nc(-c3ccco3)sc2c1]
108
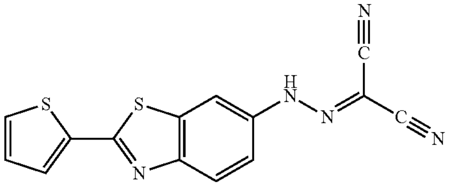 [SMILES: N#CC(C#N)=NNc1ccc2nc(-c3cccs3)sc2c1]
109
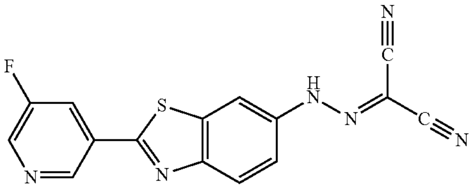 [SMILES: N#CC(C#N)=NNc1ccc2nc(-c3cncc(F)c3)sc2c1]
110
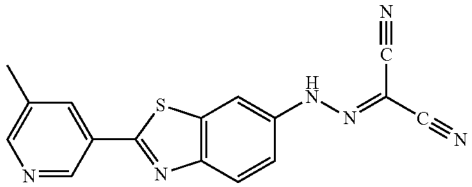 [SMILES: Cc1cncc(-c2nc3ccc(NN=C(C#N)C#N)cc3s2)c1]
111
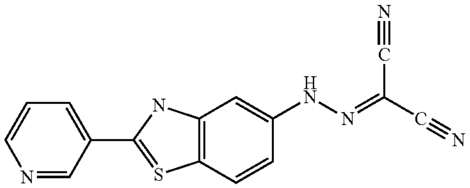
112
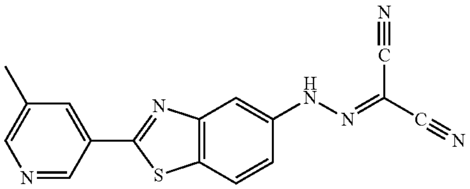 [SMILES: Cc1cncc(-c2nc3cc(NN=C(C#N)C#N)ccc3s2)c1]
113
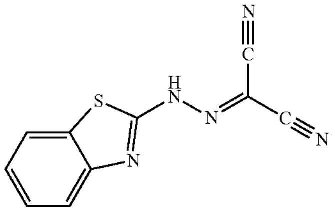 [SMILES: N#CC(C#N)=NNc1nc2ccccc2s1]
-continued
114
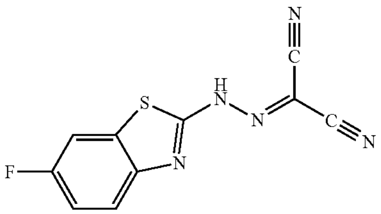 [SMILES: N#CC(C#N)=NNc1nc2ccc(F)cc2s1]
115
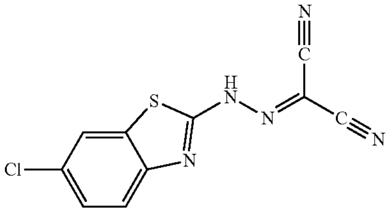 [SMILES: N#CC(C#N)=NNc1nc2ccc(Cl)cc2s1]
116
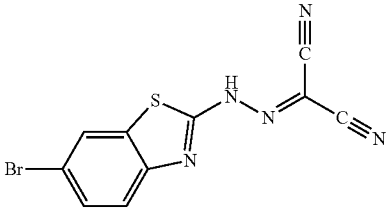
117
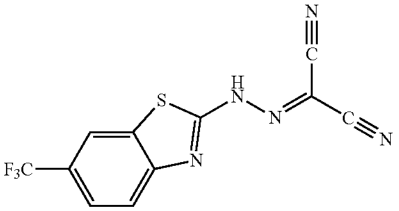 [SMILES: N#CC(C#N)=NNc1nc2ccc(C(F)(F)F)cc2s1]
118
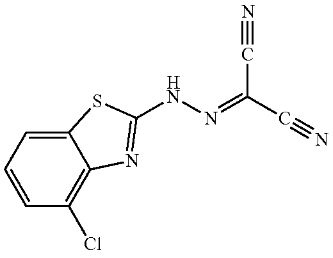 [SMILES: N#CC(C#N)=NNc1nc2c(Cl)cccc2s1]
119
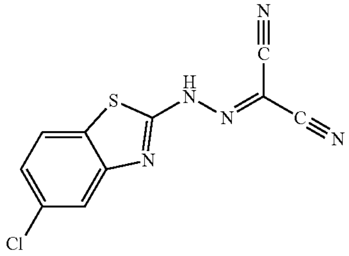 [SMILES: N#CC(C#N)=NNc1nc2cc(Cl)ccc2s1]

-continued
120
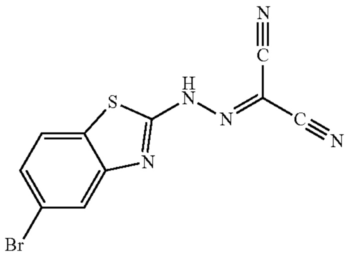
121
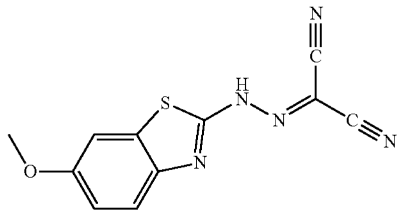 [SMILES: COc1ccc2nc(NN=C(C#N)C#N)sc2c1]
122
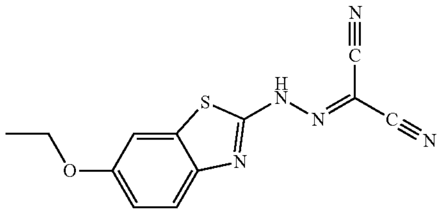 [SMILES: CCOc1ccc2nc(NN=C(C#N)C#N)sc2c1]
123
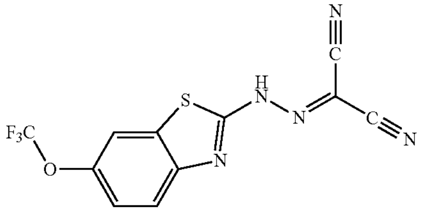 [SMILES: N#CC(C#N)=NNc1nc2ccc(OC(F)(F)F)cc2s1]
124
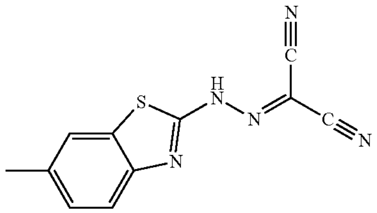 [SMILES: Cc1ccc2nc(NN=C(C#N)C#N)sc2c1]
125
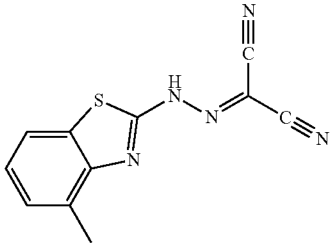 [SMILES: Cc1cccc2sc(NN=C(C#N)C#N)nc12]
-continued
126
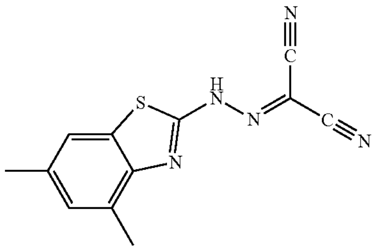 [SMILES: Cc1cc(C)c2nc(NN=C(C#N)C#N)sc2c1]
127
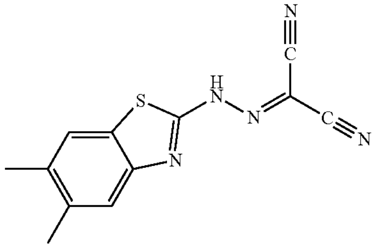 [SMILES: Cc1cc2nc(NN=C(C#N)C#N)sc2cc1C]
128
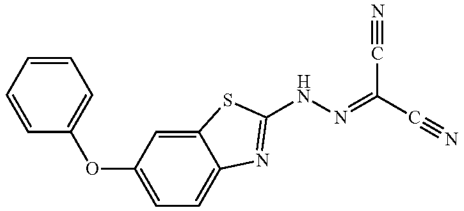 [SMILES: N#CC(C#N)=NNc1nc2ccc(Oc3ccccc3)cc2s1]
129
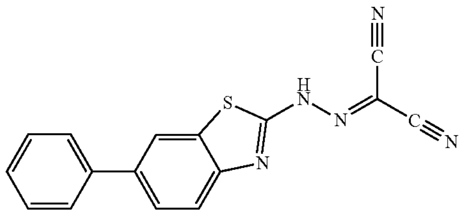 [SMILES: N#CC(C#N)=NNc1nc2ccc(-c3ccccc3)cc2s1]
130
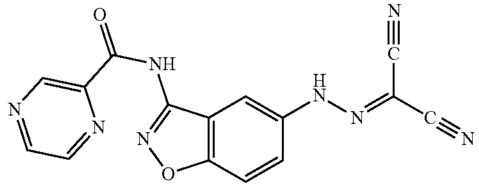 [SMILES: N#CC(C#N)=NNc1ccc2onc(NC(=O)c3cnccn3)c2c1]
131
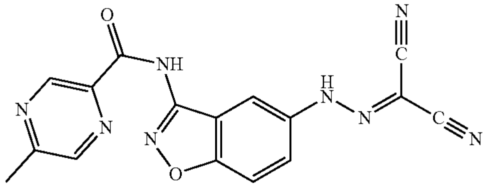 [SMILES: Cc1cnc(C(=O)Nc2noc3ccc(NN=C(C#N)C#N)cc23)cn1]
132
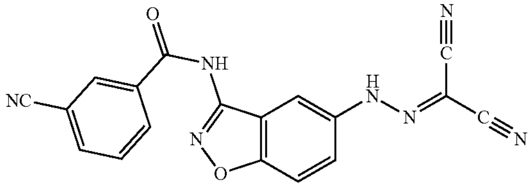 [SMILES: N#CC(C#N)=NNc1ccc2onc(NC(=O)c3cccc(C#N)c3)c2c1]

-continued
133
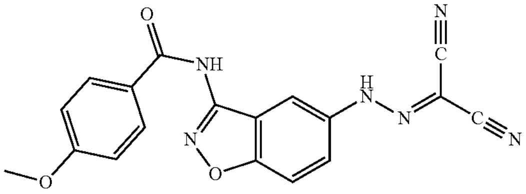 [SMILES: COc1ccc(C(=O)Nc2noc3ccc(NN=C(C#N)C#N)cc23)cc1]
134
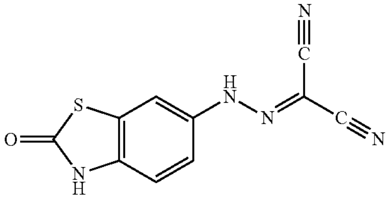 [SMILES: N#CC(C#N)=NNc1ccc2[nH]c(=O)sc2c1]
135
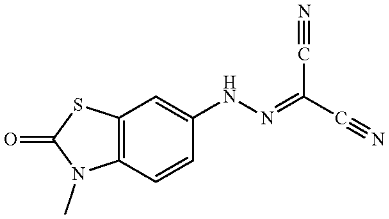 [SMILES: Cn1c(=O)sc2cc(NN=C(C#N)C#N)ccc21]
136
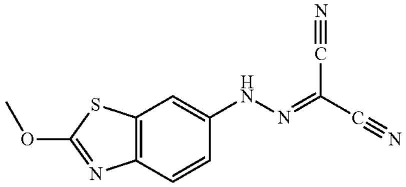 [SMILES: COc1nc2ccc(NN=C(C#N)C#N)cc2s1]
137
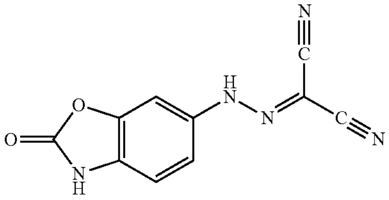
138
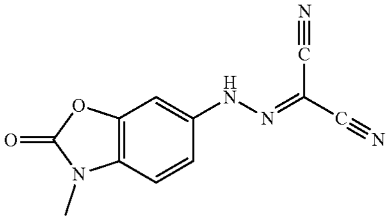 [SMILES: Cn1c(=O)oc2cc(NN=C(C#N)C#N)ccc21]
139
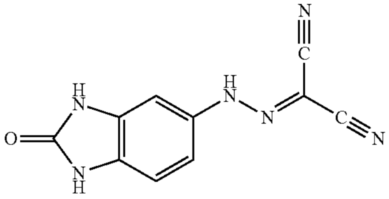 [SMILES: N#CC(C#N)=NNc1ccc2[nH]c(=O)[nH]c2c1]
-continued
140
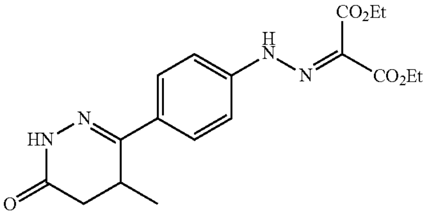 [SMILES: CCOC(=O)C(=NNc1ccc(C2=NNC(=O)CC2C)cc1)C(=O)OCC]
141
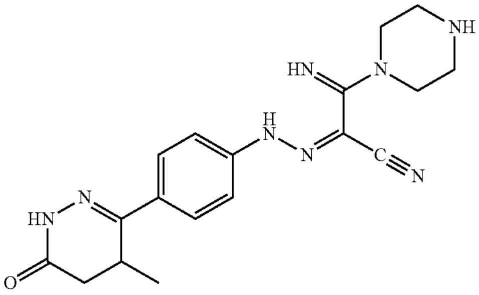 [SMILES: CC1CC(=O)NN=C1c1ccc(N/N=C(/C#N)C(=N)N2CCNCC2)cc1]
142
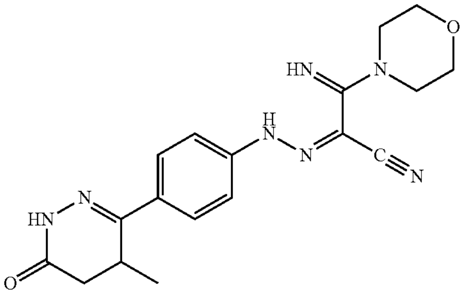 [SMILES: CC1CC(=O)NN=C1c1ccc(N/N=C(/C#N)C(=N)N2CCOCC2)cc1]
143
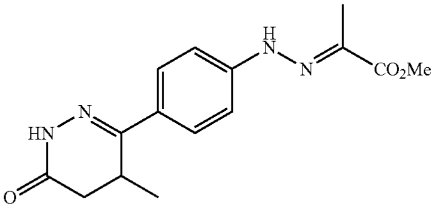 [SMILES: COC(=O)/C(C)=N/Nc1ccc(C2=NNC(=O)CC2C)cc1]
144
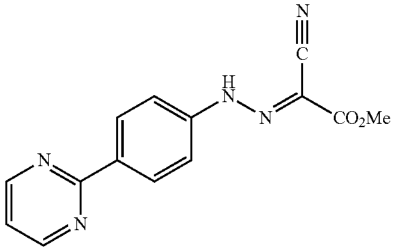 [SMILES: COC(=O)/C(C#N)=N/Nc1ccc(-c2ncccn2)cc1]
145
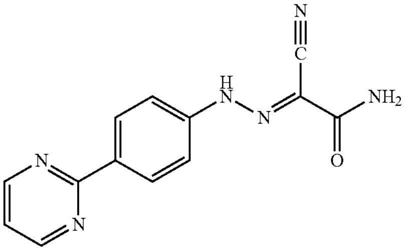 [SMILES: N#C/C(=N\Nc1ccc(-c2ncccn2)cc1)C(N)=O]

-continued
146
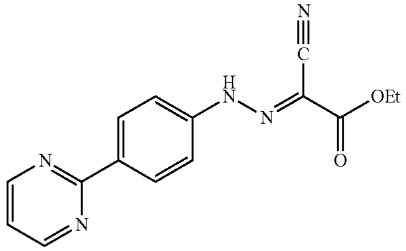 [SMILES: CCOC(=O)/C(C#N)=N/Nc1ccc(-c2ncccn2)cc1]
147
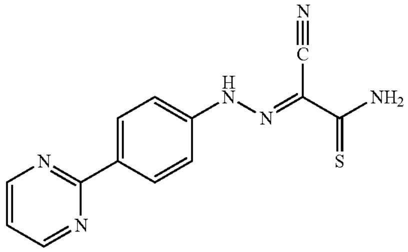 [SMILES: N#C/C(=N\Nc1ccc(-c2ncccn2)cc1)C(N)=S]
148
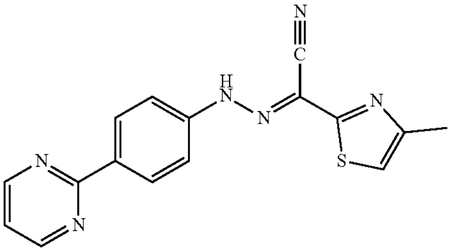 [SMILES: Cc1csc(/C(C#N)=N/Nc2ccc(-c3ncccn3)cc2)n1]
149
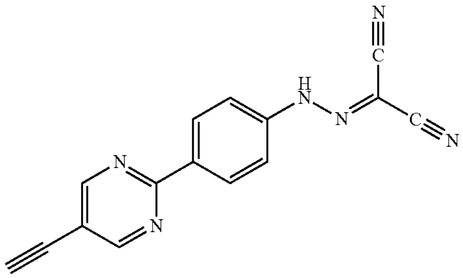 [SMILES: C#Cc1cnc(-c2ccc(NN=C(C#N)C#N)cc2)nc1]
150
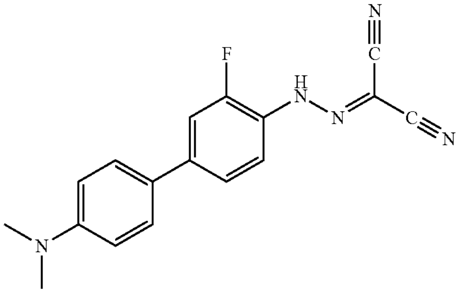 [SMILES: CN(C)c1ccc(-c2ccc(NN=C(C#N)C#N)c(F)c2)cc1]
-continued
151
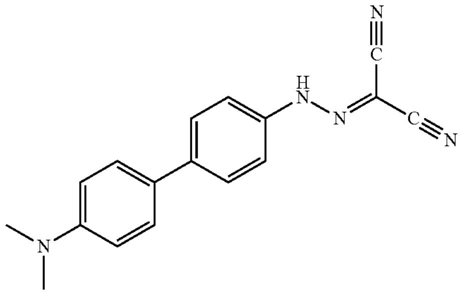 [SMILES: CN(C)c1ccc(-c2ccc(NN=C(C#N)C#N)cc2)cc1]
152
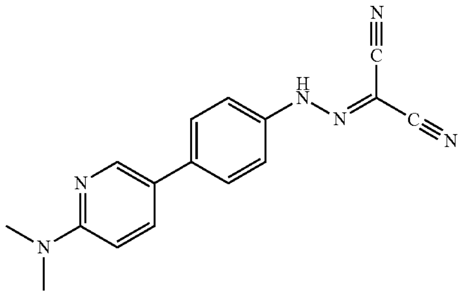 [SMILES: CN(C)c1ccc(-c2ccc(NN=C(C#N)C#N)cc2)cn1]
153
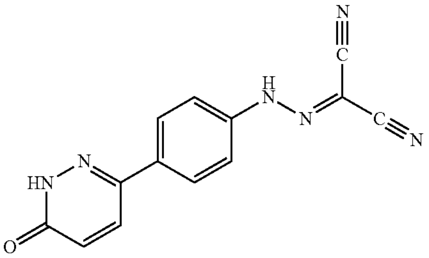 [SMILES: N#CC(C#N)=NNc1ccc(-c2ccc(=O)[nH]n2)cc1]
154
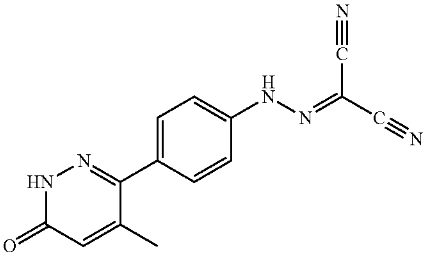 [SMILES: Cc1cc(=O)[nH]nc1-c1ccc(NN=C(C#N)C#N)cc1]
155
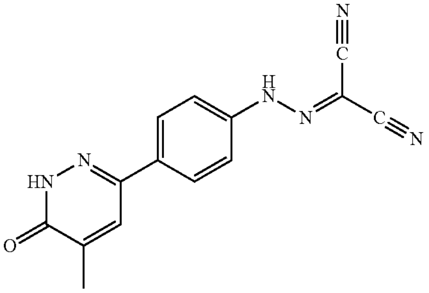 [SMILES: Cc1cc(-c2ccc(NN=C(C#N)C#N)cc2)n[nH]c1=O]

-continued
156
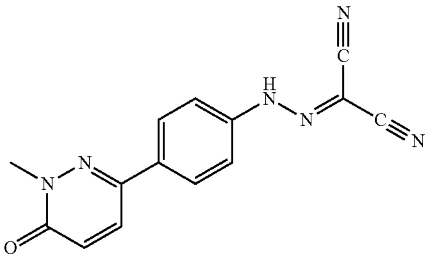 [SMILES: Cn1nc(-c2ccc(NN=C(C#N)C#N)cc2)ccc1=O]
157
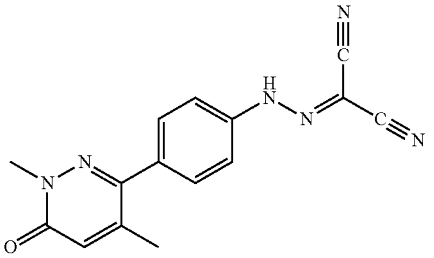 [SMILES: Cc1cc(=O)n(C)nc1-c1ccc(NN=C(C#N)C#N)cc1]
158
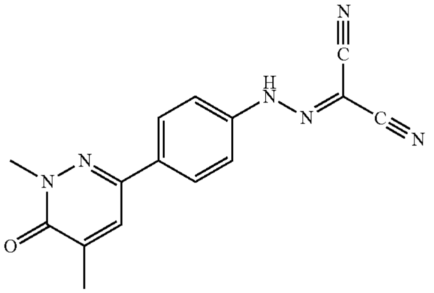 [SMILES: Cc1cc(-c2ccc(NN=C(C#N)C#N)cc2)nn(C)c1=O]
159
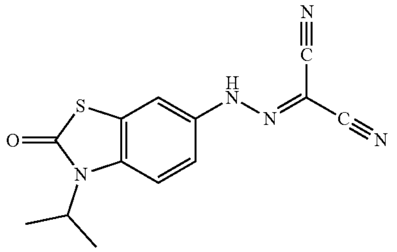 [SMILES: CC(C)n1c(=O)sc2cc(NN=C(C#N)C#N)ccc21]
160
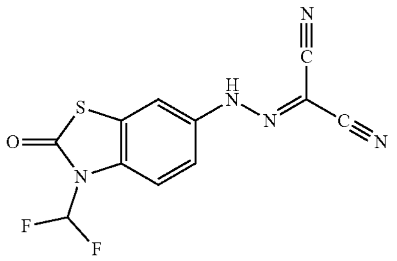 [SMILES: N#CC(C#N)=NNc1ccc2c(c1)sc(=O)n2C(F)F]
161
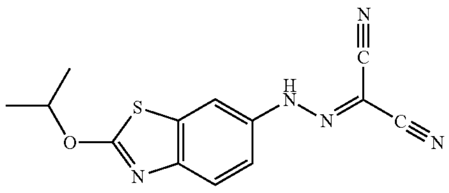 [SMILES: CC(C)Oc1nc2ccc(NN=C(C#N)C#N)cc2s1]
-continued
162
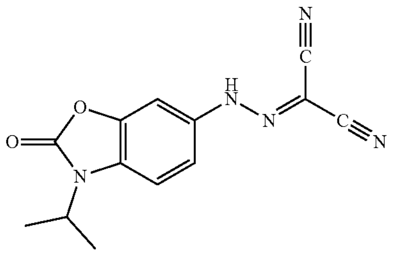
163
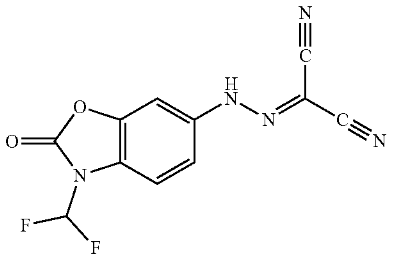
164
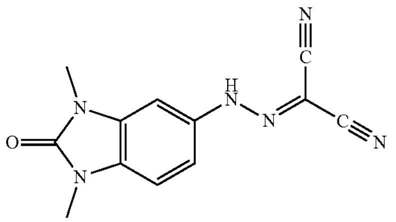 [SMILES: Cn1c(=O)n(C)c2cc(NN=C(C#N)C#N)ccc21]
165
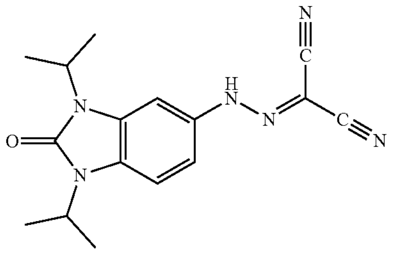 [SMILES: CC(C)n1c(=O)n(C(C)C)c2cc(NN=C(C#N)C#N)ccc21]
166
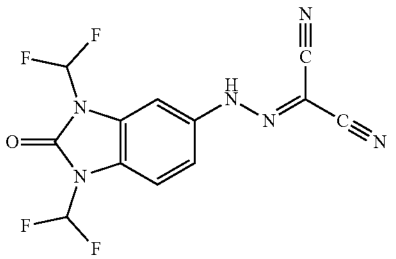 [SMILES: N#CC(C#N)=NNc1ccc2c(c1)n(C(F)F)c(=O)n2C(F)F]
167
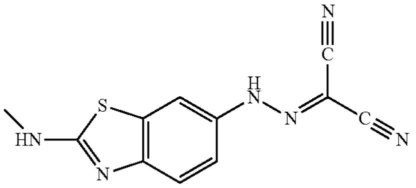 [SMILES: CNc1nc2ccc(NN=C(C#N)C#N)cc2s1]

-continued

168

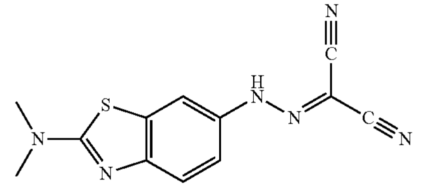 [SMILES: CN(C)c1nc2ccc(NN=C(C#N)C#N)cc2s1]

169

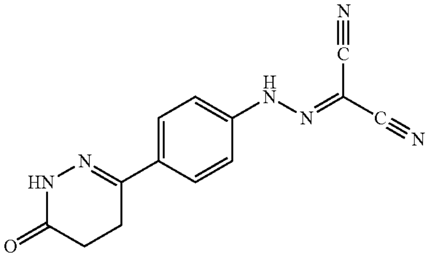 [SMILES: N#CC(C#N)=NNc1ccc(C2=NNC(=O)CC2)cc1]

170

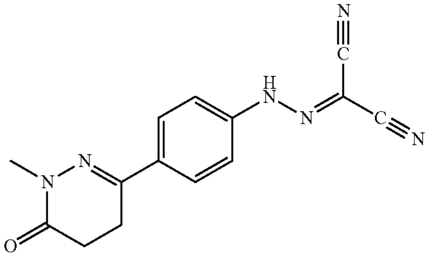 [SMILES: CN1N=C(c2ccc(NN=C(C#N)C#N)cc2)CCC1=O]

171

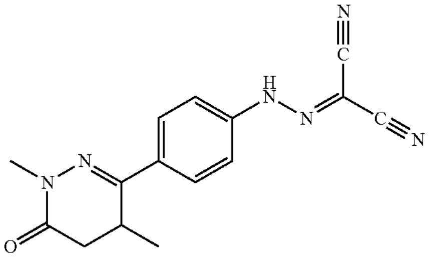 [SMILES: CC1CC(=O)N(C)N=C1c1ccc(NN=C(C#N)C#N)cc1]

Meanwhile, the compound of the present invention may exist in the form of a pharmaceutically acceptable salt. As the salt, an acid salt formed by a pharmaceutically acceptable free acid is useful. As used herein, the term "pharmaceutically acceptable salt" refers to any organic or inorganic addition salt of the compound represented by Formula 1 which is relatively non-toxic and harmless to patients, and side effects caused by this salt do not compromise the beneficial effects of this compound.

An acid addition salt is prepared by a conventional method, for example, by dissolving a compound in an excess amount of an aqueous acid solution and precipitating this solution using a water-miscible organic solvent such as methanol, ethanol, acetone, or acetonitrile. The same molar amounts of the compound and acid or alcohol (for example, glycol monoethyl ether) in water are heated, and subsequently the mixture may be evaporated and dried, or the precipitated salt may be suction-filtered.

In this case, as the free acid, an organic acid or an inorganic acid may be used. As the inorganic acid, hydrochloric acid, phosphoric acid, sulfuric acid, nitric acid, tartaric acid, or the like may be used. As the organic acid, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbon acid, vanillic acid, hydroiodic acid, or the like may be used. However, the present invention is not limited thereto.

Further, a pharmaceutically acceptable metal salt may be made using a base. An alkali metal salt or alkaline earth metal salt is obtained by dissolving the compound in an excess amount of an alkali metal hydroxide or alkaline earth metal hydroxide solution, filtering a non-soluble compound salt, and then evaporating and drying the filtrate. In this case, it is suitable for pharmaceutical use to prepare a sodium, potassium, or calcium salt as the metal salt, but the present invention is not limited thereto. Further, the corresponding silver salt may be obtained by reacting an alkali metal or alkaline earth metal salt with a suitable silver salt (for example, silver nitrate).

Pharmaceutically acceptable salts of the compounds of the present invention comprise salts of acidic or basic groups that may be present in the compounds of Formulas 1 to 5, unless otherwise indicated. For example, pharmaceutically acceptable salts may comprise sodium, calcium, and potassium salts of hydroxy groups, and other pharmaceutically acceptable salts of amino groups may comprise hydrobromide, sulfate, hydrogen sulfate, phosphate, hydrogen phosphate, dihydrogen phosphate, acetate, succinate, citrate, tartrate, lactate, mandelate, methanesulfonate (mesylate), and p-toluenesulfonate (tosylate). These pharmaceutically acceptable salts may be prepared by preparation methods of salts known in the art.

As the salts of the compounds of Formulas 1 to 5 of the present invention, any salt, as a pharmaceutically acceptable salt, may be used without limitation as long as it exhibits pharmacological activity equivalent to the compound of Formula 1, for example, it inhibits the aggregation and/or hyperphosphorylation of tau protein.

Further, the compounds represented by Formulas 1 to 5 according to the present invention comprise, without limitation, pharmaceutically acceptable salts thereof, as well as solvates such as possible hydrates that may be prepared therefrom, and all possible stereoisomers. The solvates and stereoisomers of the compounds represented by Formulas 1 to 5 may be prepared from the compounds represented by Formulas 1 to 5 using a method known in the art.

Moreover, the compounds represented by Formulas 1 to 5 according to the present invention may be prepared in a crystalline or amorphous form, and may be optionally hydrated or solvated if prepared in a crystalline form. In the present invention, compounds containing various amounts of water as well as stoichiometric hydrates of the compounds represented by Formulas 1 to 5 may be provided. The solvates of the compounds represented by Formulas 1 to 5 according to the present invention comprise both stoichiometric solvates and non-stoichiometric solvates.

A second aspect of the present invention provides a method of preparing the compound of Formula 1, comprising the step of reacting sodium nitrite, an amino derivative of $R_2$ ($R_2$—$NH_2$), and

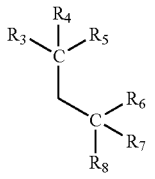

in the presence of acid to form an imine bond.

In the preparation method of the present invention, for reactants used therein, commercially available compounds may be used as purchased, or may be synthesized by exactly performing one or more reactions known in the art or by modifying some reaction conditions of reactions known in the art. For example, the compounds may be synthesized by performing one or more reactions sequentially in consideration of the presence, kind, and position of reactive functional groups and/or hetero elements existing in the skeletal structure, but the present invention is not limited thereto. This process may be similarly applied to the following third to sixth aspects.

A third aspect of the present invention provides a method of preparing the compound of Formula 2, comprising the steps of:

a1) preparing an aniline derivative

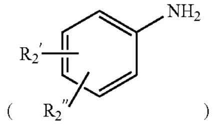

substituted with aryl or heteroaryl unsubstituted or substituted with $R_2$' or $R_2$"; and a2) reacting sodium nitrite, the aniline derivative

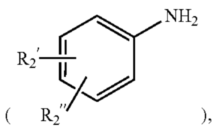

and malononitrile in the presence of acid to form an imine bond.

For example, when $R_1$ in the above Formula is $C_{1-6}$ alkyl, the method may further comprise a step of performing alkylation by reaction with halogenated alkane in the presence of potassium tert-butoxide or sodium hydride in an organic solvent, after the step of forming the imine bond. However, the present invention is not limited thereto, and an alkylation reaction known in the art may be appropriately changed and performed in consideration of the presence or absence of other reactive substituents or hetero elements.

Specifically, the aniline derivative substituted with aryl or heteroaryl unsubstited or substituted with $R_2$' or $R_2$" may be synthesized by reacting a boronic acid pinacol ester derivative of aniline unsubstituted or substituted with $R_2$' with a halogenated aryl or heteroaryl derivative unsubstituted or substituted with $R_2$" using a Pd(II) catalyst in the presence of a base. However, the present invention is not limited thereto, and commercially available compounds may be used as purchased, or may be synthesized by way of a method known in the art.

Further, considering the potential reactivity of substituents and/or hetero elements present in the skeleton of the compound to be synthesized in the reactionconditons, the aniline derivative substituted with aryl or heteroaryl unsubstited or substituted with $R_2$' or $R_2$" may be prepared by reduction of a nitrophenyl derivative containing a nitro group instead of an amine group in the same skeleton using a palladium catalyst activated with carbon under hydrogen gas.

A fourth aspect of the present invention provides a method of preparing the compound of Formula 3, comprising the step of reacting sodium nitrite, a 5- to 14-membered heteroaryl or 5- to 14-membered heterocyclyl derivative containing an amine group, and malononitrile in the presence of acid to form an imine bond.

For example, when the 5- to 14-membered heteroaryl or 5- to 14-membered heterocyclyl contains a nitrogen bondable thereto other than an amine group, it comprises a protecting group at the nitrogen site. The method may further comprise a step of removing the protection group after the step of forming the imine bond.

Further, in consideration of the reactivity of functional groups and/or hetero elements present in the skeleton, the 5- to 14-membered heteroaryl or 5- to 14-membered heterocyclyl may be prepared by reducing a nitrophenyl derivative containing a nitro group instead of an amine group in the same skeleton, but the present invention is not limited thereto.

A fifth aspect of the present invention provides a method of preparing the compound of Formula 4, comprising the steps of:

reacting carboxylic acid of $R_2$" or an anhydride thereof with

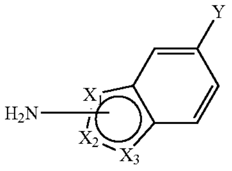

(here, Y is an unprotected or protected amine or nitro group) to form an amide bond; and reacting sodium nitrite, a heterocycle derivative comprising $R_2$" connected to a carboxamido group obtained from the previous step, and malononitrile in the presence of acid to form an imine bond.

In this case, when Y is a protected amine group or nitro group, the method may further comprise a step of converting the protected amine group or nitro group into an amine group before the step of forming the imine group.

A sixth aspect of the present invention provides a method of preparing the compound of Formula 5, comprising the steps of:

reacting sodium nitrite, an amino derivative of $R_2$ ($R_2$—$NH_2$), and

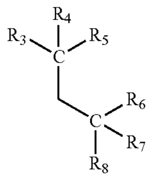

to form an imine bond; and adjusting the pH of the reaction solution to 5 to 7 using a base.

A seventh aspect of the present invention provides a composition for inhibiting the aggregation of tau protein comprising the compound of the present invention as an active ingredient.

An eighth aspect of the present invention is to provide a composition for inhibiting the hyperphosphorylation of tau protein comprising the compound of the present invention as an active ingredient.

A ninth aspect of the present invention is to provide a pharmaceutical composition for preventing or treating diseases caused by the aggregation or hyperphosphorylation of tau protein comprising the compound of the present invention as an active ingredient.

In specific embodiments of the present invention, a total of 171 compounds, numbered 1 to 171 and represented by Formula 1, were newly synthesized, and the effects of inhibiting the aggregation and hyperphosphorylation of tau protein thereof were confirmed. Moreover, in order to confirm the possibility of use as a pharmaceutical composition, it was confirmed that these compounds do not exhibit toxicity to cells.

As used herein, the term "prevention" refers to any action that inhibits or delays the occurrence, spread, and recurrence of a disease induced by the aggregation or hyperphosphorylation of tau protein by the administration of the pharmaceutical composition of the present invention, and the term "treatment" refers to any action in which symptoms of the disease are improved or beneficially changed by the administration of the pharmaceutical composition of the present invention.

As described above, since the compound of the present invention not only inhibits aggregation or hyperphosphorylation of tau protein, but also does not exhibit toxicity to cells, the pharmaceutical composition containing this compound as an active ingredient may be used for the prevention or treatment of diseases caused by aggregation or hyperphosphorylation of tau protein. The disease caused by aggregation or hyperphosphorylation of tau protein to which the pharmaceutical composition of the present invention may be applied may be Alzheimer's disease, Parkinson's disease, vascular dementia, acute stroke, trauma, cerebrovascular disease, brain cord trauma, spinal cord trauma, peripheral neuropathy, retinopathy, glaucoma, or tauopathy. Non-limiting examples of the tauopathy may comprise chronic traumatic encephalopathy (CTE), primary age-related tauopathy, progressive supranuclear palsy, corticobasal degeneration, Pick's disease, argyrophilic grain disease (AGD), frontotemporal dementia (FTD), Parkinsonism linked to chromosome 17, Lytico-bodig disease (Parkinsonism-dementia complex of Guam), ganglioglioma, gangliocytoma, meningioangiomatosis, postencephalitic Parkinsonism, subacute sclerosing panencephalitis, lead encephalopathy, tuberous sclerosis, pantothenate kinase-associated neurodegeneration, lipofuscinosis, and traumatic brain injury.

For example, the composition of the present invention may further comprise a pharmaceutically acceptable carrier, a diluent, or an excipient, may be formulated and used in various forms such as oral formulations such as powders, granules, tablets, capsules, suspensions, emulsions, syrups, aerosols, and injection drugs of sterile injection solutions according to a general method for each purpose of use, and may be administered orally, or may be administered through various routes comprising intravenous, intraperitoneal, subcutaneous, rectal, and topical administrations. Examples of the suitable carrier, expient, or diluent comprised in this composition may comprise lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil. The composition of the present invention may further comprise a filler, an anti-aggregating agent, a lubricant, a wetting agent, a flavoring agent, an emulsifying agent, a preservative, and the like.

Solid preparations for oral administration comprise tablets, pills, powders, granules, capsules, and the like, and such a solid preparation is formulated by mixing one or more excipients, such as starch, calcium carbonate, sucrose, lactose, and gelatin with the composition. Meanwhile, in addition to a simple excipient, a lubricant such as magnesium stearate or talc may be used.

As the oral liquid formulation, a suspension, an anti-solution agent, an emulsion, a syrup, and the like may be exemplified, and the oral liquid formulation may comprise various excipients, such as a wetting agent, a sweetening agent, a fragrance, and a preservative in addition to water and liquid paraffin, which are commonly used as a simple diluent.

Preparations for parenteral administration comprise an aqueous solvent, a non-aqueous solvent, a suspension agent, an emulsifying agent, a lyophilized preparation, and a suppository, which are sterilized.

As the non-aqueous solvent or the suspension agent, propylene glycol, polyethylene glycol, plant oil such as olive oil, injectable ester such as ethyloleate, or the like may be used. As a base of the suppository, witepsol, macrogol, twin 61, cacao oil, laurin oil, glycerogelatin, or the like may be used. Meanwhile, injectables may comprise conventional additives such as a solubilizing agent, an isotonic agent, a suspension agent, an emulsifying agent, a stabilizing agent, and a preservative.

The formulation may be prepared by a conventional mixing, granulating, or coating method, and may contain an active ingredient in an amount of about 0.1 wt % to 75 wt %, preferably about 0.1 wt % to 50 wt %. The unit formulation for a mammal weighing about 50 kg to 70 kg contains about 10 mg to 200 mg of an active ingredient.

In this case, the composition of the present invention is administered in a pharmaceutically effective amount. As used herein, the term "pharmaceutically effective amount" refers to an amount sufficient to treat a disease at a reasonable benefit/risk ratio applicable to medical treatment and not cause side effects, and the level of the effective amount may be determined depending on patient's health status, type of disease, severity, activity of drug, sensitivity to drug, administration method, administration time, administration route, excretion rate, treatment period, factors comprising drugs used in combination or concurrently, and other factors well known in the medical field. The composition of the present invention may be administered as an individual therapeutic agent or administered in combination with other therapeutic agents, may be administered sequentially or simultaneously with a conventional therapeutic agent, and may be administered in a single dose or multiple doses. It is important to administer an amount capable of obtaining the maximum effect in a minimum amount without side effects in consideration of all of the above factors, which may be easily determined by those skilled in the art.

For example, since the administration amount may increase or decrease depending on administration route, disease severity, sex, weight, age, and the like, the administration amount does not limit the scope of the present invention in any way.

The preferred administration amount of the compound of the present invention varies depending on the condition and weight of a patient, the degree of disease, the form of drug, and the route and duration of administration, but may be appropriately selected by those skilled in the art. However, for a desired effect, the compound of the present invention may be administered in an amount of 0.0001 mg/kg to 100 mg/kg (body weight), preferably, 0.001 mg/kg to 100 mg/kg (body weight) per day. The compound may be administered once a day or may be divided and administered through an oral or parenteral route.

A tenth aspect of the present invention is to provide a method for preventing or treating diseases caused by the aggregation or hyperphosphorylation of tau protein, the method comprising the step of administering the pharmaceutical composition of the present invention to a subject in need thereof.

As used herein, the term "subject" refers to any animal comprising monkeys, cows, horses, sheep, pigs, chickens, turkeys, quails, cats, dogs, mice, rabbits, and guinea pigs in addition to humans, which have developed or may develop diseases caused by the aggregation or hyperphosphorylation of tau protein. The diseases may be effectively prevented or treated by administering the pharmaceutical composition of the present invention to the subject. Further, since the pharmaceutical composition of the present invention exhibits a therapeutic effect by inhibiting the aggregation or hyperphosphorylation of tau protein, a synergistic effect may be exhibited by administering this composition in combination with a conventional therapeutic agent.

As used herein, the term "administration" refers to providing a predetermined substance to a patient by any suitable method, and the administration route of the composition of the present invention may be administered through any general route as long as it can reach target tissues. The composition may be administered through intraperitoneal administration, intravenous administration, intramuscular administration, subcutaneous administration, intradermal administration, oral administration, topical administration, intranasal administration, intrapulmonary administration, or rectal administration, but the present invention is not limited thereto. Meanwhile, the pharmaceutical composition of the present invention may be administered by any device capable of moving an active substance to a target cell. Preferred administrations and formulations comprise intravenous injection drugs, subcutaneous injection drugs, intradermal injection drugs, intramuscular injection drugs, and dropwise injection drugs. The injection drugs may be prepared using an aqueous solvent such as a physiological saline solution or Ringer's solution, or a non-aqueous solvent such as plant oil, higher fatty acid ester (for example, ethyl oleate), or alcohol (for example, ethanol, benzyl alcohol, propylene glycol, or glycerin), and may comprise a pharmaceutical carrier such as a stabilizing agent for preventing denaturing (for example, ascorbic acid, sodium hydrogen sulfite, sodium pyrosulfite, BHA, tocopherol, or EDTA), an emulsifying agent, a buffering agent for pH control, or a preservative for inhibiting the growth of microorganisms (for example, phenylmercury nitrate, thimerosal, benzalkonium chloride, phenol, cresol, or benzyl alcohol).

EXAMPLES

Hereinafter, the present invention will be described in more detail with reference to Examples and Experimental Examples. However, these Examples and Experimental Examples are only illustrative of the present invention, and the scope of the present invention is not limited to these Examples and Experimental Examples.

Example 1: Preparation of (4-(pyrimidin-2-yl)phenyl)carbonohydrazonoyl dicyanide (Compound 1)

Step 1-1: Preparation of 4-(pyrimidin-2-yl)aniline

2-Bromopyrimidine (175 mg, 1.10 mmol) and 4-aminophenylboronic acid pinacol ester (4-(4,4,5,5-tetramethyl-1,3,2-dioxaborolan-2-yl)aniline) (200 mg, 0.91 mmol) were dissolved in 15 mL of a 1,4-dioxane solution in the presence of nitrogen, and then $Pd(PPh_3)_2Cl_2$ (63 mg, 0.09 mmol) and a 1.0 M aqueous sodium carbonate solution (3.64 mL, 3.64 mmol) were added to obtain a reaction mixture. The reaction mixture was stirred at 80° C. for 12 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 115 mg (74% yield) of the title compound.

Step 1-2: Preparation of (4-(pyrimidin-2-yl)phenyl)carbonohydrazonoyl dicyanide 4-(Pyrimidin-2-yl)aniline (50 mg, 0.29 mmol) prepared according to step 1-1 and sodium nitrite (24 mg, 0.35 mmol) were dissolved in ethanol (2.5 mL) in the presence of nitrogen, and then a 1.0 M aqueous hydrochloric acid solution (0.73 mL, 0.73 mmol) was added to obtain a reaction mixture. The reaction mixture was stirred at 0° C. for 1 hour to form a diazonium salt. After the diazonium salt was formed, malononitrile (23 mg, 0.35 mmol) was added, followed by stirring at room temperature for 5 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 57 mg (79% yield) of the title compound.

Example 2: Preparation of (4-(5-fluoropyrimidin-2-yl)phenyl)carbonohydrazonoyl dicyanide (Compound 2)

Step 2-1: Preparation of 4-(5-fluoropyrimidin-2-yl)aniline 71 mg (41% yield) of the title compound was obtained by performing a reaction in the same manner as in step 1-1 of Example 1, except that 2-chloro-5-fluoropyrimidine (1.10 mmol) was used instead of 2-bromopyrimidine.

Step 2-2: Preparation of (4-(5-fluoropyrimidin-2-yl)phenyl)carbonohydrazonoyl dicyanide 30 mg (43% yield) of the title compound was obtained by performing a reaction in the same manner as in step 1-2 of Example 1, except that 4-(5-fluoropyrimidin-2-yl)aniline was used instead of 4-(pyrimidin-2-yl)aniline.

Example 3: Preparation of (4-(5-fluoro-4-methylpyrimidin-2-yl)phenyl)carbonohydrazonoyl dicyanide (Compound 3)

Step 3-1: Preparation of 4-(5-fluoro-4-methylpyrimidin-2-yl)aniline 139 mg (75% yield) of the title compound was obtained by performing a reaction in the same manner as in step 1-1 of Example 1, except that 2-chloro-5-fluoro-4-methylpyrimidine (1.10 mmol) was used instead of 2-bromopyrimidine.

Step 3-2: Preparation of (4-(5-fluoro-4-methylpyrimidin-2-yl)phenyl)carbonohydrazonoyl dicyanide 40 mg (29% yield) of the title compound was obtained by performing a reaction in the same manner as in step 1-2 of Example 1, except that 4-(5-fluoro-4-methylpyrimidin-2-yl)aniline was used instead of 4-(pyrimidin-2-yl)aniline.

Example 4: Preparation of (4-(5-methylpyrimidin-2-yl)phenyl)carbonohydrazonoyl dicyanide (Compound 4)

Step 4-1: Preparation of 4-(5-methylpyrimidin-2-yl)aniline 65 mg (39% yield) of the title compound was obtained by performing a reaction in the same manner as in step 1-1 of Example 1, except that 2-chloro-5-methylpyrimidine (1.10 mmol) was used instead of 2-bromopyrimidine.

Step 4-2: Preparation of (4-(5-methylpyrimidin-2-yl)phenyl)carbonohydrazonoyl dicyanide 35 mg (50% yield) of the title compound was obtained by performing a reaction in the same manner as in step 1-2 of Example 1, except that 4-(5-methylpyrimidin-2-yl)aniline was used instead of 4-(pyrimidin-2-yl)aniline.

Example 5: Preparation of 4-(5-ethylpyrimidin-2-yl)phenyl)carbonohydrazonoyl dicyanide (Compound 5)

Step 5-1: Preparation of 4-(5-ethylpyrimidin-2-yl)aniline 169 mg (93% yield) of the title compound was obtained by performing a reaction in the same manner as in step 1-1 of Example 1, except that 2-chloro-5-ethylpyrimidine (1.10 mmol) was used instead of 2-bromopyrimidine.

Step 5-2: Preparation of (4-(5-ethylpyrimidin-2-yl)phenyl)carbonohydrazonoyl dicyanide 35 mg (25% yield) of the title compound was obtained by performing a reaction in the same manner as in step 1-2 of Example 1, except that 4-(5-ethylpyrimidin-2-yl)aniline was used instead of 4-(pyrimidin-2-yl)aniline.

Example 6: Preparation of (4-(4-ethylpyrimidin-2-yl)phenyl)carbonohydrazonoyl dicyanide (Compound 6)

Step 6-1: Preparation of 4-(4-ethylpyrimidin-2-yl)aniline 169 mg (93% yield) of the title compound was obtained by performing a reaction in the same manner as in step 1-1 of Example 1, except that 2-chloro-4-ethylpyrimidine (1.10 mmol) was used instead of 2-bromopyrimidine.

Step 6-2: Preparation of (4-(4-ethylpyrimidin-2-yl)phenyl)carbonohydrazonoyl dicyanide 80 mg (66% yield) of the title compound was obtained by performing a reaction in the same manner as in step 1-2 of Example 1, except that 4-(4-ethylpyrimidin-2-yl)aniline was used instead of 4-(pyrimidin-2-yl)aniline.

Example 7: Preparation of (4-(5-chloropyrimidin-2-yl)carbonohydrazonoyl dicyanide (Compound 7)

Step 7-1: Preparation of 4-(5-chloropyrimidin-2-yl)aniline 67 mg (36% yield) of the title compound was obtained by performing a reaction in the same manner as in step 1-1 of Example 1, except that 2-chloro-5-chloropyrimidine (1.10 mmol) was used instead of 2-bromopyrimidine.

Step 7-2: Preparation of 4-(5-chloropyrimidin-2-yl)phenyl)carbonohydrazonoyl dicyanide 30 mg (16% yield) of the title compound was obtained by performing a reaction in the same manner as in step 1-2 of Example 1, except that 4-(5-chloropyrimidin-2-yl)aniline was used instead of 4-(pyrimidin-2-yl)aniline.

Example 8: Preparation of (4-(5-methoxypyrimidin-2-yl)-phenyl)carbonohydrazonoyl dicyanide (Compound 8)

Step 8-1: Preparation of 4-(5-methoxypyrimidin-2-yl)aniline 67 mg (36% yield) of the title compound was obtained by performing a reaction in the same manner as in step 1-1 of Example 1, except that 2-chloro-5-methoxypyrimidine (1.10 mmol) was used instead of 2-bromopyrimidine.

Step 8-2: Preparation of (4-(5-methoxypyrimidin-2-yl)phenyl)carbonohydrazonoyl dicyanide 26 mg (30% yield) of the title compound was obtained by performing a reaction in the same manner as in step 1-2 of Example 1, except that 4-(5-methoxypyrimidin-2-yl)aniline was used instead of 4-(pyrimidin-2-yl)aniline.

Example 9: Preparation of (4-(2,4-dimethylthiazol-5-yl)phenyl)carbonohydrazonoyl dicyanide (Compound 9)

Step 9-1: Preparation of 4-(2,4-dimethylthiazol-5-yl)aniline 48 mg (26% yield) of the title compound was obtained by performing a reaction in the same manner as in step 1-1 of Example 1, except that 5-bromo-2,4-dimethylthiazole (1.10 mmol) was used instead of 2-bromopyrimidine.

Step 9-2: Preparation of (4-(2,4-dimethylthiazol-5-yl)phenyl)carbonohydrazonoyl dicyanide 55 mg (93% yield) of the title compound was obtained by performing a reaction in the same manner as in step 1-2 of Example 1, except that 4-(2,4-dimethylthiazol-5-yl)aniline was used instead of 4-(pyrimidin-2-yl)aniline.

Example 10: Preparation of (4-(pyridin-2-yl)phenyl)carbonohydrazonoyl dicyanide (Compound 10)

Step 10-1: Preparation of 4-(pyridin-2-yl)aniline 101 mg (65% yield) of the title compound was obtained by performing a reaction in the same manner as in step 1-1 of Example 1, except that 2-bromopyridine (1.10 mmol) was used instead of 2-bromopyrimidine.

Step 10-2: Preparation of (4-(pyridin-2-yl)phenyl)carbonohydrazonoyl dicyanide 18 mg (25% yield) of the title compound was obtained by performing a reaction in the same manner as in step 1-2 of Example 1, except that 4-(pyridin-2-yl)aniline was used instead of 4-(pyrimidin-2-yl)aniline.

Example 11: Preparation of (4-(2-methylthiazol-5-yl)phenyl)carbonohydrazonoyl dicyanide (Compound 11)

Step 11-1: Preparation of 4-(2-methylthiazol-5-yl)aniline 112 mg (57% yield) of the title compound was obtained by performing a reaction in the same manner as in step 1-1 of Example 1, except that 5-bromo-2-methylthiazole (1.10 mmol) was used instead of 2-bromopyrimidine.

Step 11-2: Preparation of (4-(2-methylthiazol-5-yl)phenyl)carbonohydrazonoyl dicyanide 11 mg (16% yield) of the title compound was obtained by performing a reaction in the same manner as in step 1-2 of Example 1, except that 4-(2-methylthiazol-5-yl)aniline was used instead of 4-(pyrimidin-2-yl)aniline.

Example 12: Preparation of (4-(4-methylthiazol-5-yl)phenyl)carbonohydrazonoyl dicyanide (Compound 12)

Step 12-1: Preparation of 4-(4-methylthiazol-5-yl)aniline 133 mg (76% yield) of the title compound was obtained by performing a reaction in the same manner as in step 1-1 of Example 1, except that 5-bromo-4-methylthiazole (1.10 mmol) was used instead of 2-bromopyrimidine.

Step 12-2: Preparation of (4-(4-methylthiazol-5-yl)phenyl)carbonohydrazonoyl dicyanide 62 mg (89% yield) of the title compound was obtained by performing a reaction in the same manner as in step 1-2 of Example 1, except that 4-(4-methylthiazol-5-yl)aniline was used instead of 4-(pyrimidin-2-yl)aniline.

Example 13: Preparation of biphenyl-4-ylcarbonohydrazonoyl dicyanide (Compound 13)

Step 13-1: Preparation of biphenyl-4-amine 109 mg (70% yield) of the title compound was obtained by performing a reaction in the same manner as in step 1-1 of Example 1, except that bromobenzene (1.10 mmol) was used instead of 2-bromopyrimidine.

Step 13-2: Preparation of biphenyl-4-ylcarbonohydrazonoyl dicyanide 29 mg (38% yield) of the title compound was obtained by performing a reaction in the same manner as in step 1-2 of Example 1, except that biphenyl-4-amine was used instead of 4-(pyrimidin-2-yl)aniline.

Example 14: Preparation of (4'-methylbiphenyl-4-yl)carbonohydrazonoyl dicyanide (Compound 14)

Step 14-1: Preparation of 4'-methylbiphenyl-4-amine

The title compound was obtained by performing a reaction in the same manner as in step 1-1 of Example 1, except that 1-bromo-4-methylbenzene (1.10 mmol) was used instead of 2-bromopyrimidine.

Step 14-2: Preparation of (4'-methylbiphenyl-4-yl)carbonohydrazonoyl dicyanide 48 mg (23% yield) of the title compound was obtained by performing a reaction in the same manner as in step 1-2 of Example 1, except that 4'-methylbiphenyl-4-amine was used instead of 4-(pyrimidin-2-yl)aniline.

Example 15: Preparation of (4-(pyridin-3-yl)phenyl)carbonohydrazonoyl dicyanide (Compound 15)

Step 15-1: Preparation of 4-(pyridin-3-yl)aniline 367 mg (23% yield) of the title compound was obtained by performing a reaction in the same manner as in step 1-1 of Example 1, except that 3-bromopyridine (10.95 mmol) was used instead of 2-bromopyrimidine.

Step 15-2: Preparation of (4-(pyridin-3-yl)phenyl)carbonohydrazonoyl dicyanide 533 mg (100% yield) of the title compound was obtained by performing a reaction in the same manner as in step 1-2 of Example 1, except that 4-(pyridin-3-yl)aniline was used instead of 4-(pyrimidin-2-yl)aniline.

Example 16: Preparation of (4-(pyridin-4-yl)phenyl)carbonohydrazonoyl dicyanide (Compound 16)

Step 16-1: Preparation of 4-(pyridin-4-yl)aniline 70 mg (32% yield) of the title compound was obtained by performing a reaction in the same manner as in step 1-1 of Example 1, except that 4-bromopyridine hydrochloride (1.53 mmol) was used instead of 2-bromopyrimidine.

Step 16-2: Preparation of (4-(pyridin-4-yl)phenyl)carbonohydrazonoyl dicyanide 9 mg (9% yield) of the title compound was obtained by performing a reaction in the same manner as in step 1-2 of Example 1, except that 4-(pyridin-4-yl)aniline was used instead of 4-(pyrimidin-2-yl)aniline.

Example 17: Preparation of (4-(pyridazin-3-yl)phenyl)carbonohydrazonoyl dicyanide (Compound 17)

Step 17-1: Preparation of 4-(pyridazin-3-yl)aniline 76 mg (84% yield) of the title compound was obtained by performing a reaction in the same manner as in step 1-1 of Example 1, except that 3-bromopyridazine (0.64 mmol) was used instead of 2-bromopyrimidine.

Step 17-2: Preparation of (4-(pyridazin-3-yl)phenyl)carbonohydrazonoyl dicyanide 42 mg (38% yield) of the title compound was obtained by performing a reaction in the same manner as in step 1-2 of Example 1, except that 4-(pyridazin-3-yl)aniline was used instead of 4-(pyrimidin-2-yl)aniline.

Example 18: Preparation of (4-(5-methylthiazol-2-yl)phenyl)carbonohydrazonoyl dicyanide (Compound 18)

Step 18-1: Preparation of 4-(5-methylthiazol-2-yl)aniline 88 mg (68% yield) of the title compound was obtained by performing a reaction in the same manner as in step 1-1 of Example 1, except that 2-bromo-5-methylthiazole (0.69 mmol) was used instead of 2-bromopyrimidine.

Step 18-2: Preparation of (4-(5-methylthiazol-2-yl)phenyl)carbonohydrazonoyl dicyanide 30 mg (42% yield) of the title compound was obtained by performing a reaction in the same manner as in step 1-2 of Example 1, except that 4-(5-methylthiazol-2-yl)aniline was used instead of 4-(pyrimidin-2-yl)aniline.

Example 19: Preparation of ethyl 2-(4-(2-(dicyanomethylene)hydrazinyl)phenyl) thiazole-5-carboxylate (Compound 19)

Step 19-1: Preparation of ethyl 2-(4-aminophenyl) thiazole-5-carboxylate 12 mg (3% yield) of the title compound was obtained by performing a reaction in the same manner as in step 1-1 of Example 1, except that ethyl 2-bromothiazole-5-carboxylate (1.61 mmol) was used instead of 2-bromopyrimidine.

Step 19-2: Preparation of ethyl 2-(4-(2-(dicyanomethylene)hydrazinyl)phenyl) thiazole-5-carboxylate 12 mg (75% yield) of the title compound was obtained by performing a reaction in the same manner as in step 1-2 of Example 1, except that ethyl 2-(4-aminophenyl) thiazole-5-carboxylate was used instead of 4-(pyrimidin-2-yl)aniline.

Example 20: Preparation of (4-(thiazol-5-yl)phenyl)carbonohydrazonoyl dicyanide (Compound 20)

Step 20-1: Preparation of 4-(thiazol-5-yl)aniline 137 mg (85% yield) of the title compound was obtained by performing a reaction in the same manner as in step 1-1 of Example 1, except that 5-bromothiazole (0.91 mmol) was used instead of 2-bromopyrimidine.

Step 20-2: Preparation of (4-(thiazol-5-yl)phenyl)carbonohydrazonoyl dicyanide 60 mg (83% yield) of the title compound was obtained by performing a reaction in the same manner as in step 1-2 of Example 1, except that 4-(thiazol-5-yl)aniline was used instead of 4-(pyrimidin-2-yl)aniline.

Example 21: Preparation of (3'-fluoro-4'-nitrobiphenyl-4-yl)carbonohydrazonoyl dicyanide (Compound 21)

6 mg (7% yield) of the title compound was obtained by performing a reaction in the same manner as in step 1-2 of Example 1, except that 3'-fluoro-4'-nitrobiphenyl-4-amine was used instead of 4-(pyrimidin-2-yl)aniline.

Example 22: Preparation of (4-(6-fluoropyridin-3-yl)phenyl)carbonohydrazonoyl dicyanide (Compound 22)

Step 22-1: Preparation of 4-(6-fluoropyridin-3-yl)aniline 38 mg (45% yield) of the title compound was obtained by performing a reaction in the same manner as in step 1-1 of Example 1, except that 3-bromo-6-fluoropyridine (0.55 mmol) was used instead of 2-bromopyrimidine.

Step 22-2: Preparation of (4-(6-fluoropyridin-3-yl)phenyl)carbonohydrazonoyl dicyanide 23 mg (53% yield) of the title compound was obtained by performing a reaction in the same manner as in step 1-2 of Example 1, except that 4-(6-fluoropyridin-3-yl)aniline was used instead of 4-(pyrimidin-2-yl)aniline.

Example 23: Preparation of (2',4'-dimethylbiphenyl-4-yl)carbonohydrazonoyl dicyanide (Compound 23)

8 mg (6% yield) of the title compound was obtained by performing a reaction in the same manner as in step 1-2 of Example 1, except that 2',4'-dimethylbiphenyl-4-amine was used instead of 4-(pyrimidin-2-yl)aniline.

Example 24: Preparation of methyl 4'-(2-(dicyanomethylene)hydrazinyl)-2-fluorobiphenyl-4-carboxylate (Compound 24)

Step 24-1: Preparation of methyl 4'-amino-2-fluorobiphenyl-4-carboxylate 93 mg (60% yield) of the title compound was obtained by performing a reaction in the same manner as in step 1-1 of Example 1, except that methyl 4-bromo-3-fluorobenzoate (0.69 mmol) was used instead of 2-bromopyrimidine.

Step 24-2: Preparation of methyl 4'-(2-(dicyanomethylene)hydrazinyl)-2-fluorobiphenyl]-4-carboxylate 16 mg (16% yield) of the title compound was obtained by performing a reaction in the same manner as in step 1-2 of Example 1, except that 4'-amino-2-fluorobiphenyl-4-carboxylate was used instead of 4-(pyrimidin-2-yl)aniline.

Example 25: Preparation of (2'-methyl-4'-nitrobiphenyl-4-yl)carbonohydrazonoyl dicyanide (Compound 25)

Step 25-1: Preparation of 2'-methyl-4'-nitrobiphenyl-4-amine 98 mg (63% yield) of the title compound was obtained by performing a reaction in the same manner as in step 1-1 of Example 1, except that 1-bromo-2-methyl-4-nitrobenzene (0.69 mmol) was used instead of 2-bromopyrimidine.

Step 25-2: Preparation of (2'-methyl-4'-nitrobiphenyl-4-yl)carbonohydrazonoyl dicyanide 38 mg (27% yield) of the title compound was obtained by performing a reaction in the same manner as in step 1-2 of Example 1, except that 2'-methyl-4'-nitrobiphenyl-4-amine was used instead of 4-(pyrimidin-2-yl)aniline.

Example 26: Preparation of (2',4'-dichlorobiphenyl-4-yl)carbonohydrazonoyl dicyanide (Compound 26)

Step 26-1: Preparation of 2',4'-dichlorobiphenyl-4-amine 182 mg (84% yield) of the title compound was obtained by performing a reaction in the same manner as in step 1-1 of Example 1, except that 1-bromo-2,4-dichlorobenzene (0.91 mmol) was used instead of 2-bromopyrimidine.

Step 26-2: Preparation of (2',4'-(dichlorobiphenyl-4-yl)carbonohydrazonoyl dicyanide 47 mg (20% yield) of the title compound was obtained by performing a reaction in the same manner as in step 1-2 of Example 1, except that 2',4'-dichlorobiphenyl-4-amine was used instead of 4-(pyrimidin-2-yl)aniline.

Example 27: Preparation of (2'-methoxy-4'-methylbiphenyl-4-yl)carbonohydrazonoyl dicyanide (Compound 27)

Step 27-1: Preparation of 2'-methoxy-4'-methyl biphenyl-4-amine 36 mg (24% yield) of the title compound was obtained by performing a reaction in the same manner as in step 1-1 of Example 1, except that 1-bromo-2-methoxy-4-methylbenzene (0.69 mmol) was used instead of 2-bromopyrimidine.

Step 27-2: Preparation of (2'-methoxy-4'-methylbiphenyl-4-yl)carbonohydrazonoyl dicyanide 3 mg (6% yield) of the title compound was obtained by performing a reaction in the same manner as in step 1-2 of Example 1, except that 2'-methoxy-4'-methylbiphenyl-4-amine was used instead of 4-(pyrimidin-2-yl)aniline.

Example 28: Preparation of (4-(pyrazin-2-yl)phenyl)carbonohydrazonoyl dicyanide (Compound 28)

Step 28-1: Preparation of 4-(pyrazin-2-yl)aniline 72 mg (33% yield) of the title compound was obtained by performing a reaction in the same manner as in step 1-1 of Example 1, except that 2-bromopyrazine (1.26 mmol) was used instead of 2-bromopyrimidine.

Step 28-2: Preparation of (4-(pyrazin-2-yl)phenyl)carbonohydrazonoyl dicyanide 12 mg (12% yield) of the title compound was obtained by performing a reaction in the same manner as in step 1-2 of Example 1, except that 4-(pyrazin-2-yl)aniline was used instead of 4-(pyrimidin-2-yl)aniline.

Example 29: Preparation of (4-(5-(trifluoromethyl)pyrimidin-2-yl)phenyl)carbonohydrazonoyl dicyanide (Compound 29)

Step 29-1: Preparation of 4-(5-(trifluoromethyl)pyrimidin-2-yl)aniline 127 mg (78% yield) of the title compound was obtained by performing a reaction in the same manner as in step 1-1 of Example 1, except that 2-chloro-5-(trifluoromethyl)pyrimidine (0.83 mmol) was used instead of 2-bromopyrimidine.

Step 29-2: Preparation of (4-(5-(trifluoromethyl)pyrimidin-2-yl)phenyl)carbonohydrazonoyl dicyanide 47 mg (31% yield) of the title compound was obtained by performing a reaction in the same manner as in step 1-2 of Example 1, except that 4-(5-(trifluoromethyl)pyrimidin-2-yl)aniline was used instead of 4-(pyrimidin-2-yl)aniline.

Example 30: Preparation of (4-(4,6-dimethylpyrimidin-2-yl)phenyl)carbonohydrazonoyl dicyanide (Compound 30)

Step 30-1: Preparation of 4-(4,6-dimethylpyrimidin-2-yl)aniline 118 mg (67% yield) of the title compound was obtained by performing a reaction in the same manner as in step 1-1 of Example 1, except that 2-chloro-4,6-dimethylpyrimidine (1.05 mmol) was used instead of 2-bromopyrimidine.

Step 30-2: Preparation of (4-(4,6-dimethylpyrimidin-2-yl)phenyl)carbonohydrazonoyl dicyanide 110 mg (77% yield) of the title compound was obtained by performing a reaction in the same manner as in step 1-2 of Example 1, except that 4-(4,6-dimethylpyrimidin-2-yl) aniline was used instead of 4-(pyrimidin-2-yl)aniline.

Example 31: Preparation of (4-(4-methylpyrimidin-2-yl)phenyl)carbonohydrazonoyl dicyanide (Compound 31)

Step 31-1: Preparation of 4-(4-methylpyrimidin-2-yl)aniline 77 mg (57% yield) of the title compound was obtained by performing a reaction in the same manner as in step 1-1 of Example 1, except that 2-bromo-4-methylpyrimidine (0.87 mmol) was used instead of 2-bromopyrimidine.

Step 31-2: Preparation of (4-(4-methylpyrimidin-2-yl)phenyl)carbonohydrazonoyl dicyanide 66 mg (61% yield) of the title compound was obtained by performing a reaction in the same manner as in step 1-2 of Example 1, except that 4-(4-methylpyrimidin-2-yl)aniline was used instead of 4-(pyrimidin-2-yl)aniline.

Example 32: Preparation of (4-(pyrimidin-5-yl)phenyl)carbonohydrazonoyl dicyanide (Compound 32)

Step 32-1: Preparation of 4-(pyrimidin-5-yl)aniline 502 mg (64% yield) of the title compound was obtained by performing a reaction in the same manner as in step 1-1 of Example 1, except that 5-bromopyrimidine (0.87 mmol) was used instead of 2-bromopyrimidine.

Step 32-2: Preparation of (4-(pyrimidin-5-yl)phenyl)carbonohydrazonoyl dicyanide 100 mg (69% yield) of the title compound was obtained by performing a reaction in the same manner as in step 1-2 of Example 1, except that 4-(pyrimidin-5-yl)aniline was used instead of 4-(pyrimidin-2-yl)aniline.

Example 33: Preparation of (4-(1-methyl-1H-1,2,4-triazol-5-yl)phenyl)carbonohydrazonoyl dicyanide (Compound 33)

Step 33-1: Preparation of 4-(1-methyl-1H-1,2,4-triazol-5-yl)aniline 40 mg (20% yield) of the title compound was obtained by performing a reaction in the same manner as in step 1-1 of Example 1, except that 5-bromo-1-methyl-1H-1,2,4-triazole (0.96 mmol) was used instead of 2-bromopyrimidine.

Step 33-2: Preparation of (4-(1-methyl-1H-1,2,4-triazol-5-yl)phenyl)carbonohydrazonoyl dicyanide 18 mg (25% yield) of the title compound was obtained by performing a reaction in the same manner as in step 1-2 of Example 1, except that 4-(1-methyl-1H-1,2,4-triazol-5-yl) aniline was used instead of 4-(pyrimidin-2-yl)aniline.

Example 34: Preparation of (4-(1-methyl-1H-1,2,4-triazol-3-yl)phenyl)carbonohydrazonoyl dicyanide (Compound 34)

Step 34-1: Preparation of 4-(1-methyl-1H-1,2,4-triazol-3-yl)aniline 100 mg (50% yield) of the title compound was obtained by performing a reaction in the same manner as in step 1-1 of Example 1, except that 3-bromo-1-methyl-1H-1,2,4-triazole (0.96 mmol) was used instead of 2-bromopyrimidine.

Step 34-2: Preparation of (4-(1-methyl-1H-1,2,4-triazol-3-yl)phenyl)carbonohydrazonoyl dicyanide 29 mg (40% yield) of the title compound was obtained by performing a reaction in the same manner as in step 1-2 of Example 1, except that 4-(1-methyl-1H-1,2,4-triazol-3-yl) aniline was used instead of 4-(pyrimidin-2-yl)aniline.

Example 35: Preparation of (4-(1H-pyrazol-1-yl)phenyl)carbonohydrazonoyl dicyanide (Compound 35)

163 mg (55% yield) of the title compound was obtained by performing a reaction in the same manner as in step 1-2 of Example 1, except that 4-(1H-pyrazol-1-yl)aniline was used instead of 4-(pyrimidin-2-yl)aniline.

Example 36: Preparation of (4-(4-methyl-1H-pyrazol-1-yl)phenyl)carbonohydrazonoyl dicyanide (Compound 36)

Step 36-1: Preparation of 4-methyl-1-(4-nitrophenyl)-1H-pyrazole

4-Methyl-1H-pyrazole (100 mg, 1.22 mmol) was dissolved in 1.5 ml of DMSO in the presence of nitrogen, and then solid potassium tert-butoxide (164 mg, 1.46 mmol) and 1-fluoro-4-nitrobenzene (189 mg, 1.46 mmol) were added to obtain a reaction mixture. The reaction mixture was stirred at 72° C. for 20 hours. When the reaction was completed, the reaction product was cooled and then extracted using distilled water and ethyl acetate to obtain an organic layer, and the organic layer was dried over anhydrous magnesium sulfate and then filtered. The filtrate was concentrated under reduced pressure, and the concentrate was purified by recrystallization using an ethanol solvent to obtain 96 mg (39% yield) of the title compound.

Step 36-2: Preparation of 4-(4-methyl-1H-pyrazol-1-yl)aniline

4-Methyl-1-(4-nitrophenyl)-1H-pyrazole prepared according to step 1-1 was dissolved in 2.5 mL of ethanol, and then 10% (32 mg, 0.06 mmol) of a palladium catalyst activated with carbon was added, followed by stirring at room temperature for 1 hour in the presence of hydrogen gas. After the reaction was completed, the catalyst in the reaction mixture was filtered using celite. The filtrate was concentrated under reduced pressure, and the concentrate was purified by column chromatography to obtain 50 mg (98% yield) of the title compound.

Step 36-3: Preparation of (4-(4-methyl-1H-pyrazol-1-yl)phenyl)carbonohydrazonoyl dicyanide 50 mg (69% yield) of the title compound was obtained by performing a reaction in the same manner as in step 1-2 of Example 1, except that 4-(4-methyl-1H-pyrazol-1-yl)aniline was used instead of 4-(pyrimidin-2-yl)aniline.

Example 37: Preparation of (2-fluoro-4-(4-methylpyrimidin-2-yl)phenyl)carbonohydrazonoyl dicyanide (Compound 37)

Step 37-1: Preparation of 2-fluoro-4-(4-methylpyrimidin-2-yl)aniline 100 mg (50% yield) of the title compound was obtained by performing a reaction in the same manner as in step 1-1 of Example 1, except that 4-amino-3-fluorophenylboronic acid pinacol ester (2-fluoro-4-(4,4,5,5-tetramethyl-1,3,2-dioxaborolan-2-yl)aniline) (0.84 mmol) was used instead of 4-aminophenylboronic acid pinacol ester, and 2-bromo-4-methylpyrimidine (1.01 mmol) was used instead of 2-bromopyrimidine.

Step 37-2: Preparation of (2-fluoro-4-(4-methylpyrimidin-2-yl)phenyl)carbonohydrazonoyl dicyanide 46 mg (67% yield) of the title compound was obtained by performing a reaction in the same manner as in step 1-2 of Example 1, except that 2-fluoro-4-(4-methylpyrimidin-2-yl)aniline was used instead of 4-(pyrimidin-2-yl)aniline.

Example 38: Preparation of (2-fluoro-4-(pyrimidin-2-yl)phenyl)carbonohydrazonoyl dicyanide (Compound 38)

Step 38-1: Preparation of 2-fluoro-4-(pyrimidin-2-yl)aniline 41 mg (17% yield) of the title compound was obtained by performing a reaction in the same manner as in step 37-1 of Example 37, except that 2-bromopyrimidine (1.26 mmol) was used instead of 2-bromo-4-methylpyrimidine.

Step 38-2: Preparation of (2-fluoro-4-(pyrimidin-2-yl)phenyl)carbonohydrazonoyl dicyanide 11 mg (19% yield) of the title compound was obtained by performing a reaction in the same manner as in step 1-2 of Example 1, except that 2-fluoro-4-(pyrimidin-2-yl)aniline was used instead of 4-(pyrimidin-2-yl)aniline.

Example 39: Preparation of (3-fluoro-4-(pyrimidin-2-yl)phenyl)carbonohydrazonoyl dicyanide (Compound 39)

Step 39-1: Preparation of 3-fluoro-4-(pyrimidin-2-yl)aniline 156 mg (66% yield) of the title compound was obtained by performing a reaction in the same manner as in step 1-1 of Example 1, except that 4-amino-2-fluorophenylboronic acid pinacol ester (1.38 mmol) was used instead of 4-aminophenylboronic acid pinacol ester.

Step 39-2: Preparation of (3-fluoro-4-(pyrimidin-2-yl)phenyl)carbonohydrazonoyl dicyanide 80 mg (81% yield) of the title compound was obtained by performing a reaction in the same manner as in step 1-2 of Example 1, except that 3-fluoro-4-(pyrimidin-2-yl)aniline was used instead of 4-(pyrimidin-2-yl)aniline.

Example 40: Preparation of (3-fluoro-4-(4-methylpyrimidin-2-yl)phenyl)carbonohydrazonoyl dicyanide (Compound 40)

Step 40-1: Preparation of 3-fluoro-4-(4-methylpyrimidin-2-yl)aniline 82 mg (35% yield) of the title compound was obtained by performing a reaction in the same manner as in step 39-1 of Example 39, except that 2-bromo-4-methylpyrimidine (1.16 mmol) was used instead of 2-bromopyrimidine.

Step 40-2: Preparation of (3-fluoro-4-(4-methylpyrimidin-2-yl)phenyl)carbonohydrazonoyl dicyanide 56 mg (92% yield) of the title compound was obtained by performing a reaction in the same manner as in step 1-2 of Example 1, except that 3-fluoro-4-(4-methylpyrimidin-2-yl) aniline was used instead of 4-(pyrimidin-2-yl)aniline.

Example 41: Preparation of (2-methoxy-4-(5-methylpyrimidin-2-yl)phenyl)carbonohydrazonoyl dicyanide (Compound 41)

Step 41-1: Preparation of 2-methoxy-4-(5-methylpyrimidin-2-yl)aniline 99 mg (47% yield) of the title compound was obtained by performing a reaction in the same manner as in step 1-1 of Example 1, except that 4-amino-3-methoxyboronic acid pinacol ester (0.99 mmol) was used instead of 4-aminophenylboronic acid pinacol ester, and 2-chloro-5-methylpyrimidine (1.19 mmol) was used instead of 2-bromopyrimidine.

Step 41-2: Preparation of (2-methoxy-4-(5-methylpyrimidin-2-yl)phenyl)carbonohydrazonoyl dicyanide 25 mg (61% yield) of the title compound was obtained by performing a reaction in the same manner as in step 1-2 of Example 1, except that 2-methoxy-4-(5-methylpyrimidin-2-yl)aniline was used instead of 4-(pyrimidin-2-yl)aniline.

Example 42: Preparation of (2-methoxy-4-(4-methylpyrimidin-2-yl)phenyl)carbonohydrazonoyl dicyanide (Compound 42)

Step 42-1: Preparation of 2-methoxy-4-(4-methylpyrimidin-2-yl)aniline 80 mg (42% yield) of the title compound was obtained by performing a reaction in the same manner as in step 41-1 of Example 41, except that 2-bromo-4-methylpyrimidine (1.12 mmol) was used instead of 2-chloro-5-methylpyrimidine.

Step 42-2: Preparation of (2-methoxy-4-(4-methylpyrimidin-2-yl)phenyl)carbonohydrazonoyl dicyanide 10 mg (58% yield) of the title compound was obtained by performing a reaction in the same manner as in step 1-2 of Example 1, except that 2-methoxy-4-(4-methylpyrimidin-2-yl)aniline was used instead of 4-(pyrimidin-2-yl)aniline.

Example 43: Preparation of (2-methoxy-4-(pyrimidin-2-yl)phenyl)carbonohydrazonoyl dicyanide (Compound 43)

Step 43-1: Preparation of 2-methoxy-4-(pyrimidin-2-yl)aniline 29 mg (18% yield) of the title compound was obtained by performing a reaction in the same manner as in step 41-1 of Example 41, except that 2-bromopyrimidine (0.96 mmol) was used instead of 2-chloro-5-methylpyrimidine.

Step 43-2: Preparation of (2-methoxy-4-(pyrimidin-2-yl)phenyl)carbonohydrazonoyl dicyanide 26 mg (65% yield) of the title compound was obtained by performing a reaction in the same manner as in step 1-2 of Example 1, except that 2-methoxy-4-(pyrimidin-2-yl)aniline was used instead of 4-(pyrimidin-2-yl)aniline.

Example 44: Preparation of (4-(5-fluoropyrimidin-2-yl)-2-morpholinophenyl)carbonohydrazonoyl dicyanide (Compound 44)

Step 44-1: Preparation of 2-(3-fluoro-4-nitrophenyl)-4,4,5,5-tetramethyl-1,3,2-dioxaborolane 4-Bromo-2-fluoro-1-nitrobenzene (2 g, 7.88 mmol) and bis(pinacolato)diboron (4,4,4',4',5,5,5',5'-octamethyl-2,2'-bi(1,3,2-dioxaborolane); 2.1 g, 9.45 mmol) were dissolved in 60 mL of a 1,4-dioxane solution in the presence of nitrogen, and then Pd(dppf)$_2$Cl$_2$ (1.3 g, 1.58 mmol) and potassium acetate (3.1 g, 31.5 mmol) were added to obtain a reaction mixture. The reaction mixture was stirred at 80° C. for 12 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 1.6 g of the title compound.

Step 44-2: Preparation of 4-(2-nitro-5-(4,4,5,5-tetramethyl-1,3,2-dioxaborolan-2-yl)phenyl) morpholine 2-(3-Fluoro-4-nitrophenyl)-4,4,5,5-tetramethyl-1,3,2-dioxaborolane prepared according to step 44-1 and morpholine (0.68 mL, 7.79 mmol) were dissolved in acetonitrile (20 mL) in the presence of nitrogen to obtain a reaction mixture, and then the reaction mixture was stirred at 80° C. for 12 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 700 g of the title compound.

Step 44-3: Preparation of 4-(5-(5-fluoropyrimidin-2-yl)-2-nitrophenyl) morpholine 164 mg (26% yield) of the title compound was obtained by performing a reaction in the same manner as in step 1-1 of Example 1, except that 4-(2-nitro-5-(4,4,5,5-tetramethyl-1,3,2-dioxaborolan-2-yl)phenyl) morpholine prepared according to step 44-2 was used instead of 4-aminophenylboronic acid pinacol ester, and 2-chloro-5-fluoropyrimidine (2.51 mmol) was used instead of 2-bromopyrimidine.

Step 44-4: Preparation of 4-(5-fluoropyrimidin-2-yl)-2-morpholinoaniline 4-(5-(5-Fluoropyrimidin-2-yl)-2-nitrophenyl) morpholine prepared according to step 44-3 was dissolved in ethyl acetate, and was reduced in the same manner as in step 36-2 of Example 36 to obtain 84 mg (57% yield) of the title compound.

Step 44-5: Preparation of (4-(5-fluoropyrimidin-2-yl)-2-morpholinophenyl)carbonohydrazonoyl dicyanide 70 mg (65% yield) of the title compound was obtained by performing a reaction in the same manner as in step 1-2 of Example 1, except that 4-(5-fluoropyrimidin-2-yl)-2-morpholinoaniline prepared according to step 44-4 was used instead of 4-(pyrimidin-2-yl)aniline.

Example 45: Preparation of methyl (4-(pyrimidin-2-yl)phenyl)carbonohydrazonoyl dicyanide (Compound 45)

(4-(Pyrimidin-2-yl)phenyl)carbonohydrazonoyl dicyanide (50 mg, 0.20 mmol) prepared according to Example 1 was dissolved in 1.5 ml of tetrahydrofuran, and then potassium tert-butoxide (29 mg, 0.26 mmol) was added at room temperature, and iodomethane (25 μL, 0.40 mmol) was further added to obtain a reaction mixture. The reaction mixture was stirred at 60° C. for 4 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by recrystallization using an ethanol solvent to obtain 3 mg (6% yield) of the title compound.

Example of (3-(5-fluoropyrimidin-2-46: Preparation yl)phenyl)carbonohydrazonoyl dicyanide (Compound 46)

Step 46-1: Preparation of 3-(5-fluoropyrimidin-2-yl)aniline 180 mg of the title compound was obtained by performing a reaction in the same manner as in step 1-1 of Example 41, except that 3-aminophenylboronic acid pinacol ester (1.37 mmol) was used instead of 4-aminophenylboronic acid pinacol ester, and 2-chloro-5-fluoropyrimidine (1.64 mmol) was used instead of 2-bromopyrimidine.

Step 46-2: Preparation of (3-(5-fluoropyrimidin-2-yl)phenyl)carbonohydrazonoyl dicyanide 70.5 mg of the title compound was obtained by performing a reaction in the same manner as in step 1-2 of Example 1, except that 3-(5-fluoropyrimidin-2-yl)aniline was used instead of 4-(pyrimidin-2-yl)aniline.

Example 47: Preparation of (5-(5-fluoropyrimidin-2-yl)-2-morpholinophenyl)carbonohydrazonoyl dicyanide (Compound 47)

Step 47-1: Preparation of 4-(2-nitro-4-(4,4,5,5-tetramethyl-1,3,2-dioxaborolan-2-yl)phenyl) morpholine 480 mg (41% yield) of the title compound was obtained by performing a reaction in the same manner as in step 44-2 of Example 44, except that 2-(4-chloro-3-nitrophenyl)-4,4,5,5-tetramethyl-1,3,2-dioxaborolane was used instead of 2-(3-fluoro-4-nitrophenyl)-4,4,5,5-tetramethyl-1,3,2-dioxaborolane.

Step 47-2: Preparation of 4-(4-(5-fluoropyrimidin-2-yl)-2-nitrophenyl) morpholine 300 mg (70% yield) of the title compound was obtained by performing a reaction in the same manner as in step 1-1 of Example 1, except that 4-(2-nitro-4-(4,4,5,5-tetramethyl-1,3,2-dioxaborolan-2-yl)phenyl) morpholine prepared according to step 47-1 was used instead of 4-aminophenylboronic acid pinacol ester, and 2-chloro-5-fluoropyrimidine was used instead of 2-bromopyrimidine.

Step 47-3: Preparation of 5-(5-fluoropyrimidin-2-yl)-2-morpholinoaniline 4-(5-(5-Fluoropyrimidin-2-yl)-2-nitrophenyl) morpholine prepared according to step 44-3 was dissolved in dichloromethane (DCM), and was reduced in a similar manner to step 36-2 of Example 36 to obtain 86 mg (48% yield) of the title compound.

Step 47-4: Preparation of (5-(5-fluoropyrimidin-2-yl)-2-morpholinophenyl)carbonohydrazonoyl dicyanide 84 mg (77% yield) of the title compound was obtained by performing a reaction in the same manner as in step 1-2 of Example 1, except that 5-(5-fluoropyrimidin-2-yl)-2-morpholinoaniline prepared according to step 47-3 was used instead of 4-(pyrimidin-2-yl)aniline.

Example 48: Preparation of (4-(benzo[d]thiazol-6-yl)phenyl)carbonohydrazonoyl dicyanide (Compound 48)

Step 48-1: Preparation of 4-(benzo[d]thiazol-6-yl)aniline 58 mg (68% yield) of the title compound was obtained by performing a reaction in the same manner as in step 1-1 of Example 1, except that 6-bromobenzo[d]thiazole (0.55 mmol) was used instead of 2-bromopyrimidine.

Step 48-2: Preparation of (4-(benzo[d]thiazol-6-yl) phenyl)carbonohydrazonoyl dicyanide 10 mg (13% yield) of the title compound was obtained by performing a reaction in the same manner as in step 1-2 of Example 1, except that 4-(benzo[d]thiazol-6-yl)aniline was used instead of 4-(pyrimidin-2-yl)aniline.

Example 49: Preparation of (4-(naphthalen-2-yl)phenyl)carbonohydrazonoyl dicyanide (Compound 49)

Step 49-1: Preparation of 4-(naphthalen-2-yl)aniline 40 mg (21% yield) of the title compound was obtained by performing a reaction in the same manner as in step 1-1 of Example 1, except that 2-bromonaphthalene (0.46 mmol) was used instead of 2-bromopyrimidine.

Step 49-2: Preparation of (4-(naphthalen-2-yl)phenyl)carbonohydrazonoyl dicyanide 5 mg (9% yield) of the title compound was obtained by performing a reaction in the same manner as in step 1-2 of Example 1, except that 4-(naphthalen-2-yl)aniline was used instead of 4-(pyrimidin-2-yl)aniline.

Example 50: Preparation of (4-(pyrazolo[1,5-a]pyrimidin-6-yl)phenyl)carbonohydrazonoyl dicyanide (Compound 50)

Step 50-1: Preparation of 4-(pyrazolo[1,5-a]pyrimidin-6-yl)aniline 180 mg (62% yield) of the title compound was obtained by performing a reaction in the same manner as in step 1-1 of Example 1, except that 6-bromopyrazolo[1,5-a]pyrimidine (1.65 mmol) was used instead of 2-bromopyrimidine.

Step 50-2: Preparation of (4-(pyrazolo[1,5-a]pyrimidin-6-yl)phenyl)carbonohydrazonoyl dicyanide 79 mg (32% yield) of the title compound was obtained by performing a reaction in the same manner as in step 1-2 of Example 1, except that 4-(pyrazolo[1,5-a]pyrimidin-6-yl) aniline was used instead of 4-(pyrimidin-2-yl)aniline.

Example 51: Preparation of (4-(imidazo[1,2-a]pyrimidin-6-yl)phenyl)carbonohydrazonoyl dicyanide (Compound 51)

Step 51-1: Preparation of 4-(imidazo[1,2-a]pyrimidin-6-yl)aniline 76 mg (17% yield) of the title compound was obtained by performing a reaction in the same manner as in step 1-1 of Example 1, except that 6-bromoimidazo[1,2-a]pyrimidine (2.53 mmol) was used instead of 2-bromopyrimidine.

Step 51-2: Preparation of (4-(imidazo[1,2-a]pyrimidin-6-yl)phenyl)carbonohydrazonoyl dicyanide 40 mg (38% yield) of the title compound was obtained by performing a reaction in the same manner as in step 1-2 of Example 1, except that 4-(imidazo[1,2-a]pyrimidin-6-yl) aniline was used instead of 4-(pyrimidin-2-yl)aniline.

Example 52: Preparation of (4-(quinoxalin-2-yl)phenyl)carbonohydrazonoyl dicyanide (Compound 52)

Step 52-1: Preparation of 4-(quinoxalin-2-yl)aniline 100 mg (33% yield) of the title compound was obtained by performing a reaction in the same manner as in step 1-1 of Example 1, except that 2-chloroquinoxaline (1.64 mmol) was used instead of 2-bromopyrimidine.

Step 52-2: Preparation of (4-(quinoxalin-2-yl)phenyl)carbonohydrazonoyl dicyanide 30 mg (44% yield) of the title compound was obtained by performing a reaction in the same manner as in step 1-2 of Example 1, except that 4-(quinoxalin-2-yl)aniline was used instead of 4-(pyrimidin-2-yl)aniline.

Example 53: Preparation of (4-(imidazo[1,2-a]pyridin-6-yl)phenyl)carbonohydrazonoyl dicyanide (Compound 53)

Step 53-1: Preparation of 4-(imidazo[1,2-a]pyridin-6-yl)aniline 100 mg (33% yield) of the title compound was obtained by performing a reaction in the same manner as in step 1-1 of Example 1, except that 6-bromoimidazo[1,2-a]pyridine (1.64 mmol) was used instead of 2-bromopyrimidine.

Step 53-2: Preparation of 4-(imidazo[1,2-a]pyridin-6-yl)phenyl)carbonohydrazonoyl dicyanide 22 mg (32% yield) of the title compound was obtained by performing a reaction in the same manner as in step 1-2 of Example 1, except that 4-(imidazo[1,2-a]pyridin-6-yl)aniline was used instead of 4-(pyrimidin-2-yl)aniline.

Example 54: Preparation of (4-(isoquinolin-3-yl)phenyl)carbonohydrazonoyl dicyanide (Compound 54)

Step 54-1: Preparation of 4-(isoquinolin-3-yl)aniline 80 mg (16% yield) of the title compound was obtained by performing a reaction in the same manner as in step 1-1 of Example 1, except that 3-chloroisoquinoline (2.80 mmol) was used instead of 2-bromopyrimidine.

Step 54-2: Preparation of (4-(isoquinolin-3-yl)phenyl)carbonohydrazonoyl dicyanide 23 mg (42% yield) of the title compound was obtained by performing a reaction in the same manner as in step 1-2 of Example 1, except that 4-(isoquinolin-3-yl)aniline was used instead of 4-(pyrimidin-2-yl)aniline.

Example 55: Preparation of (4-(2-methyl-2H-indazol-4-yl)phenyl)carbonohydrazonoyl dicyanide (Compound 55)

Step 55-1: Preparation of 4-(2-methyl-2H-indazol-4-yl)aniline 331 mg (80% yield) of the title compound was obtained by performing a reaction in the same manner as in step 1-1 of Example 1, except that 4-bromo-2-methyl-2H-indazole (2.20 mmol) was used instead of 2-bromopyrimidine.

Step 55-2: Preparation of (4-(2-methyl-2H-indazol-4-yl)phenyl)carbonohydrazonoyl dicyanide 100 mg (24% yield) of the title compound was obtained by performing a reaction in the same manner as in step 1-2 of Example 1, except that 4-(2-methyl-2H-indazol-4-yl) aniline was used instead of 4-(pyrimidin-2-yl)aniline.

Example 56: Preparation of (4-(2-methyl-2H-indazol-5-yl)phenyl)carbonohydrazonoyl dicyanide (Compound 56)

Step 56-1: Preparation of 4-(2-methyl-2H-indazol-5-yl)aniline 100 mg (38% yield) of the title compound was obtained by performing a reaction in the same manner as in step 1-1 of Example 1, except that 5-bromo-2-methyl-2H-indazole (2.20 mmol) was used instead of 2-bromopyrimidine.

Step 56-2: Preparation of (4-(2-methyl-2H-indazol-5-yl)phenyl)carbonohydrazonoyl dicyanide 26 mg (65% yield) of the title compound was obtained by performing a reaction in the same manner as in step 1-2 of Example 1, except that 4-(2-methyl-2H-indazol-5-yl)aniline was used instead of 4-(pyrimidin-2-yl)aniline.

Example of (4-(2-methyl-2H-indazol-7-57: Preparation yl)phenyl)carbonohydrazonoyl dicyanide (Compound 57)

Step 57-1: Preparation of 4-(2-methyl-2H-indazol-7-yl)aniline 550 mg (86% yield) of the title compound was obtained by performing a reaction in the same manner as in step 1-1 of Example 1, except that 7-bromo-2-methyl-2H-indazole (2.20 mmol) was used instead of 2-bromopyrimidine.

Step 57-2: Preparation of (4-(2-methyl-2H-indazol-7-yl)phenyl)carbonohydrazonoyl dicyanide 345 mg (47% yield) of the title compound was obtained by performing a reaction in the same manner as in step 1-2 of Example 1, except that 4-(2-methyl-2H-indazol-7-yl) aniline was used instead of 4-(pyrimidin-2-yl)aniline.

Example 58: Preparation of (4-(1H-indol-5-yl)phenyl)carbonohydrazonoyl dicyanide (Compound 58)

Step 58-1: Preparation of tert-butyl 5-(4-aminophenyl)-1H-indole-1-carboxylate 596 mg (6% yield) of the title compound was obtained by performing a reaction in the same manner as in step 1-1 of Example 1, except that tert-butyl 5-bromo-1H-indole-1-carboxylate (3.38 mmol) was used instead of 2-bromopyrimidine.

Step 58-2: Preparation of tert-butyl 5-(4-(2-(dicyanomethylene)hydrazinyl)phenyl)-1H-indol-1-ylcarboxylate 107 mg (14% yield) of the title compound was obtained by performing a reaction in the same manner as in step 1-2 of Example 1, except that tert-butyl 5-(4-aminophenyl)-1H-indole-1-carboxylate was used instead of 4-(pyrimidin-2-yl) aniline.

Step 58-3: Preparation of (4-(1H-indol-5-yl)phenyl)carbonohydrazonoyl dicyanide tert-Butyl 5-(4-(2-(dicyanomethylene)hydrazinyl)phenyl)-1H-indol-1-ylcarboxylate was dissolved in 8.0 mL of dichloromethane in the presence of nitrogen, and then trifluoroacetic acid was added to obtain a reaction mixture. The reaction mixture was stirred at room temperature for 2 hours. When the reaction was completed, the reaction product was concentrated under reduced pressure to obtain 40 mg (44% yield) of the title compound.

Example 59: Preparation of (4-methoxybenzo[d]thiazol-2-yl)carbonohydrazonoyl dicyanide (Compound 59)

141 mg (51% yield) of the title compound was obtained by performing a reaction in the same manner as in step 1-2 of Example 1, except that 4-methoxybenzo[d]thiazol-2-amine was used instead of 4-(pyrimidin-2-yl)aniline.

Example 60: Preparation of benzo[d]thiazol-6-ylcarbonohydrazonoyl dicyanide (Compound 60)

290 mg (48% yield) of the title compound was obtained by performing a reaction in the same manner as in step 1-2 of Example 1, except that benzo[d]thiazole-6-amine was used instead of 4-(pyrimidin-2-yl)aniline.

Example 61: Preparation of benzo[d]thiazol-5-ylcarbonohydrazonoyl dicyanide (Compound 61)

180 mg (40% yield) of the title compound was obtained by performing a reaction in the same manner as in step 1-2 of Example 1, except that benzo[d]thiazol-5-amine was used instead of 4-(pyrimidin-2-yl)aniline.

Example 62: Preparation of (9-ethyl-9H-carbazol-3-yl)carbonohydrazonoyl dicyanide (Compound 62)

77 mg (11% yield) of the title compound was obtained by performing a reaction in the same manner as in step 1-2 of Example 1, except that 9-ethyl-9H-carbazol-3-amine was used instead of 4-(pyrimidin-2-yl)aniline.

Example 63: Preparation of (1-methyl-1H-indazol-6-yl)carbonohydrazonoyl dicyanide (Compound 63)

246 mg (54% yield) of the title compound was obtained by performing a reaction in the same manner as in step 1-2 of Example 1, except that 1-methyl-1H-indazol-6-amine was used instead of 4-(pyrimidin-2-yl)aniline.

Example 64: Preparation of quinolin-3-ylcarbonohydrazonoyl dicyanide (Compound 64)

163 mg (27% yield) of the title compound was obtained by performing a reaction in the same manner as in step 1-2 of Example 1, except that quinolin-3-amine was used instead of 4-(pyrimidin-2-yl)aniline.

Example 65: Preparation of (2-methyl-2H-indazol-6-yl) Carbonohydrazonoyl Dicyanide (Compound 65)

23 mg (3% yield) of the title compound was obtained by performing a reaction in the same manner as in step 1-2 of Example 1, except that 2-methyl-2H-indazol-6-amine was used instead of 4-(pyrimidin-2-yl)aniline.

Example 66: Preparation of (1-methyl-1H-indazol-5-yl)carbonohydrazonoyl dicyanide (Compound 66)

128 mg (17% yield) of the title compound was obtained by performing a reaction in the same manner as in step 1-2 of Example 1, except that 1-methyl-1H-indazol-5-amine was used instead of 4-(pyrimidin-2-yl)aniline.

Example 67: Preparation of quinoline-6-ylcarbonohydrazonoyl dicyanide (Compound 67)

56 mg (9% yield) of the title compound was obtained by performing a reaction in the same manner as in step 1-2 of Example 1, except that quinoline-6-amine was used instead of 4-(pyrimidin-2-yl)aniline.

Example 68: Preparation of (1-methyl-1H-indol-5-yl)carbonohydrazonoyl dicyanide (Compound 68)

69 mg (11% yield) of the title compound was obtained by performing a reaction in the same manner as in step 1-2 of Example 1, except that 1-methyl-1H-indol-5-amine was used instead of 4-(pyrimidin-2-yl)aniline.

Example 69: Preparation of (1H-indazol-5-yl)carbonohydrazonoyl dicyanide (Compound 69)

70 mg (19% yield) of the title compound was obtained by performing a reaction in the same manner as in step 1-2 of Example 1, except that tert-butyl 5-amino-1H-indazole-1-carboxylate was used instead of 4-(pyrimidin-2-yl)aniline.

Example 70: Preparation of (1H-indazol-6-yl)carbonohydrazonoyl dicyanide (Compound 70)

62 mg (12% yield) of the title compound was obtained by performing a reaction in the same manner as in step 1-2 of Example 1, except that tert-butyl 6-amino-1H-indazole-1-carboxylate was used instead of 4-(pyrimidin-2-yl)aniline.

Example 71: Preparation of (1H-indol-5-yl)carbonohydrazonoyl dicyanide (Compound 71)

Step 71-1: Preparation of tert-butyl 5-(2-(dicyanomethylene)hydrazinyl)-1H-indole-1-carboxylate 25 mg (6% yield) of the title compound was obtained by performing a reaction in the same manner as in step 1-2 of Example 1, except that tert-butyl 5-amino-1H-indole-1-carboxylate was used instead of 4-(pyrimidin-2-yl)aniline.

Step 71-2: Preparation of (1H-indol-5-yl)carbonohydrazonoyl dicyanide 15 mg (88% yield) of the title compound was obtained by performing a reaction in the same manner as in step 58-3 of Example 58, except that tert-butyl 5-(2-(dicyanomethylene)hydrazinyl)-1H-indol-1-ylcarboxylate was used instead of tert-butyl 5-(4-(2-(dicyanomethylene)hydrazinyl)phenyl)-1H-indol-1-ylcarboxylate.

Example 72: Preparation of (1H-pyrrolo[2,3-b]pyridin-5-yl)carbonohydrazonoyl dicyanide (Compound 72)

Step 72-1: Preparation of tert-butyl 5-nitro-1H-pyrrolo[2,3-b]pyridine-1-carboxylate 5-Nitro-1H-pyrrolo[2,3-b]pyridine (2 g, 12.27 mmol), di-tert-butyl dicarbonate (3.2 g, 14.71 mmol), and 4-dimethylaminopyridine (150 mg, 1.23 mmol) were dissolved in 40 mL of an acetonitrile solution in the presence of nitrogen, and then stirred at room temperature for 3 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 1.23 g (38% yield) of the title compound.

Step 72-2: Preparation of tert-butyl 5-amino-1H-pyrrolo[2,3-b]pyridine-1-carboxylate tert-Butyl 5-nitro-1H-pyrrolo[2,3-b]pyridine-1-carboxylate (600 mg, 2.28 mmol) prepared according to step 72-1 was dissolved in 5 ml of an acetic acid solution in the presence of nitrogen, and then iron (1.2 g, 22.80 mmol) was added to obtain a reaction mixture. The reaction mixture was stirred at room temperature for 2 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 261 mg (48% yield) of the title compound.

Step 72-3: Preparation of (1H-pyrrolo[2,3-b]pyridin-5-yl)carbonohydrazonoyl dicyanide 128 mg (54% yield) of the title compound was obtained by performing a reaction in the same manner as in step 1-2 of Example 1, except that tert-butyl 5-amino-1H-pyrrolo[2,3-b]pyridine-1-carboxylate was used instead of 4-(pyrimidin-2-yl)aniline.

Example 73: Preparation of (3-methyl-1H-indazol-6-yl)carbonohydrazonoyl dicyanide (Compound 73)

Step 73-1: Preparation of tert-butyl 3-methyl-6-nitro-1H-indazole-1-carboxylate 1.43 g (92% yield) of the title compound was obtained by performing a reaction in the same manner as in step 72-1 of Example 72, except that 3-methyl-6-nitro-1H-indazole was used instead of 5-nitro-1H-pyrrolo[2,3-b]pyridine.

Step 73-2: Preparation of tert-butyl 6-amino-3-methyl-1H-indazole-1-carboxylate tert-Butyl 3-methyl-6-nitro-1H-indazole-1-carboxylate prepared according to step 73-1 was dissolved in ethyl acetate, and was reduced in the same manner as in step 36-2 of Example 36 to obtain 500 mg (80% yield) of the title compound.

Step 73-3: Preparation of (3-methyl-1H-indazol-6-yl)carbonohydrazonoyl dicyanide 40 mg (10% yield) of the title compound was obtained by performing a reaction in the same manner as in step 1-2 of Example 1, except that tert-butyl 6-amino-3-methyl-1H-indazole-1-carboxylate was used instead of 4-(pyrimidin-2-yl)aniline.

Example 74: Preparation of (3-methyl-1H-indazol-5-yl)carbonohydrazonoyl dicyanide (Compound 74)

Step 74-1: Preparation of tert-butyl 3-methyl-5-nitro-1H-indazole-1-carboxylate 2.83 g (90% yield) of the title compound was obtained by performing a reaction in the same manner as in step 72-1 of Example 72, except that 3-methyl-5-nitro-1H-indazole (1.29 mmol) was used instead of 5-nitro-1H-pyrrolo[2,3-b]pyridine.

Step 74-2: Preparation of tert-butyl 5-amino-3-methyl-1H-indazole-1-carboxylate tert-Butyl 3-methyl-5-nitro-1H-indazole-1-carboxylate prepared according to step 74-1 was dissolved in ethyl acetate, and was reduced in the same manner as in step 36-2 of Example 36 to obtain 761 mg (85% yield) of the title compound.

Step 74-3: Preparation of (3-methyl-1H-indazol-5-yl)carbonohydrazonoyl dicyanide 100 mg (15% yield) of the title compound was obtained by performing a reaction in the same manner as in step 1-2 of Example 1, except that tert-butyl 5-amino-3-methyl-1H-indazole-1-carboxylate was used instead of 4-(pyrimidin-2-yl)aniline.

Example 75: Preparation of (1H-indol-4-yl)carbonohydrazonoyl dicyanide (Compound 75)

Step 75-1: Preparation of tert-butyl 4-amino-1H-indole-1-carboxylate tert-Butyl 4-nitro-1H-indole-1-carboxylate was dissolved in acetonitrile (MeCN), and was reduced in the same manner as in step 36-2 of Example 36 to obtain 198 mg (75% yield) of the title compound.

Step 75-2: Preparation of (1H-indol-4-yl)carbonohydrazonoyl dicyanide 40 mg (10% yield) of the title compound was obtained by performing a reaction in the same manner as in step 1-2 of Example 1, except that tert-butyl 4-amino-1H-indole-1-carboxylate was used instead of 4-(pyrimidin-2-yl)aniline.

Example 76: Preparation of (1-methyl-1H-pyrrolo[2,3-b]pyridin-5-yl)carbonohydrazonoyl dicyanide (Compound 76)

Step 76-1: Preparation of 1-methyl-5-nitro-1H-pyrrolo[2,3-b]pyridine

5-Nitro-1H-pyrrolo[2,3-b]pyridine (600 mg, 3.72 mmol) was dissolved in DMF (6 mL) in the presence of nitrogen, and then sodium hydride (60%, 300 mg, 7.44 mmol) was added, followed by addition of iodomethane (0.93 mL, 14.88 mmol) to obtain a reaction mixture. The reaction mixture was stirred at room temperature for 4 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 380 mg (57% yield) of the title compound.

Step 76-2: Preparation of 1-methyl-1H-pyrrolo[2,3-b]pyridin-5-amine 69 mg (55% yield) of the title compound was obtained by performing a reaction in the same manner as in step 72-2 of Example 72, except that 1-methyl-5-nitro-1H-pyrrolo[2,3-b]pyridine obtained from step 76-1 was used instead of tert-butyl 5-nitro-1H-pyrrolo[2,3-b]pyridine-1-carboxylate.

Step 76-3: Preparation of (1-methyl-1H-pyrrolo[2,3-b]pyridin-5-yl)carbonohydrazonoyl dicyanide 8 mg (9% yield) of the title compound was obtained by performing a reaction in the same manner as in step 1-2 of Example 1, except that 1-methyl-1H-pyrrolo[2,3-b]pyridin-5-amine was used instead of 4-(pyrimidin-2-yl)aniline.

Example 77: Preparation of (1-propyl-1H-pyrrolo[2,3-b]pyridin-5-yl)carbonohydrazonoyl dicyanide (Compound 77)

Step 77-1: Preparation of 5-nitro-1-propyl-1H-pyrrolo[2,3-b]pyridine

5-Nitro-1H-pyrrolo[2,3-b]pyridine (600 mg, 3.72 mmol), cesium carbonate ($CsCO_3$, 2.4 g, 7.44 mmol), and 1-iodopropane (1.10 mL, 11.01 mmol) were dissolved in DMF to obtain a reaction mixture, and then the reaction mixture was stirred at 60° C. for 17 hours to obtain 523 mg (70% yield) of the title compound.

Step 77-2: Preparation of 1-propyl-1H-pyrrolo[2,3-b]pyridin-5-amine 297 mg (67% yield) of the title compound was obtained by performing a reaction in the same manner as in step 72-2 of Example 72, except that 5-nitro-1-propyl-1H-pyrrolo[2,3-b]pyridine obtained from step 77-1 was used instead of tert-butyl 5-nitro-1H-pyrrolo[2,3-b]pyridine-1-carboxylate.

Step 77-3: Preparation of (1-propyl-1H-pyrrolo[2,3-b]pyridin-5-yl)carbonohydrazonoyl dicyanide 98 mg (23% yield) of the title compound was obtained by performing a reaction in the same manner as in step 1-2 of Example 1, except that 1-propyl-1H-pyrrolo[2,3-b]pyridin-5-amine was used instead of 4-(pyrimidin-2-yl)aniline.

Example 78: Preparation of (1-isopropyl-1H-pyrrolo[2,3-b]pyridin-5-yl)carbonohydrazonoyl dicyanide (Compound 78)

Step 78-1: Preparation of 5-nitro-1-isopropyl-1H-pyrrolo[2,3-b]pyridine 591 mg (78% yield) of the title compound was obtained by performing a reaction in the same manner as in step 77-1 of Example 77, except that 2-iodopropane (1.10 mL, 11.01 mmol) was used instead of 1-iodopropane.

Step 78-2: Preparation of 1-isopropyl-1H-pyrrolo[2,3-b]pyridin-5-amine 270 mg (54% yield) of the title compound was obtained by performing a reaction in the same manner as in step 72-2 of Example 72, except that 5-nitro-1-isopropyl-1H-pyrrolo[2,3-b]pyridine obtained from step 78-1 was used instead of tert-butyl 5-nitro-1H-pyrrolo[2,3-b]pyridine-1-carboxylate.

Step 78-3: Preparation of (1-isopropyl-1H-pyrrolo[2,3-b]pyridin-5-yl)carbonohydrazonoyl dicyanide 81 mg (21% yield) of the title compound was obtained by performing a reaction in the same manner as in step 1-2 of Example 1, except that 1-isopropyl-1H-pyrrolo[2,3-b]pyridin-5-amine was used instead of 4-(pyrimidin-2-yl)aniline.

Example 79: Preparation of (1-ethyl-1H-pyrrolo[2,3-b]pyridin-5-yl)carbonohydrazonoyl dicyanide (Compound 79)

Step 79-1: Preparation of 1-ethyl-5-nitro-1H-pyrrolo[2,3-b]pyridine 363 mg (52% yield) of the title compound was obtained by performing a reaction in the same manner as in step 77-1 of Example 77, except that iodoethane (0.83 mL, 10.14 mmol) was used instead of 1-iodopropane.

Step 79-2: Preparation of 1-ethyl-1H-pyrrolo[2,3-b]pyridin-5-amine 184 mg (61% yield) of the title compound was obtained by performing a reaction in the same manner as in step 72-2 of Example 72, except that 1-ethyl-5-nitro-1H-pyrrolo[2,3-b]pyridine obtained from step 79-1 was used instead of tert-butyl 5-nitro-1H-pyrrolo[2,3-b]pyridine-1-carboxylate.

Step 79-3: Preparation of (1-ethyl-1H-pyrrolo[2,3-b]pyridin-5-yl)carbonohydrazonoyl dicyanide 187 mg (69% yield) of the title compound was obtained by performing a reaction in the same manner as in step 1-2 of Example 1, except that 1-ethyl-1H-pyrrolo[2,3-b]pyridin-5-amine was used instead of 4-(pyrimidin-2-yl)aniline.

Example 80: Preparation of (1-(2,2,2-trifluoroethyl)-1H-pyrrolo[2,3-b]pyridin-5-yl)carbonohydrazonoyl dicyanide (Compound 80)

Step 80-1: Preparation of 5-nitro-1-(2,2,2-trifluoroethyl)-1H-pyrrolo[2,3-b]pyridine 784 mg (52% yield) of the title compound was obtained by performing a reaction in the same manner as in step 77-1 of Example 77, except that 1,1,1-trifluoro-2-iodoethane (1.80 mL, 18.39 mmol) was used instead of 1-iodopropane.

Step 80-2: Preparation of 1-(2,2,2-trifluoroethyl)-1H-pyrrolo[2,3-b]pyridin-5-amine 235 mg (53% yield) of the title compound was obtained by performing a reaction in the same manner as in step 72-2 of Example 72, except that 5-nitro-1-(2,2,2-trifluoroethyl)-1H-pyrrolo[2,3-b]pyridine obtained from step 80-1 was used instead of tert-butyl 5-nitro-1H-pyrrolo[2,3-b]pyridine-1-carboxylate.

Step 80-3: Preparation of (1-(2,2,2-trifluoroethyl)-1H-pyrrolo[2,3-b]pyridin-5-yl)carbonohydrazonoyl dicyanide 150 mg (55% yield) of the title compound was obtained by performing a reaction in the same manner as in step 1-2 of Example 1, except that 1-(2,2,2-trifluoroethyl)-1H-pyrrolo[2,3-b]pyridin-5-amine was used instead of 4-(pyrimidin-2-yl)aniline.

Example 81: Preparation of (2-methyl-1H-pyrrolo[2,3-b]pyridin-5-yl)carbonohydrazonoyl dicyanide (Compound 81)

Step 81-1: Preparation of tert-butyl 2-methyl-1H-pyrrolo[2,3-b]pyridin-1-carboxylate 1.83 g (98% yield) of the title compound was obtained by performing a reaction in the same manner as in step 72-1 of Example 72, except that 2-methyl-1H-pyrrolo[2,3-b]pyridine was used instead of 5-nitro-1H-pyrrolo[2,3-b]pyridine.

Step 81-2: Preparation of tert-butyl 2-methyl-5-nitro-1H-pyrrolo[2,3-b]pyridin-1-carboxylate tert-Butyl 2-methyl-1H-pyrrolo[2,3-b]pyridine-1-carboxylate and tetrabutylammonium nitrate were dissolved in dichloromethane in the presence of nitrogen, and then stirred at 0° C. for 10 minutes. Thereafter, trifluoroacetic anhydride (TFAA, 1.43 mL, 0.125 mmol) was added, stirring was performed at 0° C. for 5 minutes, and then stirring was further performed at room temperature for 3 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 1.34 g (61% yield) of the title compound.

Step 81-3: Preparation of tert-butyl 5-amino-2-methyl-1H-pyrrolo[2,3-b]pyridine-1-carboxylate 311 mg (58% yield) of the title compound was obtained by performing a reaction in the same manner as in step 72-2 of Example 72, except that tert-butyl 2-methyl-5-nitro-1H-pyrrolo[2,3-b]pyridin-1-carboxylate obtained from step 81-2 was used instead of tert-butyl 5-nitro-1H-pyrrolo[2,3-b]pyridine-1-carboxylate.

Step 81-4: Preparation of tert-butyl 5-(2-(dicyanomethylene)hydrazinyl)-2-methyl-1H-pyrrolo[2,3-b]pyridin-1-carboxylate 160 mg (68% yield) of the title compound was obtained by performing a reaction in the same manner as in step 1-2 of Example 1, except that tert-butyl 5-amino-2-methyl-1H-pyrrolo[2,3-b]pyridine-1-carboxylate was used instead of 4-(pyrimidin-2-yl)aniline.

Step 81-5: Preparation of (2-methyl-1H-pyrrolo[2,3-b]pyridin-5-yl)carbonohydrazonoyl dicyanide 29 mg (71% yield) of the title compound was obtained by performing a reaction in the same manner as in step 58-3 of Example 58, except that tert-butyl 5-(2-(dicyanomethylene)hydrazinyl)-2-methyl-1H-pyrrolo[2,3-b]pyridin-1-ylcarboxylate was used instead of tert-butyl 5-(4-(2-(dicyanomethylene)hydrazinyl)phenyl)-1H-indol-1-ylcarboxylate.

Example 82: Preparation of (3-methyl-1H-pyrrolo[2,3-b]pyridin-5-yl)carbonohydrazonoyl dicyanide (Compound 82)

Step 82-1: Preparation of tert-butyl 3-methyl-1H-pyrrolo[2,3-b]pyridine-1-carboxylate 3.4 g (97% yield) of the title compound was obtained by performing a reaction in the same manner as in step 72-1 of Example 72, except that 3-methyl-1H-pyrrolo[2,3-b]pyridine was used instead of 5-nitro-1H-pyrrolo[2,3-b]pyridine.

Step 82-2: Preparation of tert-butyl 3-methyl-5-nitro-1H-pyrrolo[2,3-b]pyridin-1-carboxylate 800 mg (42% yield) of the title compound was obtained by performing a reaction in the same manner as in step 81-2 of Example 81, except that tert-butyl 3-methyl-1H-pyrrolo[2,3-b]pyridine-1-carboxylate was used instead of tert-butyl 2-methyl-1H-pyrrolo[2,3-b]pyridine-1-carboxylate.

Step 82-3: Preparation of tert-butyl 5-amino-3-methyl-1H-pyrrolo[2,3-b]pyridine-1-carboxylate tert-Butyl 3-methyl-5-nitro-1H-pyrrolo[2,3-b]pyridin-1-carboxylate was dissolved in ethyl acetate and reduced in the same manner as in step 36-2 of Example 36 to obtain 367 mg (82% yield) of the title compound.

Step 82-4: Preparation of tert-butyl 5-(2-(dicyanomethylene)hydrazinyl)-3-methyl-1H-pyrrolo[2,3-b]pyridin-1-carboxylate 106 mg (40% yield) of the title compound was obtained by performing a reaction in the same manner as in step 1-2 of Example 1, except that tert-butyl 5-amino-3-methyl-1H-pyrrolo[2,3-b]pyridine-1-carboxylate was used instead of 4-(pyrimidin-2-yl)aniline.

Step 82-5: Preparation of (3-methyl-1H-pyrrolo[2,3-b]pyridin-5-yl)carbonohydrazonoyl dicyanide 30 mg (88% yield) of the title compound was obtained by performing a reaction in the same manner as in step 58-3 of Example 58, except that tert-butyl 5-(2-(dicyanomethylene) hydrazinyl)-3-methyl-1H-pyrrolo[2,3-b]pyridin-1-ylcarboxylate was used instead of tert-butyl 5-(4-(2-(dicyanomethylene)hydrazinyl)phenyl)-1H-indol-1-ylcarboxylate.

Example 83: Preparation of (3-chloro-1H-pyrrolo[2,3-b]pyridin-5-yl)carbonohydrazonoyl dicyanide (Compound 83)

Step 83-1: Preparation of 3-chloro-5-nitro-1H-pyrrolo[2,3-b]pyridine

5-Nitro-1H-pyrrolo[2,3-b]pyridine and N-chlorosuccinimide were dissolved in DMF (7 mL) in the presence of nitrogen, and then stirred at room temperature for 12 minutes. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 664 mg (55% yield) of the title compound.

Step 83-2: Preparation of tert-butyl 3-chloro-5-nitro-1H-pyrrolo[2,3-b]pyridin-1-carboxylate 419 g (70% yield) of the title compound was obtained by performing a reaction in the same manner as in step 72-1 of Example 72, except that 3-chloro-5-nitro-1H-pyrrolo[2,3-b]pyridine was used instead of 5-nitro-1H-pyrrolo[2,3-b]pyridine.

Step 83-3: Preparation of tert-butyl 5-amino-3-chloro-1H-pyrrolo[2,3-b]pyridin-1-carboxylate tert-Butyl 3-chloro-5-nitro-1H-pyrrolo[2,3-b]pyridin-1-carboxylate was dissolved in ethyl acetate and reduced in the same manner as in step 36-2 of Example 36 to obtain 118 mg (60% yield) of the title compound.

Step 83-4: Preparation of tert-butyl 5-(2-(dicyanomethylene)hydrazinyl)-3-chloro-1H-pyrrolo[2,3-b]pyridin-1-carboxylate 35 mg (23% yield) of the title compound was obtained by performing a reaction in the same manner as in step 1-2 of Example 1, except that tert-butyl 5-amino-3-chloro-1H-pyrrolo[2,3-b]pyridin-1-carboxylate was used instead of 4-(pyrimidin-2-yl)aniline.

Step 83-5: Preparation of (3-chloro-1H-pyrrolo[2,3-b]pyridin-5-yl)carbonohydrazonoyl dicyanide 20 mg (91% yield) of the title compound was obtained by performing a reaction in the same manner as in step 58-3 of Example 58, except that tert-butyl 5-(2-(dicyanomethylene) hydrazinyl)-3-chloro-1H-pyrrolo[2,3-b]pyridin-1-ylcarboxylate was used instead of tert-butyl 5-(4-(2-(dicyanomethylene)hydrazinyl)phenyl)-1H-indol-1-ylcarboxylate.

Example 84: Preparation of (4-methoxy-1H-pyrrolo[2,3-b]pyridin-5-yl)carbonohydrazonoyl dicyanide (Compound 84)

Step 84-1: Preparation of 4-chloro-5-nitro-1-(phenylsulfonyl)-1H-pyrrolo[2,3-b]pyridine 2.0 mg (60% yield) of the title compound was obtained by performing a reaction in the same manner as in step 81-2 of Example 81, except that 4-chloro-1-(phenylsulfonyl)-1H-pyrrolo[2,3-b]pyridine was used instead of tert-butyl 2-methyl-1H-pyrrolo[2,3-b]pyridine-1-carboxylate.

Step 84-2: Preparation of 4-methoxy-5-nitro-1H-pyrrolo[2,3-b]pyridine

4-Chloro-5-nitro-1-(phenylsulfonyl)-1H-pyrrolo[2,3-b]pyridine and solid potassium carbonate were dissolved in a mixed solution of methanol:water=3:1 in the presence of nitrogen and refluxed for 7 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 235 mg (68% yield) of the title compound.

Step 84-3: Preparation of tert-butyl 4-methoxy-5-nitro-1H-pyrrolo[2,3-b]pyridin-1-carboxylate 234 mg (77% yield) of the title compound was obtained by performing a reaction in the same manner as in step 72-1 of Example 72, except that 4-methoxy-5-nitro-1H-pyrrolo[2,3-b]pyridine was used instead of 5-nitro-1H-pyrrolo[2,3-b]pyridine.

Step 84-4: Preparation of tert-butyl 5-amino-4-methoxy-1H-pyrrolo[2,3-b]pyridin-1-carboxylate tert-Butyl 4-methoxy-5-nitro-1H-pyrrolo[2,3-b]pyridin-1-carboxylate was dissolved in ethyl acetate and reduced in the same manner as in step 36-2 of Example 36 to obtain 107 mg (99% yield) of the title compound.

Step 84-5: Preparation of (4-methoxy-1H-pyrrolo[2,3-b]pyridin-5-yl)carbonohydrazonoyl dicyanide 22 mg (17% yield) of the title compound was obtained by performing a reaction in the same manner as in step 1-2 of Example 1, except that tert-butyl 5-amino-4-methoxy-1H-pyrrolo[2,3-b]pyridin-1-carboxylate was used instead of 4-(pyrimidin-2-yl)aniline.

Example 85: Preparation of (2-(dimethylcarbamoyl)-1H-pyrrolo[2,3-b]pyridin-5-yl)carbonohydrazonoyl dicyanide (Compound 85)

Step 85-1: Preparation of N,N-dimethyl-1-(phenylsulfonyl)-1H-pyrrolo[2,3-b]pyridine-2-carboxamide N,N-Diisopropylamine (DIPEA, 1.20 mL, 6.62 mmol) and hexafluorophosphate azabenzotriazole tetramethyl uronium (HATU, 2 g, 4.30 mmol) were added to 1-(phenylsulfonyl)-1H-pyrrolo[2,3-b]pyridine-2-carboxylic acid (1 g, 3.31 mmol) in the presence of nitrogen, and then stirred at room temperature for 10 minutes. Thereafter, a dimethylamine solution (2.0 M in THF, 3.32 mL, 6.62 mmol) was added, followed by stirring at room temperature for 10 minutes. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 800 mg (79% yield) of the title compound.

Step 85-2: Preparation of N,N-dimethyl-5-nitro-1-(phenylsulfonyl)-1H-pyrrolo[2,3-b]pyridine-2-carboxamide 373 mg (41% yield) of the title compound was obtained by performing a reaction in the same manner as in step 81-2 of Example 81, except that N,N-dimethyl-1-(phenylsulfonyl)-1H-pyrrolo[2,3-b]pyridine-2-carboxamide was used instead of tert-butyl 2-methyl-1H-pyrrolo[2,3-b]pyridine-1-carboxylate.

Step 85-3: Preparation of N,N-dimethyl-5-nitro-1H-pyrrolo[2,3-b]pyridine-2-carboxamide N,N-Dimethyl-5-nitro-1-(phenylsulfonyl)-1H-pyrrolo[2,3-b]pyridine-2-carboxamide (0.95 mmol) and solid potassium tert-butoxide (0.95 mmol) were dissolved in dioxane (15 mL) in the presence of nitrogen and stirred at 80° C. for 12 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 71 mg (48% yield) of the title compound.

Step 85-4: Preparation of tert-butyl 2-(dimethylcarbamoyl)-5-nitro-1H-pyrrolo[2,3-b]pyridin-1-carboxylate 100 mg (99% yield) of the title compound was obtained by performing a reaction in the same manner as in step 72-1 of Example 72, except that N,N-dimethyl-5-nitro-1H-pyrrolo[2,3-b]pyridine-2-carboxamide was used instead of 5-nitro-1H-pyrrolo[2,3-b]pyridine.

Step 85-5: Preparation of tert-butyl 5-amino-2-(dimethylcarbamoyl)-1H-pyrrolo[2,3-b]pyridin-1-carboxylate tert-Butyl 2-(dimethylcarbamoyl)-5-nitro-1H-pyrrolo[2,3-b]pyridin-1-carboxylate was dissolved in ethyl acetate and reduced in the same manner as in step 36-2 of Example 36 to obtain 90 mg (97% yield) of the title compound.

Step 85-6: Preparation of tert-butyl 5-(2-(dicyanomethylene)hydrazinyl)-2-(dimethylcarbamoyl)-1H-pyrrolo[2,3-b]pyridin-1-carboxylate 78 mg (69% yield) of the title compound was obtained by performing a reaction in the same manner as in step 1-2 of Example 1, except that tert-butyl 5-amino-2-(dimethylcarbamoyl)-1H-pyrrolo[2,3-b]pyridin-1-carboxylate was used instead of 4-(pyrimidin-2-yl)aniline.

Step 85-7: Preparation of (2-(dimethylcarbamoyl)-1H-pyrrolo[2,3-b]pyridin-5-yl)carbonohydrazonoyl dicyanide 41 mg (72% yield) of the title compound was obtained by performing a reaction in the same manner as in step 58-3 of Example 58, except that tert-butyl 5-(2-(dicyanomethylene)hydrazinyl)-2-(dimethylcarbamoyl)-1H-pyrrolo[2,3-b]pyridin-1-carboxylate was used instead of tert-butyl 5-(4-(2-(dicyanomethylene)hydrazinyl)phenyl)-1H-indol-1-ylcarboxylate.

Example 86: Preparation of (2-(4-methoxybenzamido)benzo[d]thiazol-6-yl)carbonohydrazonoyl dicyanide (Compound 86)

Step 86-1: Preparation of 4-methoxy-N-(6-nitrobenzo[d]thiazol-2-yl)benzamide

4-Methoxybenzoic acid (1 g, 6.57 mmol) was dissolved in MeCN in the presence of nitrogen, and then HATU (2.75 g, 7.23 mmol) and triethylamine (TEA, 1.39 mL, 9.86 mmol) were added to obtain a reaction mixture, and the reaction mixture was stirred at room temperature for 4 hours. Thereafter, 6-nitrobenzo[d]thiazol-2-amine (1.28 g, 6.57 mmol) was added, and the reaction mixture was refluxed for 24 hours. When the reaction was completed, the reaction product was filtered using MeCN to obtain 1.6 g (74% yield) of the title compound as a solid filtrate.

Step 86-2: Preparation of N-(6-aminobenzo[d]thiazol-2-yl)-4-methoxybenzamide

4-Methoxy-N-(6-nitrobenzo[d]thiazol-2-yl)benzamide (100 mg, 0.30 mmol) and 10% Pd/C (64 mg, 0.06 mmol) were dissolved in DMF to obtain a reaction mixture. The reaction mixture was stirred at 60° C. for 2 hours in the presence of hydrogen. When the reaction was completed, the reaction product was filtered using DMF. The filtrate was concentrated under reduced pressure, and the concentrate was solidified with ethyl acetate to obtain 39 mg (43% yield) of the title compound.

Step 86-3: Preparation of (2-(4-methoxybenzamido)benzo[d]thiazol-6-yl)carbonohydrazonoyl dicyanide 78 mg (69% yield) of the title compound was obtained by performing a reaction in the same manner as in step 1-2 of Example 1, except that N-(6-aminobenzo[d]thiazol-2-yl)-4-methoxybenzamide was used instead of 4-(pyrimidin-2-yl)aniline, a mixed solution of ethanol and water of 10:3 was used as a solvent, and a 35% HCl aqueous solution was used as an acidic solution.

Example 87: Preparation of (2-(2-hydroxybenzamido)benzo[d]thiazol-6-yl)carbonohydrazonoyl dicyanide (Compound 87)

Step 87-1: Preparation of N-(6-nitrobenzo[d]thiazol-2-yl)-2-hydroxybenzamide 611 mg (65% yield) of the title compound was obtained by performing a reaction in the same manner as in step 86-1 of Example 86, except that 2-hydroxybenzoic acid (3.62 mmol) was used instead of 4-methoxybenzoic acid.

Step 87-2: Preparation of N-(6-aminobenzo[d]thiazol-2-yl)-2-hydroxybenzamide 48 mg (53% yield) of the title compound was obtained by performing a reaction in the same manner as in step 86-2 of Example 86, except that 2-hydroxy-N-(6-nitrobenzo[d]thiazol-2-yl)benzamide prepared according to step 87-1 was used instead of 4-methoxy-N-(6-nitrobenzo[d]thiazol-2-yl)benzamide.

Step 87-3: Preparation of (2-(2-hydroxybenzamido) benzo[d]thiazol-6-yl)carbonohydrazonoyl dicyanide 36 mg (59% yield) of the title compound was obtained by performing a reaction in the same manner as in step 86-3 of Example 86, except that N-(6-aminobenzo[d]thiazol-2-yl)-2-hydroxybenzamide prepared according to step 87-2 was used instead of N-(6-aminobenzo[d]thiazol-2-yl)-4-methoxybenzamide.

Example 88: Preparation of (2-acetamidobenzo[d] thiazol-6-yl)carbonohydrazonoyl dicyanide (Compound 88)

Step 88-1: Preparation of N-(6-nitrobenzo[d]thiazol-2-yl)acetamide

6-Nitrobenzo[d]thiazol-2-amine was dissolved in MeCN in the presence of nitrogen, and then DIPEA and acetic anhydride were added to obtain a reaction mixture, and the reaction mixture was stirred at 60° C. for 14 hours. When the reaction was completed, the reaction product was filtered using MeCN to obtain 200 mg (75% yield) of the title compound as a solid filtrate.

Step 88-2: Preparation of N-(6-aminobenzo[d]thiazol-2-yl)acetamide 66 mg (83% yield) of the title compound was obtained by performing a reaction in the same manner as in step 86-2 of Example 86, except that N-(6-nitrobenzo[d]thiazol-2-yl)acetamide was used instead of 4-methoxy-N-(6-nitrobenzo[d] thiazol-2-yl)benzamide.

Step 88-3: Preparation of (2-acetamidobenzo[d] thiazol-6-yl)carbonohydrazonoyl dicyanide 28 mg (42% yield) of the title compound was obtained by performing a reaction in the same manner as in step 86-3 of Example 86, except that N-(6-aminobenzo[d]thiazol-2-yl) acetamide was used instead of N-(6-aminobenzo[d]thiazol-2-yl)-4-methoxybenzamide.

Example 89: Preparation of (2-(3-cyanobenzamido) benzo[d]thiazol-6-yl)carbonohydrazonoyl dicyanide (Compound 89)

Step 89-1: Preparation of 3-cyano-N-(6-nitrobenzo [d]thiazol-2-yl)benzamide 718 mg (65% yield) of the title compound was obtained by performing a reaction in the same manner as in step 86-1 of Example 86, except that 3-cyanobenzoic acid (3.62 mmol) was used instead of 4-methoxybenzoic acid.

Step 89-2: Preparation of N-(6-aminobenzo[d]thiazol-2-yl)-3-cyanobenzamide 82 mg (90% yield) of the title compound was obtained by performing a reaction in the same manner as in step 86-2 of Example 86, except that 3-cyano-N-(6-nitrobenzo[d]thiazol-2-yl)benzamide was used instead of 4-methoxy-N-(6-nitrobenzo[d]thiazol-2-yl)benzamide.

Step 89-3: Preparation of (2-(3-cyanobenzamido) benzo[d]thiazol-6-yl)carbonohydrazonoyl dicyanide 33 mg (52% yield) of the title compound was obtained by performing a reaction in the same manner as in step 86-3 of Example 86, except that N-(6-aminobenzo[d]thiazol-2-yl)-3-cyanobenzamide was used instead of N-(6-aminobenzo[d] thiazol-2-yl)-4-methoxybenzamide.

Example 90: Preparation of (2-(5-methylnicotinamido)benzo[d]thiazol-6-yl)carbonohydrazonoyl dicyanide (Compound 90)

Step 90-1: Preparation of 5-methyl-N-(6-nitrobenzo [d]thiazol-2-yl) nicotinamide 1.02 g (88% yield) of the title compound was obtained by performing a reaction in the same manner as in step 86-1 of Example 86, except that 5-methylnicotinic acid (3.65 mmol) was used instead of 4-methoxybenzoic acid.

Step 90-2: Preparation of N-(6-aminobenzo[d]thiazol-2-yl)-5-methylnicotinamide 75 mg (83% yield) of the title compound was obtained by performing a reaction in the same manner as in step 86-2 of Example 86, except that 5-methyl-N-(6-nitrobenzo[d]thiazol-2-yl) nicotinamide was used instead of 4-methoxy-N-(6-nitrobenzo[d]thiazol-2-yl)benzamide.

Step 90-3: Preparation of (2-(5-methylnicotinamido)benzo[d]thiazol-6-yl)carbonohydrazonoyl dicyanide 32 mg (49% yield) of the title compound was obtained by performing a reaction in the same manner as in step 86-3 of Example 86, except that N-(6-aminobenzo[d]thiazol-2-yl)-5-methylnicotinamide prepared according to step 90-2 was used instead of N-(6-aminobenzo[d]thiazol-2-yl)-4-methoxybenzamide.

Example 91: Preparation of (2-(3-hydroxypicolinamido)benzo[d]thiazol-6-yl)carbonohydrazonoyl dicyanide (Compound 91)

Step 91-1: Preparation of 3-hydroxy-N-(6-nitrobenzo[d]thiazol-2-yl)picolinamide 327 mg (72% yield) of the title compound was obtained by performing a reaction in the same manner as in step 86-1 of Example 86, except that 3-hydroxypicolinic acid (1.44 mmol) was used instead of 4-methoxybenzoic acid.

Step 91-2: Preparation of N-(6-aminobenzo[d]thiazol-2-yl)-3-hydroxypicolinamide 46 mg (51% yield) of the title compound was obtained by performing a reaction in the same manner as in step 86-2 of Example 86, except that 3-hydroxy-N-(6-nitrobenzo[d]thiazol-2-yl)picolinamide was used instead of 4-methoxy-N-(6-nitrobenzo[d]thiazol-2-yl)benzamide.

Step 91-3: Preparation of (2-(3-hydroxypicolinamido)benzo[d]thiazol-6-yl)carbonohydrazonoyl dicyanide 22 mg (35% yield) of the title compound was obtained by performing a reaction in the same manner as in step 86-3 of Example 86, except that N-(6-aminobenzo[d]thiazol-2-yl)-3-hydroxypicolinamide prepared according to step 91-2 was used instead of N-(6-aminobenzo[d]thiazol-2-yl)-4-methoxybenzamide.

Example 92: Preparation of (2-(pyrazine-2-carboxamido)benzo[d]thiazol-6-yl)carbonohydrazonoyl dicyanide (Compound 92)

Step 92-1: Preparation of N-(6-nitrobenzo[d]thiazol-2-yl)pyrazine-2-carboxamide 870 mg (71% yield) of the title compound was obtained by performing a reaction in the same manner as in step 86-1 of Example 86, except that pyrazine-2-carboxylic acid (3.65 mmol) was used instead of 4-methoxybenzoic acid.

Step 92-2: Preparation of N-(6-aminobenzo[d]thiazol-2-yl)pyrazine-2-carboxamide 155 mg (87% yield) of the title compound was obtained by performing a reaction in the same manner as in step 86-2 of Example 86, except that N-(6-nitrobenzo[d]thiazol-2-yl)pyrazine-2-carboxamide was used instead of 4-methoxy-N-(6-nitrobenzo[d]thiazol-2-yl)benzamide.

Step 92-3: Preparation of (2-(pyrazine-2-carboxamido)benzo[d]thiazol-6-yl)carbonohydrazonoyl dicyanide 55 mg (43% yield) of the title compound was obtained by performing a reaction in the same manner as in step 86-3 of Example 86, except that N-(6-aminobenzo[d]thiazol-2-yl)pyrazine-2-carboxamide was used instead of N-(6-aminobenzo[d]thiazol-2-yl)-4-methoxybenzamide.

Example 93: Preparation of (2-(5-methylpyrazine-2-carboxamido)benzo[d]thiazol-6-yl)carbonohydrazonoyl dicyanide (Compound 93)

Step 93-1: Preparation of 5-methyl-N-(6-nitrobenzo[d]thiazol-2-yl)pyrazine-2-carboxamide 766 mg (67% yield) of the title compound was obtained by performing a reaction in the same manner as in step 86-1 of Example 86, except that 5-methylpyrazine-2-carboxylic acid (3.65 mmol) was used instead of 4-methoxybenzoic acid.

Step 93-2: Preparation of N-(6-aminobenzo[d]thiazol-2-yl)-5-methylpyrazine-2-carboxamide 165 mg (92% yield) of the title compound was obtained by performing a reaction in the same manner as in step 86-2 of Example 86, except that 5-methyl-N-(6-nitrobenzo[d]thiazol-2-yl)pyrazine-2-carboxamide was used instead of 4-methoxy-N-(6-nitrobenzo[d]thiazol-2-yl)benzamide.

Step 93-3: Preparation of (2-(5-methylpyrazine-2-carboxamido)benzo[d]thiazol-6-yl)carbonohydrazonoyl dicyanide 20 mg (16% yield) of the title compound was obtained by performing a reaction in the same manner as in step 86-3 of Example 86, except that N-(6-aminobenzo[d]thiazol-2-yl)-5-methylpyrazine-2-carboxamide was used instead of N-(6-aminobenzo[d]thiazol-2-yl)-4-methoxybenzamide.

Example 94: Preparation of (2-(pyrimidine-5-carboxamido)benzo[d]thiazol-6-yl)carbonohydrazonoyl dicyanide (Compound 94)

Step 94-1: Preparation of N-(6-nitrobenzo[d]thiazol-2-yl)pyrimidine-5-carboxamide 510 mg (70% yield) of the title compound was obtained by performing a reaction in the same manner as in step 86-1 of Example 86, except that pyrimidine-5-carboxylic acid (3.65 mmol) was used instead of 4-methoxybenzoic acid.

Step 94-2: Preparation of N-(6-aminobenzo[d]thiazol-2-yl)pyrimidine-5-carboxamide 113 mg (83% yield) of the title compound was obtained by performing a reaction in the same manner as in step 86-2 of Example 86, except that N-(6-nitrobenzo[d]thiazol-2-yl)pyrimidine-5-carboxamide was used instead of 4-methoxy-N-(6-nitrobenzo[d]thiazol-2-yl)benzamide.

Step 94-3: Preparation of (2-(pyrimidine-5-carboxamido)benzo[d]thiazol-6-yl)carbonohydrazonoyl dicyanide 15 mg (24% yield) of the title compound was obtained by performing a reaction in the same manner as in step 86-3 of Example 86, except that N-(6-aminobenzo[d]thiazol-2-yl)pyrimidine-5-carboxamide was used instead of N-(6-aminobenzo[d]thiazol-2-yl)-4-methoxybenzamide.

Example 95: Preparation of (2-(2-methylpyrimidine-5-carboxamido)benzo[d]thiazol-6-yl)carbonohydrazonoyl dicyanide (Compound 95)

Step 95-1: Preparation of 2-methyl-N-(6-nitrobenzo[d]thiazol-2-yl)pyrimidine-5-carboxamide 414 mg (61% yield) of the title compound was obtained by performing a reaction in the same manner as in step 86-1 of Example 86, except that 2-methylpyrimidine-5-carboxylic acid (3.65 mmol) was used instead of 4-methoxybenzoic acid.

Step 95-2: Preparation of N-(6-aminobenzo[d]thiazol-2-yl)-2-methylpyrimidine-5-carboxamide 119 mg (88% yield) of the title compound was obtained by performing a reaction in the same manner as in step 86-2 of Example 86, except that 2-methyl-N-(6-nitrobenzo[d]thiazol-2-yl)pyrimidine-5-carboxamide was used instead of 4-methoxy-N-(6-nitrobenzo[d]thiazol-2-yl)benzamide.

Step 95-3: Preparation of (2-(2-methylpyrimidine-5-carboxamido)benzo[d]thiazol-6-yl)carbonohydrazonoyl dicyanide 21 mg (21% yield) of the title compound was obtained by performing a reaction in the same manner as in step 86-3 of Example 86, except that N-(6-aminobenzo[d]thiazol-2-yl)-2-methylpyrimidine-5-carboxamide was used instead of N-(6-aminobenzo[d]thiazol-2-yl)-4-methoxybenzamide.

Example 96: Preparation of (2-(4-methylpyrimidine-5-carboxamido)benzo[d]thiazol-6-yl)carbonohydrazonoyl dicyanide (Compound 96)

Step 96-1: Preparation of 4-methyl-N-(6-nitrobenzo[d]thiazol-2-yl)pyrimidine-5-carboxamide 327 mg (72% yield) of the title compound was obtained by performing a reaction in the same manner as in step 86-1 of Example 86, except that 4-methylpyrimidine-5-carboxylic acid (3.65 mmol) was used instead of 4-methoxybenzoic acid.

Step 96-2: Preparation of N-(6-aminobenzo[d]thiazol-2-yl)-4-methylpyrimidine-5-carboxamide 131 mg (96% yield) of the title compound was obtained by performing a reaction in the same manner as in step 86-2 of Example 86, except that 4-methyl-N-(6-nitrobenzo[d]thiazol-2-yl)pyrimidine-5-carboxamide was used instead of 4-methoxy-N-(6-nitrobenzo[d]thiazol-2-yl)benzamide.

Step 96-3: Preparation of (2-(4-methylpyrimidine-5-carboxamido)benzo[d]thiazol-6-yl)carbonohydrazonoyl dicyanide 28 mg (28% yield) of the title compound was obtained by performing a reaction in the same manner as in step 86-3 of Example 86, except that N-(6-aminobenzo[d]thiazol-2-yl)-4-methylpyrimidine-5-carboxamide was used instead of N-(6-aminobenzo[d]thiazol-2-yl)-4-methoxybenzamide.

Example 97: Preparation of (2-(3-methylpyrazine-2-carboxamido)benzo[d]thiazol-6-yl)carbonohydrazonoyl dicyanide (Compound 97)

Step 97-1: Preparation of 3-methyl-N-(6-nitrobenzo[d]thiazol-2-yl)pyrazine-2-carboxamide 542 mg (79% yield) of the title compound was obtained by performing a reaction in the same manner as in step 86-1 of Example 86, except that 3-methylpyrazine-2-carboxylic acid (3.65 mmol) was used instead of 4-methoxybenzoic acid.

Step 97-2: Preparation of N-(6-aminobenzo[d]thiazol-2-yl)-3-methylpyrazine-2-carboxamide 158 mg (88% yield) of the title compound was obtained by performing a reaction in the same manner as in step 86-2 of Example 86, except that 3-methyl-N-(6-nitrobenzo[d]thiazol-2-yl)pyrazine-2-carboxamide was used instead of 4-methoxy-N-(6-nitrobenzo[d]thiazol-2-yl)benzamide.

Step 97-3: Preparation of (2-(3-methylpyrazine-2-carboxamido)benzo[d]thiazol-6-yl)carbonohydrazonoyl dicyanide 86 mg (68% yield) of the title compound was obtained by performing a reaction in the same manner as in step 86-3 of Example 86, except that N-(6-aminobenzo[d]thiazol-2-yl)-3-methylpyrazine-2-carboxamide was used instead of N-(6-aminobenzo[d]thiazol-2-yl)-4-methoxybenzamide.

Example 98: Preparation of (2-(6-methylpyrazine-2-carboxamido)benzo[d]thiazol-6-yl)carbonohydrazonoyl dicyanide (Compound 98)

Step 98-1: Preparation of 6-methyl-N-(6-nitrobenzo[d]thiazol-2-yl)pyrazine-2-carboxamide 542 mg (79% yield) of the title compound was obtained by performing a reaction in the same manner as in step 86-1 of Example 86, except that 6-methylpyrazine-2-carboxylic acid (3.65 mmol) was used instead of 4-methoxybenzoic acid.

Step 98-2: Preparation of N-(6-aminobenzo[d]thiazol-2-yl)-6-methylpyrazine-2-carboxamide 105 mg (58% yield) of the title compound was obtained by performing a reaction in the same manner as in step 86-2 of Example 86, except that 6-methyl-N-(6-nitrobenzo[d]thiazol-2-yl)pyrazine-2-carboxamide was used instead of 4-methoxy-N-(6-nitrobenzo[d]thiazol-2-yl)benzamide.

Step 98-3: Preparation of (2-(6-methylpyrazine-2-carboxamido)benzo[d]thiazol-6-yl)carbonohydrazonoyl dicyanide 54 mg (53% yield) of the title compound was obtained by performing a reaction in the same manner as in step 86-3 of Example 86, except that N-(6-aminobenzo[d]thiazol-2-yl)-6-methylpyrazine-2-carboxamide was used instead of N-(6-aminobenzo[d]thiazol-2-yl)-4-methoxybenzamide.

Example 99: Preparation of (2-(pyrazine-2-carboxamido)benzo[d]thiazol-5-yl)carbonohydrazonoyl dicyanide (Compound 99)

Step 99-1: Preparation of N-(5-nitrobenzo[d]thiazol-2-yl)pyrazine-2-carboxamide 486 mg (67% yield) of the title compound was obtained by performing a reaction in the same manner as in step 86-1 of Example 86, except that pyrazine-2-carboxylic acid (3.65 mmol) was used instead of 4-methoxybenzoic acid, and 5-nitrobenzo[d]thiazol-2-amine was used instead of 6-nitrobenzo[d]thiazol-2-amine.

Step 99-2: Preparation of N-(5-aminobenzo[d]thiazol-2-yl)pyrazine-2-carboxamide 110 mg (81% yield) of the title compound was obtained by performing a reaction in the same manner as in step 86-2 of Example 86, except that N-(5-nitrobenzo[d]thiazol-2-yl)pyrazine-2-carboxamide was used instead of 4-methoxy-N-(6-nitrobenzo[d]thiazol-2-yl)benzamide.

Step 99-3: Preparation of (2-(pyrazine-2-carboxamido)benzo[d]thiazol-5-yl)carbonohydrazonoyl dicyanide 22 mg (21% yield) of the title compound was obtained by performing a reaction in the same manner as in step 86-3 of Example 86, except that N-(5-aminobenzo[d]thiazol-2-yl)

pyrazine-2-carboxamide was used instead of N-(6-aminobenzo[d]thiazol-2-yl)-4-methoxybenzamide.

Example 100: Preparation of (2-(5-methylpyrazine-2-carboxamido)benzo[d]thiazol-5-yl)carbonohydrazonoyl dicyanide (Compound 100)

Step 100-1: Preparation of 5-methyl-N-(5-nitrobenzo[d]thiazol-2-yl)pyrazine-2-carboxamide 512 mg (75% yield) of the title compound was obtained by performing a reaction in the same manner as in step 86-1 of Example 86, except that 5-methylpyrazine-2-carboxylic acid (3.65 mmol) was used instead of 4-methoxybenzoic acid, and 5-nitrobenzo[d]thiazol-2-amine was used instead of 6-nitrobenzo[d]thiazol-2-amine.

Step 100-2: Preparation of N-(5-aminobenzo[d]thiazol-2-yl)-5-methylpyrazine-2-carboxamide 83 mg (65% yield) of the title compound was obtained by performing a reaction in the same manner as in step 86-2 of Example 86, except that 5-methyl-N-(5-nitrobenzo[d]thiazol-2-yl)pyrazine-2-carboxamide was used instead of 4-methoxy-N-(6-nitrobenzo[d]thiazol-2-yl)benzamide.

Step 100-3: Preparation of (2-(5-methylpyrazine-2-carboxamido)benzo[d]thiazol-5-yl)carbonohydrazonoyl dicyanide 102 mg (80% yield) of the title compound was obtained by performing a reaction in the same manner as in step 86-3 of Example 86, except that N-(5-aminobenzo[d]thiazol-2-yl)-5-methylpyrazine-2-carboxamide was used instead of N-(6-aminobenzo[d]thiazol-2-yl)-4-methoxybenzamide.

Example 101: Preparation of (2-phenylbenzo[d]thiazol-6-yl)carbonohydrazonoyl dicyanide (Compound 101)

Step 101-1: Preparation of 2-bromo-6-nitrobenzo[d]thiazole

6-Nitrobenzo[d]thiazol-2-amine (500 mg, 2.56 mmol) was dissolved in water, and then CuBr (55 mg, 0.38 mmol) and 48% HBr (5 mL) were added to obtain a reaction mixture. Thereafter, sodium nitrite (1.41 g, 20.48 mmol) was added to the reaction mixture at 0° C., and the resulting mixture was stirred at room temperature for 1 hour. When the reaction was completed, the reaction product was extracted using a saturated aqueous NaCl solution and ethyl acetate twice, and moisture was dried with anhydrous magnesium sulfate, followed by filtering. The filtrate was concentrated under reduced pressure, and the concentrate was solidified and filtered by methanol to obtain 564 mg (85% yield) of the title compound in a solid state.

Step 101-2: Preparation of 2-bromo-benzo[d]thiazole-6-amine

2-Bromo-6-nitrobenzo[d]thiazole obtained from step 101-1 and Fe (539 mg, 9.65 mmol) were dissolved in acetic acid to obtain a reaction mixture, and then the reaction mixture was stirred at room temperature for 16 hours. When the reaction was completed, the reaction product was extracted using a saturated aqueous NaCl solution and ethyl acetate twice, and moisture was dried with anhydrous magnesium sulfate, followed by filtering. The filtrate was concentrated under reduced pressure, and the concentrate was purified by column chromatography to obtain 342 mg (69% yield) of the title compound.

Step 101-3: Preparation of 2-phenylbenzo[d]thiazole-6-amine 56 mg (48% yield) of the title compound was obtained by performing a reaction in the same manner as in step 1-1 of Example 1, except that 2-bromobenzo[d]thiazole-6-amine was used instead of 2-bromopyrimidine, phenylboronic acid pinacol ester was used instead of 4-aminophenylboronic acid pinacol ester, and an aqueous potassium carbonate solution was used instead of an aqueous sodium carbonate solution.

Step 101-4: Preparation of (2-phenylbenzo[d]thiazol-6-yl)carbonohydrazonoyl dicyanide 46 mg (76% yield) of the title compound was obtained by performing a reaction in the same manner as in step 86-3 of Example 86, except that 2-phenylbenzo[d]thiazole-6-amine was used instead of N-(6-aminobenzo[d]thiazol-2-yl)-4-methoxybenzamide.

Example 102: Preparation of (2-(4-fluorophenyl)benzo[d]thiazol-6-yl)carbonohydrazonoyl dicyanide (Compound 102)

Step 102-1: Preparation of 2-(4-fluorophenyl)benzo[d]thiazole-6-amine 30 mg (28% yield) of the title compound was obtained by performing a reaction in the same manner as in step 101-3 of Example 101, except that 4-fluorophenylboronic acid pinacol ester was used instead of phenylboronic acid pinacol ester.

Step 102-2: Preparation of (2-(4-fluorophenyl)benzo[d]thiazol-6-yl)carbonohydrazonoyl dicyanide 31 mg (79% yield) of the title compound was obtained by performing a reaction in the same manner as in step 86-3 of Example 86, except that 2-(4-fluorophenyl)benzo[d]thiazole-6-amine was used instead of N-(6-aminobenzo[d]thiazol-2-yl)-4-methoxybenzamide.

Example 103: Preparation of 2-(4-(dimethylamino)phenyl)benzo[d]thiazol-6-yl)carbonohydrazonoyl dicyanide (Compound 103)

Step 103-1: Preparation of 2-(4-(dimethylamino)phenyl)benzo[d]thiazole-6-amine 43 mg (37% yield) of the title compound was obtained by performing a reaction in the same manner as in step 101-3 of Example 101, except that 4-(dimethylamino)phenylboronic acid pinacol ester was used instead of phenylboronic acid pinacol ester.

Step 103-2: Preparation of (2-(4-(dimethylamino)phenyl)benzo[d]thiazol-6-yl)carbonohydrazonoyl dicyanide 31 mg (79% yield) of the title compound was obtained by performing a reaction in the same manner as in step 86-3 of Example 86, except that 2-(4-(dimethylamino)phenyl)benzo[d]thiazole-6-amine was used instead of N-(6-aminobenzo[d]thiazol-2-yl)-4-methoxybenzamide.

Example 104: Preparation of (2-(pyridin-3-yl)benzo[d]thiazol-6-yl)carbonohydrazonoyl dicyanide (Compound 104)

Step 104-1: Preparation of 2-(pyridin-3-yl)benzo[d]thiazole-6-amine hydrochloride A reaction was performed in the same manner as in step 101-3 of Example 101, except that pyridin-3-ylboronic acid pinacol ester was used instead of phenylboronic acid pinacol ester. 48 mg (41% yield) of the title compound in the form of hydrochloride was obtained through a 4 M HCl solution dissolved in dioxane.

Step 104-2: Preparation of (2-(pyridin-3-yl)benzo[d]thiazol-6-yl)carbonohydrazonoyl dicyanide 15 mg (26% yield) of the title compound was obtained by performing a reaction in the same manner as in step 86-3 of Example 86, except that 2-(pyridin-3-yl)benzo[d]thiazole-6-amine hydrochloride was used instead of N-(6-aminobenzo[d]thiazol-2-yl)-4-methoxybenzamide.

Example 105: Preparation of (2-(6-methylpyridin-3-yl)benzo[d]thiazol-6-yl)carbonohydrazonoyl dicyanide (Compound 105)

Step 105-1: Preparation of 2-(6-methylpyridin-3-yl)benzo[d]thiazol-6-amine 68 mg (52% yield) of the title compound was obtained by performing a reaction in the same manner as in step 101-3 of Example 101, except that 6-methylpyridin-3-ylboronic acid pinacol ester was used instead of phenylboronic acid pinacol ester.

Step 105-2: Preparation of (2-(6-methylpyridin-3-yl)benzo[d]thiazol-6-yl)carbonohydrazonoyl dicyanide 6 mg (9% yield) of the title compound was obtained by performing a reaction in the same manner as in step 86-3 of Example 86, except that 2-(6-methylpyridin-3-yl)benzo[d]thiazol-6-amine was used instead of N-(6-aminobenzo[d]thiazol-2-yl)-4-methoxybenzamide.

Example 106: Preparation of (2-(6-fluoropyridin-3-yl)benzo[d]thiazol-6-yl)carbonohydrazonoyl dicyanide (Compound 106)

Step 106-1: Preparation of 2-(6-fluoropyridin-3-yl)benzo[d]thiazol-6-amine 25 mg (23% yield) of the title compound was obtained by performing a reaction in the same manner as in step 101-3 of Example 101, except that 6-fluoropyridin-3-ylboronic acid pinacol ester was used instead of phenylboronic acid pinacol ester.

Step 106-2: Preparation of (2-(6-fluoropyridin-3-yl)benzo[d]thiazol-6-yl)carbonohydrazonoyl dicyanide 22 mg (63% yield) of the title compound was obtained by performing a reaction in the same manner as in step 86-3 of Example 86, except that 2-(6-fluoropyridin-3-yl)benzo[d]thiazol-6-amine was used instead of N-(6-aminobenzo[d]thiazol-2-yl)-4-methoxybenzamide.

Example 107: Preparation of (2-(furan-2-yl)benzo[d]thiazol-6-yl)carbonohydrazonoyl dicyanide (Compound 107)

Step 107-1: Preparation of 2-(furan-2-yl)benzo[d]thiazole-6-amine hydrochloride A reaction was performed in the same manner as in step 101-3 of Example 101, except that furan-2-ylboronic acid pinacol ester was used instead of phenylboronic acid pinacol ester. 68 mg (61% yield) of the title compound in the form of hydrochloride was obtained through a 4 M HCl solution dissolved in dioxane.

Step 107-2: Preparation of (2-(furan-2-yl)benzo[d]thiazol-6-yl)carbonohydrazonoyl dicyanide 53 mg (48% yield) of the title compound was obtained by performing a reaction in the same manner as in step 86-3 of Example 86, except that 2-(furan-2-yl)benzo[d]thiazole-6-amine hydrochloride was used instead of N-(6-aminobenzo[d]thiazol-2-yl)-4-methoxybenzamide.

Example 108: Preparation of (2-(thiophen-2-yl)benzo[d]thiazol-6-yl)carbonohydrazonoyl dicyanide (Compound 108)

Step 108-1: Preparation of 2-(thiophen-2-yl)benzo[d]thiazole-6-amine hydrochloride A reaction was performed in the same manner as in step 101-3 of Example 101, except that thiophene-2-ylboronic acid pinacol ester was used instead of phenylboronic acid pinacol ester. 32 mg (27% yield) of the title compound in the form of hydrochloride was obtained through a 4 M HCl solution dissolved in dioxane.

Step 108-2: Preparation of (2-(thiophen-2-yl)benzo[d]thiazol-6-yl)carbonohydrazonoyl dicyanide 13 mg (27% yield) of the title compound was obtained by performing a reaction in the same manner as in step 86-3 of Example 86, except that 2-(thiophen-2-yl)benzo[d]thiazole-6-amine hydrochloride was used instead of N-(6-aminobenzo[d]thiazol-2-yl)-4-methoxybenzamide.

Example 109: Preparation of (2-(5-fluoropyridin-3-yl)benzo[d]thiazol-6-yl)carbonohydrazonoyl dicyanide (Compound 109)

Step 109-1: Preparation of 2-(5-fluoropyridin-3-yl)benzo[d]thiazol-6-amine hydrochloride A reaction was performed in the same manner as in step 101-3 of Example 101, except that 5-fluoropyridin-3-ylboronic acid pinacol ester was used instead of phenylboronic acid pinacol ester. 56 mg (45% yield) of the title compound in the form of hydrochloride was obtained through a 4 M HCl solution dissolved in dioxane.

Step 109-2: Preparation of (2-(5-fluoropyridin-3-yl)benzo[d]thiazol-6-yl)carbonohydrazonoyl dicyanide 42 mg (57% yield) of the title compound was obtained by performing a reaction in the same manner as in step 86-3 of Example 86, except that 2-(5-fluoropyridin-3-yl)benzo[d]thiazol-6-amine hydrochloride was used instead of N-(6-aminobenzo[d]thiazol-2-yl)-4-methoxybenzamide.

Example 110: Preparation of (2-(5-methylpyridin-3-yl)benzo[d]thiazol-6-yl)carbonohydrazonoyl dicyanide (Compound 110)

Step 110-1: Preparation of 2-(5-methylpyridin-3-yl)benzo[d]thiazol-6-amine hydrochloride A reaction was performed in the same manner as in step 101-3 of Example 101, except that 5-methylpyridin-3-ylboronic acid pinacol ester was used instead of phenylboronic acid pinacol ester. 56 mg (45% yield) of the title compound in the form of hydrochloride was obtained through a 4 M HCl solution dissolved in dioxane.

Step 110-2: Preparation of (2-(5-methylpyridin-3-yl)benzo[d]thiazol-6-yl)carbonohydrazonoyl dicyanide 9 mg (36% yield) of the title compound was obtained by performing a reaction in the same manner as in step 86-3 of Example 86, except that 2-(5-methylpyridin-3-yl)benzo[d]thiazol-6-amine hydrochloride was used instead of N-(6-aminobenzo[d]thiazol-2-yl)-4-methoxybenzamide.

Example 111: Preparation of (2-(pyridin-3-yl)benzo[d]thiazol-5-yl)carbonohydrazonoyl dicyanide (Compound 111)

Step 111-1: Preparation of 2-bromo-5-nitrobenzo[d]thiazole 780 mg (59% yield) of the title compound was obtained by performing a reaction in the same manner as in step 101-1 of Example 101, except that 5-nitrobenzo[d]thiazol-2-amine was used instead of 6-nitrobenzo[d]thiazol-2-amine.

Step 111-2: Preparation of 2-bromo-benzo[d]thiazole-5-amine 153 mg (58% yield) of the title compound was obtained by performing a reaction in the same manner as in step 101-2 of Example 101, except that 2-bromo-5-nitrobenzo[d]thiazole was used instead of 2-bromo-6-nitrobenzo[d]thiazole.

Step 111-3: Preparation of 2-(pyridin-3-yl)benzo[d]thiazol-5-amine 48 mg (48% yield) of the title compound was obtained by performing a reaction in the same manner as in step 101-3 of Example 101, except that 2-bromobenzo[d]thiazol-5-amine was used instead of 2-bromobenzo[d]thiazole-6-amine, and pyridin-3-ylboronic acid pinacol ester was used instead of phenylboronic acid pinacol ester Step 111-4: Preparation (2-(pyridin-3-yl)benzo[d]thiazol-5-yl)carbonohydrazonoyl dicyanide 18 mg (23% yield) of the title compound was obtained by performing a reaction in the same manner as in step 86-3 of Example 86, except that 2-(pyridin-3-yl)benzo[d]thiazol-5-amine was used instead of 2 N-(6-aminobenzo[d]thiazol-2-yl)-4-methoxybenzamide.

Example 112: Preparation of (2-(5-methylpyridin-3-yl)benzo[d]thiazol-5-yl)carbonohydrazonoyl dicyanide (Compound 112)

26 mg (39% yield) of the title compound was obtained by performing a reaction in the same manner as in step 86-3 of Example 86, except that 2-(5-methylpyridin-3-yl)benzo[d]thiazol-5-amine was used instead of N-(6-aminobenzo[d]thiazol-2-yl)-4-methoxybenzamide.

Example 113: Preparation of benzo[d]thiazol-2-ylcarbonohydrazonoyl dicyanide (Compound 113)

29 mg (19% yield) of the title compound was obtained by performing a reaction in the same manner as in step 86-3 of Example 86, except that benzo[d]thiazol-2-amine was used instead of N-(6-aminobenzo[d]thiazol-2-yl)-4-methoxybenzamide, and water was used as a solvent.

Example 114: Preparation of (6-fluorobenzo[d]thiazol-2-yl)carbonohydrazonoyl dicyanide (Compound 114)

29 mg (19% yield) of the title compound was obtained by performing a reaction in the same manner as in Example 113, except that 6-fluorobenzo[d]thiazol-2-amine was used instead of benzo[d]thiazol-2-amine.

Example of (6-chlorobenzo[d]thiazol-2-115: Preparation yl)carbonohydrazonoyl dicyanide (Compound 115)

29 mg (21% yield) of the title compound was obtained by performing a reaction in the same manner as in Example 113, except that 6-chlorobenzo[d]thiazol-2-amine was used instead of benzo[d]thiazol-2-amine.

Example of (6-bromobenzo[d]thiazol-2-116: Preparation yl)carbonohydrazonoyl dicyanide (Compound 116)

23 mg (17% yield) of the title compound was obtained by performing a reaction in the same manner as in Example 113, except that 6-bromobenzo[d]thiazol-2-amine was used instead of benzo[d]thiazol-2-amine.

Example 117: Preparation of (6-(trifluoromethyl)benzo[d]thiazol-2-yl)carbonohydrazonoyl dicyanide (Compound 117)

27 mg (20% yield) of the title compound was obtained by performing a reaction in the same manner as in Example 113, except that 6-(trifluoromethyl)benzo[d]thiazol-2-amine was used instead of benzo[d]thiazol-2-amine.

Example 118: Preparation of (4-chlorobenzo[d]thiazol-2-yl)carbonohydrazonoyl dicyanide (Compound 118)

20 mg (15% yield) of the title compound was obtained by performing a reaction in the same manner as in Example 113, except that 4-chlorobenzo[d]thiazol-2-amine was used instead of benzo[d]thiazol-2-amine.

Example 119: Preparation of (5-chlorobenzo[d]thiazol-2-yl)carbonohydrazonoyl dicyanide (Compound 119)

11 mg (8% yield) of the title compound was obtained by performing a reaction in the same manner as in Example 113, except that 5-chlorobenzo[d]thiazol-2-amine was used instead of benzo[d]thiazol-2-amine.

Example 120: Preparation of (5-bromobenzo[d]thiazol-2-yl)carbonohydrazonoyl dicyanide (Compound 120)

18 mg (7% yield) of the title compound was obtained by performing a reaction in the same manner as in Example 113, except that 5-bromobenzo[d]thiazol-2-amine was used instead of benzo[d]thiazol-2-amine.

Example 121: Preparation of (6-methoxybenzo[d]thiazol-2-yl)carbonohydrazonoyl dicyanide (Compound 121)

26 mg (18% yield) of the title compound was obtained by performing a reaction in the same manner as in Example 113, except that 6-methoxybenzo[d]thiazol-2-amine was used instead of benzo[d]thiazol-2-amine.

Example 122: Preparation of (6-ethoxybenzo[d]thiazol-2-yl)carbonohydrazonoyl dicyanide (Compound 122)

40 mg (29% yield) of the title compound was obtained by performing a reaction in the same manner as in Example 113, except that 6-ethoxybenzo[d]thiazol-2-amine was used instead of benzo[d]thiazol-2-amine.

Example 123: Preparation of (6-(trifluoromethoxy)benzo[d]thiazol-2-yl)carbonohydrazonoyl dicyanide (Compound 123)

15 mg (10% yield) of the title compound was obtained by performing a reaction in the same manner as in Example 113, except that 6-(trifluoromethoxy)benzo[d]thiazol-2-amine was used instead of benzo[d]thiazol-2-amine.

Example 124: Preparation of (6-methylbenzo[d]thiazol-2-yl)carbonohydrazonoyl dicyanide (Compound 124)

36 mg (24% yield) of the title compound was obtained by performing a reaction in the same manner as in Example 113, except that 6-methylbenzo[d]thiazol-2-amine was used instead of benzo[d]thiazol-2-amine.

Example 125: Preparation of (4-methylbenzo[d]thiazol-2-yl)carbonohydrazonoyl dicyanide (Compound 125)

68 mg (46% yield) of the title compound was obtained by performing a reaction in the same manner as in Example 113, except that 4-methylbenzo[d]thiazol-2-amine was used instead of benzo[d]thiazol-2-amine.

Example 126: Preparation of (4,6-dimethylbenzo[d]thiazol-2-yl)carbonohydrazonoyl dicyanide (Compound 126)

41 mg (29% yield) of the title compound was obtained by performing a reaction in the same manner as in Example 113, except that 4,6-dimethylbenzo[d]thiazol-2-amine was used instead of benzo[d]thiazol-2-amine.

Example 127: Preparation of (5,6-dimethylbenzo[d]thiazol-2-yl)carbonohydrazonoyl dicyanide (Compound 127)

32 mg (22% yield) of the title compound was obtained by performing a reaction in the same manner as in Example 113, except that 5,6-dimethylbenzo[d]thiazol-2-amine was used instead of benzo[d]thiazol-2-amine.

Example 128: Preparation of (6-phenoxybenzo[d]thiazol-2-yl)carbonohydrazonoyl dicyanide (Compound 128)

6 mg (4% yield) of the title compound was obtained by performing a reaction in the same manner as in Example 113, except that 6-phenoxybenzo[d]thiazol-2-amine was used instead of benzo[d]thiazol-2-amine.

Example 129: Preparation of (6-phenylbenzo[d]thiazol-2-yl)carbonohydrazonoyl dicyanide (Compound 129)

Step 129-1: Preparation of 6-(4,4,5,5-tetramethyl-1,3,2-dioxaborolan-2-yl)benzo[d]thiazol-2-amine 6-Bromobenzo[d]thiazol-2-amine (50 mg, 0.22 mmol) was dissolved in dioxane in the presence of nitrogen, and then Pd(dppf)$Cl_2$-DCM (36 mg, 0.04 mmol), bis(pinacolato)diboron (84 mg, 0.33 mmol), and potassium acetate (65 mg, 0.66 mmol) were added to obtain a reaction mixture. The reaction mixture was stirred at 90° C. for 3 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 38 mg (62% yield) of the title compound.

Step 129-2: Preparation of 6-phenylbenzo[d]thiazol-2-amine 81 mg (50% yield) of the title compound was obtained by performing a reaction in the same manner as in step 101-3 of Example 101, except that bromobenzene was used instead of 2-bromobenzo[d]thiazole-6-amine, and 2-aminobenzo[d]thiazole-6-ylboronic acid pinacol ester was used instead of phenylboronic acid pinacol ester.

Step 129-3: Preparation of (6-phenylbenzo[d]thiazol-2-yl)carbonohydrazonoyl dicyanide 6 mg (5% yield) of the title compound was obtained by performing a reaction in the same manner as in Example 113, except that 6-phenylbenzo[d]thiazol-2-amine was used instead of benzo[d]thiazol-2-amine.

Example 130: Preparation of (3-(pyrazine-2-carboxamido)benzo[d]isooxazol-5-yl)carbonohydrazonoyl dicyanide (Compound 130)

Step 130-1: Preparation of 5-(tert-butoxycarbonyl)amino-2-fluorobenzonitrile and 5-di(tert-butoxycarbonyl)amino-2-fluorobenzonitrile 5-Amino-2-fluorobenzonitrile (1 g, 7.35 mmol) and DMAP (4-dimethylaminopyridine, 90 mg, 0.74 mmol) were dissolved in DCM in the presence of nitrogen, and then di-tert-butyl dicarbonate ((Boc) 20, 2.4 g, 11.02 mmol) was added to obtain a reaction mixture. The reaction mixture was refluxed for 12 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 1.8 g of the title compounds (5-(tert-butoxycarbonyl)amino-2-fluorobenzonitrile and 5-di(tert-butoxycarbonyl)amino-2-fluorobenzonitrile).

Step 130-2: Preparation of tert-butyl 3-aminobenzo[d]isoxazol-5-ylcarbamate

Potassium carbonate (8.34 g, 60.36 mmol) and acetohydroxamic acid (2.27 g, 30.18 mmol) were dissolved in DCM/$H_2O$ in the presence of nitrogen, and then a mixture (1.44 g) of 5-(tert-butoxycarbonyl)amino-2-fluorobenzonitrile and 5-di(tert-butoxycarbonyl)amino-2-fluorobenzonitrile prepared according to step 130-1 was added to obtain a reaction mixture. The reaction mixture was stirred for 12 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was solidified with ether and then filtered to obtain 743 mg of the title compound.

Step 130-3: Preparation of tert-butyl 3-(pyrazine-2-carboxamido)benzo[d]isoxazol-5-ylcarbamate Pyrazine-2-carboxylic acid (200 mg, 1.61 mmol) was dissolved in DCM in the presence of nitrogen, and then oxalyl chloride (0.25 mL, 2.93 mmol) and a drop of DMF were added to obtain a reaction mixture. The reaction mixture was stirred at room temperature for 2 hours. Thereafter, tert-butyl 3-aminobenzo[d]isoxazol-5-ylcarbamate (365 mg, 1.47 mmol) prepared according to step 130-2 and pyridine were added, and the reaction mixture was stirred for 12 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was solidified with methanol and then filtered to obtain 225 mg (43% yield) of the title compound.

Step 130-4: Preparation of 3-(pyrazine-2-carboxamido)benzo[d]isoxazole-5-ammonium 2,2,2-trifluoroacetate tert-Butyl 3-(pyrazine-2-carboxamido)benzo[d]isoxazol-5-ylcarbamate prepared according to step 130-3 (100 mg, 0.28 mmol) was dissolved in DCM in the presence of nitrogen, and then trifluoroacetic acid (0.43 mL, 5.63 mmol) was added to obtain a reaction mixture. The reaction mixture was stirred at room temperature for 6 hours. When the reaction was completed, the reaction product was concentrated under reduced pressure and then dried for 4 hours. The filtrate was concentrated under reduced pressure, and the concentrate was solidified with methanol and then filtered to obtain 225 mg (43% yield) of the title compound. Thereafter, the concentrate was solidified with ethyl acetate, and then filtered to obtain 97 mg (93% yield) of the title compound.

Step 130-5: Preparation of (3-(pyrazine-2-carboxamido)benzo[d]isooxazol-5-yl)carbonohydrazonoyl dicyanide 29 mg (63% yield) of the title compound was obtained by performing a reaction in the same manner as in step 86-3 of Example 86, except that 3-(pyrazine-2-carboxamido)benzo[d]isoxazole-5-ammonium 2,2,2-trifluoroacetate was used instead of N-(6-aminobenzo[d]thiazol-2-yl)-4-methoxybenzamide.

Example 131: Preparation of (3-(5-methylpyrazine-2-carboxamido)benzo[d]isoxazol-5-yl)carbonohydrazonoyl dicyanide (Compound 131)

Step 131-1: Preparation of tert-butyl 3-(5-methylpyrazine-2-carboxamido)benzo[d]isoxazol-5-ylcarbamate 209 mg (43% yield) of the title compound was obtained by performing a reaction in the same manner as in step 130-3 of Example 130, except that 5-methylpyrazine-2-carboxylic acid was used instead of pyrazine-2-carboxylic acid.

Step 131-2: Preparation of 3-(5-methylpyrazine-2-carboxamido)benzo[d]isoxazole-5-ammonium 2,2,2-trifluoroacetate 84 mg (81% yield) of the title compound was obtained by performing a reaction in the same manner as in step 130-4 of Example 130, except that tert-butyl 3-(5-methylpyrazine-2-carboxamido)benzo[d]isoxazol-5-ylcarbamate was used instead of tert-butyl 3-(pyrazine-2-carboxamido)benzo[d]isoxazol-5-ylcarbamate.

Step 131-3: Preparation of (3-(5-methylpyrazine-2-carboxamido)benzo[d]isooxazol-5-yl)carbonohydrazonoyl dicyanide 34 mg (75% yield) of the title compound was obtained by performing a reaction in the same manner as in step 86-3 of Example 86, except that 3-(5-methylpyrazine-2-carboxamido)benzo[d]isoxazole-5-ammonium 2,2,2-trifluoroacetate was used instead of N-(6-aminobenzo[d]thiazol-2-yl)-4-methoxybenzamide.

Example 132: Preparation of (3-(3-cyanobenzamido)benzo[d]isooxazol-5-yl)carbonohydrazonoyl dicyanide (Compound 132)

Step 132-1: Preparation of tert-butyl 3-(3-cyanobenzamido)benzo[d]isoxazol-5-ylcarbamate 203 mg (43% yield) of the title compound was obtained by performing a reaction in the same manner as in step 130-3 of Example 130, except that 3-cyanobenzoic acid was used instead of pyrazine-2-carboxylic acid.

Step 132-2: Preparation of N-(5-aminobenzo[d]isoxazol-3-yl)-3-cyanobenzamide tert-Butyl 3-(3-cyanobenzamido)benzo[d]isoxazol-5-ylcarbamate prepared according to step 132-1 was dissolved in DCM in the presence of nitrogen, and then trifluoroacetic acid was added to obtain a reaction mixture. The reaction mixture was stirred at room temperature for 6 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure and dried for 4 hours. Thereafter, the concentrate was solidified with ethyl acetate and then filtered to obtain 71 mg (96% yield) of the title compound.

Step 132-3: Preparation of (3-(3-cyanobenzamipyrado)benzo[d]isooxazol-5-yl)carbonohydrazonoyl dicyanide 42 mg (65% yield) of the title compound was obtained by performing a reaction in the same manner as in step 86-3 of Example 86, except that N-(5-aminobenzo[d]isoxazol-3-yl)-3-cyanobenzamide was used instead of N-(6-aminobenzo[d]thiazol-2-yl)-4-methoxybenzamide.

Example 133: Preparation of (3-(4-methoxybenzamido)benzo[d]isooxazol-5-yl)carbonohydrazonoyl dicyanide (Compound 133)

Step 133-1: Preparation of tert-butyl 3-(4-methoxybenzamido)benzo[d]isoxazol-5-ylcarbamate 312 mg (68% yield) of the title compound was obtained by performing a reaction in the same manner as in step 130-3 of Example 130, except that 4-methoxybenzoic acid was used instead of pyrazine-2-carboxylic acid.

Step 133-2: Preparation of N-(5-aminobenzo[d]isoxazol-3-yl)-4-methoxybenzamide 116 mg (78% yield) of the title compound was obtained by performing a reaction in the same manner as in step 132-2 of Example 132, except that tert-butyl 3-(4-methoxybenzamido)benzo[d]isoxazol-5-ylcarbamate was used instead of tert-butyl 3-(3-cyanobenzamido)benzo[d]isoxazol-5-ylcarbamate.

Step 133-3: Preparation of (3-(4-methoxybenzamido)benzo[d]isoxazol-5-yl)carbonohydrazonoyl dicyanide 38 mg (58% yield) of the title compound was obtained by performing a reaction in the same manner as in step 86-3 of Example 86, except that N-(5-aminobenzo[d]isoxazol-3-yl)-4-methoxybenzamide was used instead of N-(6-aminobenzo[d]thiazol-2-yl)-4-methoxybenzamide.

Example 134: Preparation of (2-oxo-2,3-dihydrobenzo[d]thiazol-6-yl)carbonohydrazonoyl dicyanide (Compound 134)

Step 134-1: Preparation of 6-aminobenzo[d]thiazole-2 (3H)-one

6-Nitrobenzo[d]thiazole-2 (3H)-one (200 mg, 1.02 mmol) was dissolved in ethanol/water in the presence of nitrogen, and then Fe (228 mg, 4.08 mmol) and ammonium chloride (545 mg, 10.19 mmol) were added to obtain a reaction mixture. The reaction mixture was stirred at 80° C. for 1 hour. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 83 mg (49% yield) of the title compound.

Step 134-2: Preparation of (2-oxo-2,3-dihydrobenzo[d]thiazol-6-yl)carbonohydrazonoyl dicyanide 34 mg (47% yield) of the title compound was obtained by performing a reaction in the same manner as in step 86-3 of Example 86, except that 6-aminobenzo[d]thiazole-2 (3H)-one was used instead of N-(6-aminobenzo[d]thiazol-2-yl)-4-methoxybenzamide.

Example 135: Preparation of (3-methyl-2-oxo-2,3-dihydrobenzo[d]thiazol-6-yl)carbonohydrazonoyl dicyanide (Compound 135)

Step 135-1: Preparation of 3-methyl-6-nitrobenzo[d]thiazole-2 (3H)-one

6-Nitrobenzo[d]thiazole-2 (3H)-one (100 mg, 0.48 mmol) and 10% Pd/C (101 mg, 0.10 mmol) were dissolved in methanol in the presence of nitrogen, and then methyl iodide (0.05 mL, 0.76 mmol) and DBU (1,8-diazabicyclo[5.4.0]undec-7-ene, 0.11 mL, 0.76 mmol) were added to obtain a reaction mixture. The reaction mixture was stirred at room temperature for 16 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was solidified with methanol to obtain 68 mg (64% yield) of the title compound.

Step 135-2: Preparation of 6-amino-3-methylbenzo[d]thiazole-2 (3H)-one

3-Methyl-6-nitrobenzo[d]thiazole-2 (3H)-one (100 mg, 0.48 mmol) and 10% Pd/C (101 mg, 0.10 mmol) were dissolved in methanol in the presence of nitrogen to obtain a reaction mixture. The reaction mixture was stirred at room temperature for 1 hour in the presence of hydrogen. When the reaction was completed, the reaction product was filtered, and then the filtrate was concentrated under reduced pressure to obtain 79 mg (91% yield) of the title compound.

Step 135-3: Preparation of (3-methyl-2-oxo-2,3-dihydrobenzo[d]thiazol-6-yl)carbonohydrazonoyl dicyanide 94 mg (83% yield) of the title compound was obtained by performing a reaction in the same manner as in step 86-3 of Example 86, except that 6-amino-3-methylbenzo[d]thiazole-2 (3H)-one was used instead of N-(6-aminobenzo[d]thiazol-2-yl)-4-methoxybenzamide.

Example 136: Preparation of (2-methoxybenzo[d]thiazol-6-yl)carbonohydrazonoyl dicyanide (Compound 136)

Step 136-1: Preparation of 2-methoxy-6-nitrobenzo[d]thiazole

60% sodium hydride (45 mg, 1.12 mmol) and methanol (0.05 mL, 1.12 mmol) were dissolved in THF at 0° C. in the presence of nitrogen, and then 2-chloro-6-nitrobenzo[d]thiazole (200 mg, 0.93 mmol) was added to obtain a reaction mixture. The reaction mixture was stirred at room temperature for 1 hour. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 95 mg (49% yield) of the title compound.

Step 136-2: Preparation of 2-methoxybenzo[d]thiazole-6-amine 69 mg (90% yield) of the title compound was obtained by performing a reaction in the same manner as in step 86-3 of Example 86, except that 2-methoxy-6-nitrobenzo[d]thiazole was used instead of 3-methyl-6-nitrobenzo[d]thiazole-2 (3H)-one.

Step 136-3: Preparation of (2-methoxybenzo[d]thiazol-6-yl)carbonohydrazonoyl dicyanide 60 mg (61% yield) of the title compound was obtained by performing a reaction in the same manner as in step 135-2 of Example 135, except that 2-methoxybenzo[d]thiazole-6-amine was used instead of N-(6-aminobenzo[d]thiazol-2-yl)-4-methoxybenzamide.

Example 137: Preparation of (2-oxo-2,3-dihydrobenzo[d]oxazol-6-yl)carbonohydrazonoyl dicyanide (Compound 137)

Step 137-1: Preparation of 6-aminobenzo[d]oxazol-2 (3H)-one 131 mg (78% yield) of the title compound was obtained by performing a reaction in the same manner as in step 135-2 of Example 135, except that 6-nitrobenzo[d]oxazol-2 (3H)-one was used instead of 3-methyl-6-nitrobenzo[d]thiazole-2 (3H)-one.

Step 137-2: Preparation of (2-oxo-2,3-dihydrobenzo[d]oxazol-6-yl)carbonohydrazonoyl dicyanide 115 mg (76% yield) of the title compound was obtained by performing a reaction in the same manner as in step 86-3 of Example 86, except that 6-aminobenzo[d]oxazol-2 (3H)-one was used instead of N-(6-aminobenzo[d]thiazol-2-yl)-4-methoxybenzamide.

Example 138: Preparation of (3-methyl-2-oxo-2,3-dihydrobenzo[d]oxazol-6-yl)carbonohydrazonoyl dicyanide (Compound 138)

Step 138-1: Preparation of 3-methyl-6-nitrobenzo[d]oxazol-2 (3H)-one 111 mg (88% yield) of the title compound was obtained by performing a reaction in the same manner as in step 135-1 of Example 135, except that 6-nitrobenzo[d]oxazol-2 (3H)-one was used instead of 6-nitrobenzo[d]thiazole-2 (3H)-one.

Step 138-2: Preparation of 6-amino-3-methylbenzo[d]oxazol-2 (3H)-one 282 mg (87% yield) of the title compound was obtained by performing a reaction in the same manner as in step 135-2 of Example 135, except that 3-methyl-6-nitrobenzo[d]oxazol-2 (3H)-one was used instead of 3-methyl-6-nitrobenzo[d]thiazole-2 (3H)-one.

Step 138-3: Preparation of (3-methyl-2-oxo-2,3-dihydrobenzo[d]oxazol-6-yl)carbonohydrazonoyl dicyanide 107 mg (73% yield) of the title compound was obtained by performing a reaction in the same manner as in step 86-3 of Example 86, except that 6-amino-3-methylbenzo[d]oxazol-2 (3H)-one was used instead of N-(6-aminobenzo[d]thiazol-2-yl)-4-methoxybenzamide.

Example 139: Preparation of (2-oxo-2,3-dihydro-1H-benzo[d]imidazol-5-yl)carbonohydrazonoyl dicyanide (Compound 139)

Step 139-1: Preparation of 5-amino-1H-benzo[d]imidazol-2 (3H)-one 122 mg (73% yield) of the title compound was obtained by performing a reaction in the same manner as in step 135-2 of Example 135, except that 5-nitro-1H-benzo[d]imidazole-2 (3H)-one was used instead of 3-methyl-6-nitrobenzo[d]thiazole-2 (3H)-one.

Step 139-2: Preparation of (2-oxo-2,3-dihydro-1H-benzo[d]imidazol-5-yl)carbonohydrazonoyl dicyanide 15 mg (10% yield) of the title compound was obtained by performing a reaction in the same manner as in step 86-3 of Example 86, except that 5-amino-1H-benzo[d]imidazol-2 (3H)-one was used instead of N-(6-aminobenzo[d]thiazol-2-yl)-4-methoxybenzamide.

Example 140: Preparation of diethyl 2-(2-(4-(4-methyl-6-oxo-1,4,5,6-tetrahydropyridazin-3-yl)phenyl)hydrazono)malonate (Compound 140)

6-(4-Aminophenyl)-5-methyl-4,5-dihydropyridazine-3 (2H)-one (50 mg, 0.25 mmol) and sodium nitrite (40 mg, 0.29 mmol) were dissolved in ethanol in the presence of nitrogen, and then a 1.0 M aqueous hydrochloric acid solution (0.74 mL, 0.74 mmol) was added to obtain a reaction mixture. The reaction mixture was stirred at 0° C. for 10 minutes to form a diazonium salt. After the diazonium salt was formed, diethylmalonate (80 μL, 0.50 mmol) was added, followed by stirring at room temperature for 10 minutes. Thereafter, the pH of the reaction mixture was adjusted using an aqueous sodium acetate solution, and then the reaction mixture was further stirred at room temperature for 1 hour. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 17 mg (18% yield) of the title compound.

Example 141: Preparation of 2-imino-N'-(4-(4-methyl-6-oxo-1,4,5,6-tetrahydropyridazin-3-yl)phenyl)-2-(piperazin-1-yl)acetohydrazonoyl cyanide (Compound 141)

(4-(4-Methyl-6-oxo-1,4,5,6-tetrahydropyridazin-3-yl)phenyl)carbonohydrazonoyl dicyanide (50 mg, 0.18 mmol)

and piperazine (23 mg, 0.27 mmol) were dissolved in ethanol and then stirred at 80° C. for 17.5 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was solidified with ethanol to obtain 50 mg (76% yield) of the title compound.

Example 142: Preparation of 2-imino-N'-(4-(4-methyl-6-oxo-1,4,5,6-tetrahydropyridazin-3-yl)phenyl)-2-morpholinoacetohydrazonoyl cyanide (Compound 142)

61 mg (93% yield) of the title compound was obtained by performing a reaction in the same manner as in Example 141, except that morpholine was used instead of piperazine.

Example 143: Preparation of methyl 2-(2-(4-(4-methyl-6-oxo-1,4,5,6-tetrahydropyridazin-3-yl)phenyl)hydrazono) propanoate (Compound 143)

6-(4-Aminophenyl)-5-methyl-4,5-dihydropyridazine-3(2H)-one (200 mg, 0.98 mmol), sodium nitrite (81.4 mg, 1.18 mmol), and a 1.0 M aqueous hydrochloric acid solution (2.9 mL, 2.95 mmol) were mixed to obtain a reaction mixture, and the reaction mixture was stirred at 0° C. for 10 minutes. Thereafter, tin (II) chloride hydrate (666 mg, 2.95 mmol) and a 1.0 M aqueous hydrochloric acid solution (0.68 mL) were added, followed by stirring at 0° C. for 10 minutes, and then methylpyruvate (0.18 mL, 1.97 mmol) was added, followed by stirring at room temperature for 30 minutes. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was solidified with ethanol to obtain 177 mg (60% yield) of the title compound.

Example 144: Preparation of methyl-2-cyano-2-(2-(4-(pyrimidin-2-yl)phenyl)hydrazono)acetate (Compound 144)

4-(Pyrimidin-2-yl)aniline (50 mg, 0.29 mmol) and sodium nitrite (24 mg, 0.35 mmol) were dissolved in ethanol in the presence of nitrogen, and then a 1.0 M aqueous hydrochloric acid solution (0.88 mL, 0.88 mmol) was added to obtain a reaction mixture, and the reaction mixture was stirred at 0° C. for 10 minutes. After the diazonium salt was formed, diethylmalonate (80 μL, 0.50 mmol) was added, followed by stirring at room temperature for 10 minutes. Methyl 2-cyanoacetate (31 μL, 0.35 mmol) was added, followed by stirring at room temperature for 10 minutes. The pH of the reaction mixture was adjusted to 6.0 using an aqueous sodium hydroxide solution, and then the reaction mixture was further stirred at room temperature for 1 hour. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 25 mg (64% yield) of the title compound.

Example 145: Preparation of 2-amino-2-oxo-N'-(4-(pyrimidin-2-yl)phenyl)acetohydrazonoyl cyanide (Compound 145)

14 mg (18% yield) of the title compound was obtained by performing a reaction in the same manner as in Example 144, except that 2-cyanoacetamide was used instead of methyl 2-cyanoacetate.

Example 146: Preparation of ethyl-2-cyano-2-(2-(4-(pyrimidin-2-yl)phenyl)hydrazono)acetate (Compound 146)

24 mg (30% yield) of the title compound was obtained by performing a reaction in the same manner as in Example 144, except that 2-cyanoacetamide was used instead of methyl 2-cyanoacetate.

Example 147: Preparation of 2-amino-N'-(4-(pyrimidin-2-yl)phenyl)-2-thioxoacetohydrazonoyl cyanide (Compound 147)

35 mg (43% yield) of the title compound was obtained by performing a reaction in the same manner as in Example 144, except that 2-cyanoethanethioamide was used instead of methyl 2-cyanoacetate.

Example 148: Preparation of 4-methyl-N'-(4-(pyrimidin-2-yl)phenyl) thiazole-2-carbohydrazonoyl cyanide (Compound 148)

Step 148-1: Preparation of 2-(4-methylthiazol-2-yl)acetonitrile

2-Cyanoethanethioamide (500 mg, 4.99 mmol), chloroacetone (0.45 mL, 5.49 mmol), and triethylamine (0.70 mL, 4.99 mmol) were dissolved in dimethylformamide to obtain a reaction mixture, and the reaction mixture was stirred at 40° C. for 1.5 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 163 mg (24% yield) of the title compound.

Step 148-2: Preparation of 4-methyl-N'-(4-(pyrimidin-2-yl)phenyl) thiazole-2-carbohydrazonoyl cyanide 18 mg (19% yield) of the title compound was obtained by performing a reaction in the same manner as in Example 144, except that 2-(4-methylthiazol-2-yl)acetonitrile prepared according to step 148-1 was used instead of 2-cyanoethanethioamide.

Example 149: Preparation of (4-(5-ethynylpyrimidin-2-yl)phenyl)carbohydrazonoyl dicyanide (Compound 149)

Step 149-1: Preparation of 4-(5-bromopyrimidin-2-yl)aniline 2,5-Dibromopyrimidine (2 g, 8.41 mmol) and 4-aminophenylboronic acid pinacol ester (2.3 g, 10.51 mmol) were dissolved in a 1,4-dioxane solution, and then $Pd(PPh_3)$ 4

(484 mg, 0.42 mmol) and a 2.0 M aqueous potassium phosphate solution (12.6 mL, 25.2 mmol) were added to obtain a reaction mixture. The reaction mixture was stirred at 90° C. for 2.5 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 1.8 g (68% yield) of the title compound.

Step 149-2: Preparation of 4-(5-((trimethylsilyl) ethynyl)pyrimidin-2-yl)aniline 4-(5-Bromopyrimidin-2-yl)aniline (220 mg, 0.88 mmol) prepared according to step 149-1 and ethynyltrimethylsilane (1.32 mmol) were dissolved in dimethylformamide, and then $Pd(PPh_3)_2Cl_2$ (31 mg, 0.04 mmol), copper iodide (Cul, 13 mg, 0.07 mmol), and triethylamine (0.3 mL, 2.2 mmol) were added to obtain a reaction mixture. The reaction mixture was stirred at 100° C. for 2 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 148 mg (63% yield) of the title compound.

Step 149-3: Preparation of (4-(5-ethynylpyrimidin-2-yl)phenyl)carbohydrazonoyl dicyanide 92 mg (22% yield) of the title compound was obtained by performing a reaction in the same manner as in Example 144, except that malononitrile was used instead of methyl 2-cyanoacetate, and 4-(5-((trimethylsilyl) ethynyl)pyrimidin-2-yl)aniline prepared according to step 149-2 was used instead of 4-(pyrimidin-2-yl)aniline.

Example 150: Preparation of (4'-(dimethylamino)-3-fluorobiphenyl-4-yl)carbohydrazonoyl dicyanide (Compound 150)

Step 150-1: Preparation of 3'-fluoro-N,N-dimethyl-4'-nitrobiphenyl-4-amine 134 mg (54% yield) of the title compound was obtained by performing a reaction in the same manner as in step 149-1 of Example 149, except that 4-bromo-2-fluoro-1-nitrobenzene was used instead of 2,5-dibromopyrimidine, and 4-dimethylaminophenylboronic acid pinacol ester was used instead of 4-aminophenylboronic acid pinacol ester.

Step 150-2: Preparation of 3-fluoro-$N^{4'}$,$N^{4'}$-dimethylbiphenyl-4,4'-diamine 51 mg (48% yield) of the title compound was obtained by performing a reaction in the same manner as in step 135-2 of Example 135, except that 3'-fluoro-N,N-dimethyl-4'-nitrobiphenyl-4-amine was used instead of 3-methyl-6-nitrobenzo[d]thiazole-2 (3H)-one.

Step 150-3: Preparation of (4'-(dimethylamino)-3-fluorobiphenyl-4-yl)carbohydrazonoyl dicyanide 11 mg (14% yield) of the title compound was obtained by performing a reaction in the same manner as in step 149-3 of Example 149, except that 3-fluoro-$N^{4'}$,$N^{4'}$-dimethylbiphenyl-4,4'-diamine was used instead of 4-(5-((trimethylsilyl) ethynyl)pyrimidin-2-yl)aniline.

Example 151: Preparation of (4'-(dimethylamino) biphenyl-4-yl)carbohydrazonoyl dicyanide (Compound 151)

Step 151-1: Preparation of N,N-dimethyl-4'-nitrobiphenyl-4-amine 182 mg (93% yield) of the title compound was obtained by performing a reaction in the same manner as in step 149-1 of Example 149, except that 4-bromo-1-nitrobenzene was used instead of 2,5-dibromopyrimidine, and 4-dimethylaminophenylboronic acid pinacol ester was used instead of 4-aminophenylboronic acid pinacol ester.

Step 151-2: Preparation of $N^{4'}$, $N^{4'}$-dimethylbiphenyl-4,4'-diamine 51 mg (48% yield) of the title compound was obtained by performing a reaction in the same manner as in step 135-2 of Example 135, except that N,N-dimethyl-4'-nitrobiphenyl-4-amine was used instead of 3-methyl-6-nitrobenzo[d]thiazole-2 (3H)-one.

Step 151-3: Preparation of (4'-(dimethylamino) biphenyl-4-yl)carbohydrazonoyl dicyanide 10 mg (6% yield) of the title compound was obtained by performing a reaction in the same manner as in step 149-3 of Example 149, except that $N^{4'}$, $N^{4'}$-dimethylbiphenyl-4,4'-diamine was used instead of 4-(5-((trimethylsilyl) ethynyl) pyrimidin-2-yl)aniline.

Example 152: Preparation of (4-(6-(dimethylamino) pyridin-3-yl)phenyl)carbohydrazonoyl dicyanide (Compound 152)

Step 152-1: Preparation of 5-(4-aminophenyl)-N,N-dimethylpyridin-2-amine 127 mg (60% yield) of the title compound was obtained by performing a reaction in the same manner as in step 149-1 of Example 149, except that 5-bromo-N,N-dimethylpyridin-2-amine was used instead of 2,5-dibromopyrimidine.

Step 152-2: Preparation of (4-(6-(dimethylamino) pyridin-3-yl)phenyl)carbohydrazonoyl dicyanide 16 mg (38% yield) of the title compound was obtained by performing a reaction in the same manner as in step 149-3 of Example 149, except that 5-(4-aminophenyl)-N,N-dimethylpyridin-2-amine was used instead of 4-(5-((trimethylsilyl) ethynyl)pyrimidin-2-yl)aniline.

Example 153: Preparation of (4-(6-oxo-1,6-dihydropyridazin-3-yl)phenyl)carbohydrazonoyl dicyanide (Compound 153)

Step 153-1: Preparation of 6-chloropyridazine-3 (2H)-one 3,6-Dichloropyridazine (1 g, 6.71 mmol) was dissolved in acetic acid (26 mL) to obtain a reaction mixture, and then the reaction mixture was stirred at 110° C. for 12 hours. When the reaction was completed, the reaction product was concentrated, and an aqueous sodium hydrogen carbonate solution was added, and then the reaction product was stirred at room temperature to be solidified and was concentrated under reduced pressure to obtain 420 mg (48% yield) of the title compound.

Step 153-2: Preparation of 6-(4-aminophenyl)pyridazine-3 (2H)-one

6-Chloropyridazine-3 (2H)-one (100 mg, 0.77 mmol) and 4-aminophenylboronic acid pinacol ester (168 mg, 0.77 mmol) were dissolved in a 1,4-dioxane solution, and then $Pd(PPh_3)_4$ (89 mg, 0.08 mmol) and an aqueous potassium carbonate solution (423 mg, 3.06 mmol) were added to obtain a reaction mixture. The reaction mixture was stirred in a microwave at 160° C. for 1.5 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 36 mg (25% yield) of the title compound.

Step 153-3: Preparation of (4-(6-oxo-1,6-dihydropyridazin-3-yl)phenyl)carbohydrazonoyl dicyanide 96 mg (68% yield) of the title compound was obtained by performing a reaction in the same manner as in step 149-3 of Example 149, except that 6-(4-aminophenyl)pyridazine-3 (2H)-one was used instead of 4-(5-((trimethylsilyl) ethynyl) pyrimidin-2-yl)aniline.

Example 154: Preparation of (4-(4-methyl-6-oxo-1,6-dihydropyridazin-3-yl)phenyl)carbohydrazonoyl dicyanide (Compound 154)

Step 154-1: Preparation of 6-chloro-5-methylpyridazin-3 (2H)-one and 6-chloro-4-methylpyridazin-3 (2H)-one 3,6-Dichloro-4-methylpyridazine (500 mg, 3.07 mmol) was dissolved in acetic acid (13 mL) to obtain a reaction mixture, and then the reaction mixture was stirred at 110° C. for 12 hours. When the reaction was completed, the reaction product was concentrated, and then an aqueous sodium hydrogen carbonate solution was added, and the reaction product was stirred at room temperature. Thereafter, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain the title compounds, 184 mg (41% yield) of 6-chloro-5-methylpyridazine-3 (2H)-one and 31 mg (7% yield) 6-chloro-4-methylpyridazine-3 (2H)-one.

Step 154-2: Preparation of 6-(4-aminophenyl)-5-methylpyridazin-3 (2H)-one 122 mg (44% yield) of the title compound was obtained by performing a reaction in the same manner as in step 153-2 of Example 153, except that a mixture of 6-chloro-5-methylpyridazin-3 (2H)-one and 6-chloro-4-methylpyridazin-3 (2H)-one was used instead of 6-chloropyridazine-3 (2H)-one.

Step 154-3: Preparation of (4-(4-methyl-6-oxo-1,6-dihydropyridazin-3-yl)phenyl)carbohydrazonoyl dicyanide 96 mg (70% yield) of the title compound was obtained by performing a reaction in the same manner as in step 149-3 of Example 149, except that 6-(4-aminophenyl)-5-methylpyridazin-3 (2H)-one was used instead of 4-(5-((trimethylsilyl) ethynyl)pyrimidin-2-yl)aniline.

Example 155: Preparation of (4-(5-methyl-6-oxo-1,6-dihydropyridazin-3-yl)phenyl)carbohydrazonoyl dicyanide (Compound 155)

Step 155-1: Preparation of 6-(4-aminophenyl)-4-methylpyridazin-3 (2H)-one 87 mg (62% yield) of the title compound was obtained by performing a reaction in the same manner as in step 153-2 of Example 153, except that a mixture of 6-chloro-5-methylpyridazin-3 (2H)-one and 6-chloro-4-methylpyridazin-3 (2H)-one was used instead of 6-chloropyridazine-3 (2H)-one.

Step 155-2: Preparation of (4-(5-methyl-6-oxo-1,6-dihydropyridazin-3-yl)phenyl)carbohydrazonoyl dicyanide 60 mg (87% yield) of the title compound was obtained by performing a reaction in the same manner as in step 149-3 of Example 149, except that 6-(4-aminophenyl)-4-methylpyridazin-3 (2H)-one was used instead of 4-(5-((trimethylsilyl) ethynyl)pyrimidin-2-yl)aniline.

Example 156: Preparation of (4-(1-methyl-6-oxo-1,6-dihydropyridazin-3-yl)phenyl)carbohydrazonoyl dicyanide (Compound 156)

Step 156-1: Preparation of 6-chloro-2-methylpyridazin-3 (2H)-one

6-Chloropyridazine-3 (2H)-one (100 mg, 0.77 mmol), methyl iodide (95 μL, 1.53 mmol), and potassium carbonate (212 mg, 1.53 mmol) were dissolved in dimethylformamide to obtain a reaction mixture, and then the reaction mixture was stirred at room temperature for 4 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 82 mg (74% yield) of the title compound.

Step 156-2: Preparation of 6-(4-aminophenyl)-2-methylpyridazin-3 (2H)-one 86 mg (95% yield) of the title compound was obtained by performing a reaction in the same manner as in step 153-2 of Example 153, except that 6-chloro-2-methylpyridazin-3 (2H)-one was used instead of 6-chloropyridazine-3 (2H)-one.

Step 156-3: Preparation of (4-(1-methyl-6-oxo-1,6-dihydropyridazin-3-yl)phenyl)carbohydrazonoyl dicyanide 41 mg (59% yield) of the title compound was obtained by performing a reaction in the same manner as in step 149-3 of Example 149, except that 6-(4-aminophenyl)-2-methylpyridazin-3 (2H)-one was used instead of 4-(5-((trimethylsilyl) ethynyl)pyrimidin-2-yl)aniline.

Example 157: Preparation of (4-(1,4-dimethyl-6-oxo-1,6-dihydropyridazin-3-yl)phenyl)carbohydrazonoyl dicyanide (Compound 157)

Step 157-1: Preparation of 6-chloro-2,5-dimethylpyridazine-3 (2H)-one 53 mg (49% yield) of the title compound was obtained by performing a reaction in the same manner as in step 156-1 of Example 156, except that 6-chloro-5-methylpyridazin-3 (2H)-one was used instead of 6-chloropyridazine-3 (2H)-one.

Step 157-2: Preparation of 6-(4-aminophenyl)-2,5-dimethylpyridazine-3 (2H)-one 51 mg (76% yield) of the title compound was obtained by performing a reaction in the same manner as in step 153-2 of Example 153, except that 6-chloro-2,5-dimethylpyridazine-3 (2H)-one was used instead of 6-chloropyridazine-3 (2H)-one.

Step 157-3: Preparation of (4-(1,4-dimethyl-6-oxo-1,6-dihydropyridazin-3-yl)phenyl)carbohydrazonoyl dicyanide 37 mg (77% yield) of the title compound was obtained by performing a reaction in the same manner as in step 149-3 of Example 149, except that 6-(4-aminophenyl)-2,5-dimethylpyridazine-3 (2H)-one was used instead of 4-(5-((trimethylsilyl) ethynyl)pyrimidin-2-yl)aniline.

Example 158: Preparation of (4-(1,5-dimethyl-6-oxo-1,6-dihydropyridazin-3-yl)phenyl)carbohydrazonoyl dicyanide (Compound 158)

Step 158-1: Preparation of 6-chloro-2,4-dimethylpyridazine-3 (2H)-one 50 mg (65% yield) of the title compound was obtained by performing a reaction in the same manner as in step 156-1 of Example 156, except that 6-chloro-4-methylpyridazin-3 (2H)-one was used instead of 6-chloropyridazine-3 (2H)-one.

Step 158-2: Preparation of 6-(4-aminophenyl)-2,4-dimethylpyridazine-3 (2H)-one 47 mg (70% yield) of the title compound was obtained by performing a reaction in the same manner as in step 153-2 of Example 153, except that 6-chloro-2,4-dimethylpyridazine-3 (2H)-one was used instead of 6-chloropyridazine-3 (2H)-one.

Step 158-3: Preparation of (4-(1,5-dimethyl-6-oxo-1,6-dihydropyridazin-3-yl)phenyl)carbohydrazonoyl dicyanide 11 mg (22% yield) of the title compound was obtained by performing a reaction in the same manner as in step 149-3 of Example 149, except that 6-(4-aminophenyl)-2,4-dimethylpyridazine-3 (2H)-one was used instead of 4-(5-((trimethylsilyl) ethynyl)pyrimidin-2-yl)aniline.

Example 159: Preparation of (3-isopropyl-2-oxo-2,3-dihydrobenzo[d]thiazol-6-yl)carbohydrazonoyl dicyanide (Compound 159)

Step 159-1: Preparation of 3-isopropyl-6-nitrobenzo[d]thiazole-2 (3H)-one 162 mg (44% yield) of the title compound was obtained by performing a reaction in the same manner as in step 135-1 of Example 135, except that 2-iodopropane was used instead of methyl iodide.

Step 159-2: Preparation of 6-amino-3-isopropylbenzo[d]thiazole-2 (3H)-one 112 mg (85% yield) of the title compound was obtained by performing a reaction in the same manner as in step 135-2 of Example 135, except that 3-isopropyl-6-nitrobenzo[d]thiazole-2 (3H)-one was used instead of 3-methyl-6-nitrobenzo[d]thiazole-2 (3H)-one.

Step 159-3: Preparation of (3-isopropyl-2-oxo-2,3-dihydrobenzo[d]thiazol-6-yl)carbonohydrazonoyl dicyanide 109 mg (80% yield) of the title compound was obtained by performing a reaction in the same manner as in step 86-3 of Example 86, except that 6-amino-3-isopropylbenzo[d]thiazole-2 (3H)-one was used instead of N-(6-aminobenzo[d]thiazol-2-yl)-4-methoxybenzamide.

Example 160: Preparation of (3-(difluoromethyl)-2-oxo-2,3-dihydrobenzo[d]thiazol-6-yl)carbohydrazonoyl dicyanide (Compound 160)

Step 160-1: Preparation of 3-(difluoromethyl)-6-nitrobenzo[d]thiazole-2 (3H)-one 6-Nitrobenzo[d]thiazole-2 (3H)-one (300 mg, 1.53 mmol) was dissolved in DMF in the presence of nitrogen, and then sodium 2-chloro-2,2-difluoroacetate (467 mg, 3.06 mmol) and DBU (0.46 mL, 3.06 mmol) were added to obtain a reaction mixture, and the reaction mixture was stirred at room temperature for 16 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was solidified with methanol to obtain 176 mg (47% yield) of the title compound.

Step 160-2: Preparation of 6-amino-3-(difluoromethyl)benzo[d]thiazole-2 (3H)-one 125 mg (95% yield) of the title compound was obtained by performing a reaction in the same manner as in step 135-2 of Example 135, except that 3-(difluoromethyl)-6-nitrobenzo[d]thiazole-2 (3H)-one was used instead of 3-methyl-6-nitrobenzo[d]thiazole-2 (3H)-one.

Step 160-3: Preparation of (3-(difluoromethyl)-2-oxo-2,3-dihydrobenzo[d]thiazol-6-yl)carbonohydrazonoyl dicyanide 85 mg (63% yield) of the title compound was obtained by performing a reaction in the same manner as in step 86-3 of Example 86, except that 6-amino-3-(difluoromethyl)benzo[d]thiazole-2 (3H)-one was used instead of N-(6-aminobenzo[d]thiazol-2-yl)-4-methoxybenzamide.

Example 161: Preparation of (2-isopropoxybenzo[d]thiazol-6-yl)carbohydrazonoyl dicyanide (Compound 161)

Step 161-1: Preparation of 2-isopropoxy-6-nitrobenzo[d]thiazole

60% sodium hydride (84 mg, 2.10 mmol) and isopropanol (0.16 mL, 2.10 mmol) were dissolved in THF at 0° C. in the presence of nitrogen, and then 2-chloro-6-nitrobenzo[d]thiazole (300 mg, 1.40 mmol) was added to obtain a reaction mixture, and the reaction mixture was stirred at room temperature for 1 hour. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 184 mg (55% yield) of the title compound.

Step 161-2: Preparation of 2-isopropoxybenzo[d]thiazole-6-amine 126 mg (96% yield) of the title compound was obtained by performing a reaction in the same manner as in step 135-2 of Example 135, except that 2-isopropoxy-6-nitrobenzo[d]thiazole was used instead of 3-methyl-6-nitrobenzo[d]thiazole-2 (3H)-one.

Step 161-3: Preparation of (2-isopropoxybenzo[d]thiazol-6-yl)carbonohydrazonoyl dicyanide 30 mg (22% yield) of the title compound was obtained by performing a reaction in the same manner as in step 86-3 of Example 86, except that 2-isopropoxybenzo[d]thiazole-6-amine of was used instead N-(6-aminobenzo[d]thiazol-2-yl)-4-methoxybenzamide.

Example 162: Preparation of (3-isopropyl-2-oxo-2,3-dihydrobenzo[d]oxazol-6-yl)carbohydrazonoyl dicyanide (Compound 162)

Step 162-1: Preparation of 3-isopropyl-6-nitrobenzo[d]oxazol-2 (3H)-one 201 mg (54% yield) of the title compound was obtained by performing a reaction in the same manner as in step 135-1 of Example 135, except that 6-nitrobenzo[d]oxazol-2 (3H)-one was used instead of 6-nitrobenzo[d]thiazole-2 (3H)-one, and 2-iodopropane was used instead of methyl iodide.

Step 162-2: Preparation of 6-amino-3-isopropylbenzo[d]oxazol-2 (3H)-one 124 mg (85% yield) of the title compound was obtained by performing a reaction in the same manner as in step 135-2 of Example 135, except that 3-isopropyl-6-nitrobenzo[d]thiazole-2 (3H)-one was used instead of 3-methyl-6-nitrobenzo[d]thiazole-2 (3H)-one.

Step 162-3: Preparation of (3-isopropyl-2-oxo-2,3-dihydrobenzo[d]oxazol-6-yl)carbonohydrazonoyl dicyanide 99 mg (59% yield) of the title compound was obtained by performing a reaction in the same manner as in step 86-3 of Example 86, except that 6-amino-3-isopropylbenzo[d]oxazol-2 (3H)-one was used instead of N-(6-aminobenzo[d]thiazol-2-yl)-4-methoxybenzamide.

Example 163: Preparation of (3-(difluoromethyl)-2-oxo-2,3-dihydrobenzo[d]oxazol-6-yl)carbohydrazonoyl dicyanide (Compound 163)

Step 163-1: Preparation of 3-(difluoromethyl)-6-nitrobenzo[d]oxazol-2 (3H)-one 144 mg (38% yield) of the title compound was obtained by performing a reaction in the same manner as in step 160-1 of Example 160, except that 6-nitrobenzo[d]oxazol-2 (3H)-one was used instead of 6-nitrobenzo[d]thiazole-2 (3H)-one.

Step 163-2: Preparation of 6-amino-3-(difluoromethyl)benzo[d]oxazol-2 (3H)-one 110 mg (98% yield) of the title compound was obtained by performing a reaction in the same manner as in step 135-2 of Example 135, except that 3-(difluoromethyl)-6-nitrobenzo[d]oxazol-2 (3H)-one was used instead of 3-methyl-6-nitrobenzo[d]thiazole-2 (3H)-one.

Step 163-3: Preparation of (3-(difluoromethyl)-2-oxo-2,3-dihydrobenzo[d]oxazol-6-yl)carbonohydrazonoyl dicyanide 85 mg (63% yield) of the title compound was obtained by performing a reaction in the same manner as in step 86-3 of Example 86, except that 6-amino-3-(difluoromethyl)benzo[d]oxazol-2 (3H)-one was used instead of N-(6-aminobenzo[d]thiazol-2-yl)-4-methoxybenzamide.

Example 164: Preparation of (1,3-dimethyl-2-oxo-2,3-dihydro-1H-benzo[d]imidazol-5-yl)carbohydrazonoyl dicyanide (Compound 164)

Step 164-1: Preparation of 1,3-dimethyl-5-nitro-1H-benzo[d]imidazole-2 (3H)-one 207 mg (64% yield) of the title compound was obtained by performing a reaction in the same manner as in step 135-1 of Example 135, except that 5-nitro-1H-benzo[d]imidazole-2 (3H)-one was used instead of 6-nitrobenzo[d]thiazole-2 (3H)-one.

Step 164-2: Preparation of 5-amino-1,3-dimethyl-1H-benzo[d]imidazol-2 (3H)-one 105 mg (82% yield) of the title compound was obtained by performing a reaction in the same manner as in step 135-2 of Example 135, except that 1,3-dimethyl-5-nitro-1H-benzo[d]imidazole-2 (3H)-one was used instead of 3-methyl-6-nitrobenzo[d]thiazole-2 (3H)-one.

Step 164-3: Preparation of (1,3-dimethyl-2-oxo-2,3-dihydro-1H-benzo[d]imidazol-5-yl)carbonohydrazonoyl dicyanide 11 mg (8% yield) of the title compound was obtained by performing a reaction in the same manner as in step 86-3 of Example 86, except that 5-amino-1,3-dimethyl-1H-benzo[d]imidazol-2 (3H)-one was used instead of N-(6-aminobenzo[d]thiazol-2-yl)-4-methoxybenzamide.

Example 165: Preparation of (1,3-diisopropyl-2-oxo-2,3-dihydro-1H-benzo[d]imidazol-5-yl)carbohydrazonoyl dicyanide (Compound 165)

Step 165-1: Preparation of 1,3-diisopropyl-5-nitro-1H-benzo[d]imidazole-2 (3H)-one 204 mg (46% yield) of the title compound was obtained by performing a reaction in the same manner as in step 135-1 of Example 135, except that 5-nitro-1H-benzo[d]imidazole-2 (3H)-one was used instead of 6-nitrobenzo[d]thiazole-2 (3H)-one, and 2-iodopropane was used instead of methyl iodide.

Step 165-2: Preparation of 5-amino-1,3-diisopropyl-1H-benzo[d]imidazole-2 (3H)-one 118 mg (89% yield) of the title compound was obtained by performing a reaction in the same manner as in step 135-2 of Example 135, except that 1,3-diisopropyl-5-nitro-1H-benzo[d]imidazole-2 (3H)-one was used instead of 3-methyl-6-nitrobenzo[d]thiazole-2 (3H)-one.

Step 165-3: Preparation of (1,3-dimethyl-2-oxo-2,3-dihydro-1H-benzo[d]imidazol-5-yl)carbonohydrazonoyl dicyanide 12 mg (10% yield) of the title compound was obtained by performing a reaction in the same manner as in step 86-3 of Example 86, except that 5-amino-1,3-diisopropyl-1H-benzo[d]imidazole-2 (3H)-one was used instead of N-(6-aminobenzo[d]thiazol-2-yl)-4-methoxybenzamide.

Example 166: Preparation of (1,3-bis(difluoromethyl)-2-oxo-2,3-dihydro-1H-benzo[d]imidazol-5-yl)carbohydrazonoyl dicyanide (Compound 166)

Step 166-1: Preparation of 1,3-bis(difluoromethyl)-5-nitro-1H-benzo[d]imidazol-2 (3H)-one 179 mg (38% yield) of the title compound was obtained by performing a reaction in the same manner as in step 160-1 of Example 160, except that 5-nitro-1H-benzo[d]imidazole-2 (3H)-one was used instead of 6-nitrobenzo[d]thiazole-2 (3H)-one.

Step 166-2: Preparation of 5-amino-1,3-bis(difluoromethyl)-1H-benzo[d]imidazol-2 (3H)-one 69 mg (96% yield) of the title compound was obtained by performing a reaction in the same manner as in step 135-2 of Example 135, except that 1,3-bis(difluoromethyl)-6-nitro-1H-benzo[d]imidazole-2 (3H)-one was used instead of 3-methyl-6-nitrobenzo[d]thiazole-2 (3H)-one.

Step 166-3: Preparation of (1,3-bis(difluoromethyl)-2-oxo-2,3-dihydro-1H-benzo[d]imidazol-5-yl)carbonohydrazonoyl dicyanide 45 mg (58% yield) of the title compound was obtained by performing a reaction in the same manner as in step 86-3 of Example 86, except that 5-amino-1,3-bis(difluoromethyl)-1H-benzo[d]imidazol-2 (3H)-one was used instead of N-(6-aminobenzo[d]thiazol-2-yl)-4-methoxybenzamide.

Example 167: Preparation of (2-(methylamino)benzo[d]thiazol-6-yl)carbohydrazonoyl dicyanide (Compound 167)

Step 167-1: Preparation of N-methyl-6-nitrobenzo[d]thiazol-2-amine

2-Chloro-6-nitrobenzo[d]thiazole (500 mg, 2.33 mmol) was dissolved in THF at room temperature in the presence of nitrogen, and then 2.0 M methylamine (2.56 mL, 5.13 mmol) dissolved in THF was added to obtain a reaction mixture, and the reaction mixture was stirred at room temperature for 15 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was solidified with ethyl acetate to obtain 442 mg (91% yield) of the title compound.

Step 167-2: Preparation of $N^2$-methylbenzo[d]thiazole-2,6-diamine 101 mg (78% yield) of the title compound was obtained by performing a reaction in the same manner as in step 135-2 of Example 135, except that N-methyl-6-nitrobenzo[d]thiazol-2-amine was used instead of 3-methyl-6-nitrobenzo[d]thiazole-2 (3H)-one.

Step 167-3: Preparation of (2-(methylamino)benzo[d]thiazol-6-yl)carbonohydrazonoyl dicyanide 5 mg (4% yield) of the title compound was obtained by performing a reaction in the same manner as in Example 113, except that NR-methylbenzo[d]thiazole-2,6-diamine was used instead of benzo[d]thiazol-2-amine.

Example 168: Preparation of (2-(dimethylamino)benzo[d]thiazol-6-yl)carbohydrazonoyl dicyanide (Compound 168)

Step 168-1: Preparation of N,N-dimethyl-6-nitrobenzo[d]thiazol-2-amine 392 mg (75% yield) of the title compound was obtained by performing a reaction in the same manner as in step 167-1 of Example 167, except that dimethylamine was used instead of methylamine.

Step 168-2: Preparation of $N^2$,$N^2$-dimethylbenzo[d]thiazole-2,6-diamine 103 mg (80% yield) of the title compound was obtained by performing a reaction in the same manner as in step 135-2 of Example 135, except that N,N-dimethyl-6-nitrobenzo[d]thiazol-2-amine was used instead of 3-methyl-6-nitrobenzo[d]thiazole-2 (3H)-one.

Step 168-3: Preparation of (2-(dimethylamino)benzo[d]thiazol-6-yl)carbonohydrazonoyl dicyanide 11 mg (10% yield) of the title compound was obtained by performing a reaction in the same manner as in Example 113, except that $N^2$,$N^2$-dimethylbenzo[d]thiazole-2,6-diamine was used instead of benzo[d]thiazol-2-amine.

Example 169: Preparation of (4-(6-oxo-1,4,5,6-tetrahydropyridazin-3-yl)phenyl)carbohydrazonoyl dicyanide (Compound 169)

Step 169-1: Preparation of N-(4-(6-oxo-1,4,5,6-tetrahydropyridazin-3yl)phenyl)acetamide 4-(4-Acetamidophenyl)-4-oxobutanoic acid (100 mg, 0.42 mmol) was dissolved in ethanol, and then hydrazine hydrate (25 μL, 0.51 mmol) was added to obtain a reaction mixture, and the reaction mixture was stirred at 90° C. for 3.5 hours. When the reaction was completed, the reaction product was filtered to obtain 47 mg (48% yield) of the title compound.

Step 169-2: Preparation of 6-(4-aminophenyl)-4,5-dihydropyridazine-3 (2H)-one 1.0 M aqueous hydrochloric acid solution (21.6 mL, 21.6 mmol) was added to N-(4-(6-oxo-1,4,5,6-tetrahydropyridazin-3yl)phenyl)acetamide prepared according to step 169-1 and then reacted at 110° C. for 1.5 hours. Thereafter, the reaction product was neutralized using an aqueous ammonium hydroxide solution and filtered to obtain 118 mg (28% yield) of the title compound.

Step 169-3: Preparation of (4-(6-oxo-1,4,5,6-tetrahydropyridazin-3-yl)phenyl)carbohydrazonoyl dicyanide 66 mg (93% yield) of the title compound was obtained by performing a reaction in the same manner as in step 149-3 of Example 149, except that 6-(4-aminophenyl)-4,5-dihydropyridazine-3 (2H)-one was used instead of 4-(5-((trimethylsilyl) ethynyl)pyrimidin-2-yl)aniline.

Example 170: Preparation of (4-(1-methyl-6-oxo-1,4,5,6-tetrahydropyridazin-3-yl)phenyl)carbohydrazonoyl dicyanide (Compound 170)

Step 170-1: Preparation of 6-(4-aminophenyl)-2-methyl-4,5-dihydropyridazine-3 (2H)-one 6-(4-Aminophenyl)-4,5-dihydropyridazine-3 (2H)-one (105 mg, 0.55 mmol) and 60% sodium hydride (24 mg, 0.61 mmol) were dissolved in a mixed solvent of DMF and THF, and then methyl iodide (34 μL, 0.55 mmol) was added to obtain a reaction mixture, and the reaction mixture was stirred at 0° C. for 12 hours. When the reaction was completed, the reaction product was extracted using distilled water and ethyl acetate to obtain an organic layer, and the organic layer was dried over anhydrous magnesium sulfate and then filtered. The filtrate was concentrated under reduced pressure, and the concentrate was purified by column chromatography to obtain 33 mg (29% yield) of the title compound.

Step 170-2: Preparation of (4-(1-methyl-6-oxo-1,4,5,6-tetrahydropyridazin-3-yl)phenyl)carbohydrazonoyl dicyanide 90 mg (95% yield) of the title compound was obtained by performing a reaction in the same manner as in step 149-3 of Example 149, except that 6-(4-aminophenyl)-2-methyl-4,5-dihydropyridazine-3 (2H)-one was used instead of 4-(5-((trimethylsilyl) ethynyl)pyrimidin-2-yl)aniline.

Example 171: Preparation of (4-(1,4-dimethyl-6-oxo-1,4,5,6-tetrahydropyridazin-3-yl)phenyl)carbohydrazonoyl dicyanide (Compound 171)

Step 171-1: Preparation of 6-(4-aminophenyl)-2,5-dimethyl-4,5-dihydropyridazine-3 (2H)-one 131 mg (61% yield) of the title compound was obtained by performing a reaction in the same manner as in step 170-1 of Example 170, except that 6-(4-aminophenyl)-5-methyl-4,5-dihydropyridazine-3 (2H)-one was used instead of 6-(4-aminophenyl)-4,5-dihydropyridazine-3 (2H)-one.

Step 171-2: Preparation of (4-(1,4-dimethyl-6-oxo-1,4,5,6-tetrahydropyridazin-3-yl)phenyl)carbohydrazonoyl dicyanide 82 mg (76% yield) of the title compound was obtained by performing a reaction in the same manner as in step 149-3 of Example 149, except that 6-(4-aminophenyl)-2,5-dimethyl-4,5-dihydropyridazine-3 (2H)-one was used instead of 4-(5-((trimethylsilyl) ethynyl)pyrimidin-2-yl)aniline.

Preparation Example 1: Preparation of Tablets by Direct Pressing 5.0 mg of each of the active ingredients prepared in Examples 1 to 171 was sieved, mixed with 14.1 mg of lactose, 0.8 mg of crospovidone USNF, and 0.1 mg of magnesium stearate, and then pressed to be prepared into tablets.

Preparation Example 2: Preparation of Tablets by Wet Granulation 5.0 mg of each of the active ingredients prepared in Examples 1 to 171 was sieved, and then mixed with 16.0 mg of lactose and 4.0 mg of starch. 0.3 mg of polysorbate 80 was dissolved in pure water, and this solution was added to the mixture in a suitable amount, followed by atomizing to obtain fine particles. After drying, the fine particles were sieved, mixed with 2.7 mg of colloidal silicon dioxide and 2.0 mg of magnesium stearate, and pressed to prepare tablets.

Preparation Example 3: Preparation of Powder and Capsules 5.0 mg of each of the active ingredients prepared in Examples 1 to 171 was sieved and then mixed with 14.8 mg of lactose, 10.0 mg of polyvinylpyrrolidone, and 0.2 mg of magnesium stearate. The mixture was filled into hard No. 5 gelatin capsules using a suitable apparatus to prepare capsules.

Preparation Example 4: Preparation of Injection Drugs 100 mg of each of the active ingredients prepared in Examples 1 to 171 was mixed with 180 mg of mannitol, 26 mg of $Na_2HPO_4 \cdot 12H_2O$, and 2974 mg of distilled water to prepare injection drugs.

Experimental Example 1: Selection of Tau Protein Aggregation-Inhibiting Materials Using Cell Models In order to select new tau protein aggregation-inhibiting materials, tau-BiFC cell models, in which it is easy to observe the formation of tau oligomers in living cells, were used. Tau-BiFC cells were dispensed into 384-well plates, and the next day, the compounds prepared according to Examples 1 to 171 were treated at 1 μM, 3 μM, and 10 μM, respectively, together with Forskolin (treatment concentration 30 UM) which stimulates tau phosphorylation by activating PKA and induces tau protein aggregation. After 48 hours, intracellular nuclei were stained using Hoechst (treatment concentration 2 μg/mL), and BiFC fluorescence intensity was automatically quantified using Operetta (PerkinElmer) to count stained nuclei in each well from the total well plates. The group treated with only Forskolin, which induces tau protein agglutination, was set as a reference point in a 100% tau protein-aggregation state, and the effect thereof was confirmed by the equation "BiFC fluorescence intensity by the compound synthesized according to the embodiment of the present invention/(fluorescence intensity of control group treated with only Forskolin inducing tau protein aggregation-fluorescence intensity of untreated control group)×100". Further, the degree of cytotoxicity induced by the newly synthesized compound is also based on the 100% survival rate of the group treated with Forskolin alone, and the cytotoxicity value of the compound was calculated by the equation "number of stained nuclei in the group treated with the compound/number of stained nuclei in the group treated with Forskolin x 100". From the treatment results, materials that inhibit intracellular tau protein aggregation were selected from a series of candidate groups based on 70% or more of tau protein aggregation inhibition rate and 100% of cell survival rate at a compound treatment concentration of 10 UM or more.

Experimental Example 2: Confirmation of Concentration-Dependent Tau Protein Aggregation Inhibition Effects of New Compounds In order to evaluate dose-dependent tau protein aggregation inhibition effects of the compounds selected according to Experimental Example 1, the selected compounds were treated in tau-BiFC cells at concentrations of 0.03 UM, 0.01 μM, 0.3 μM, 1 μM, 3 μM, 10 μM, and 30 μM, respectively, together with Forskolin (treatment concentration 30 M) as a tau protein aggregation inducing material. After 48 hours, tau protein aggregation reaction and cytotoxicity degree were analyzed by observing cell images. The $IC_{50}$ and toxicity of the compounds were analyzed by nonlinear regression analysis of prism software (Graph Pad). The results calculated for the representative compounds are shown in Table 1 below.

TABLE 1

| | Tau BiFC in cells | | | Tau BiFC in cells | |
|---|---|---|---|---|---|
| Compounds # | $IC_{50}$ (μM) | Cell survival rate (% @ 10 μM) | Compounds # | $IC_{50}$ (μM) | Cell survival rate (% @ 10 μM) |
| 1 | 0.49 | 74 | 2 | 1.3 | 59 |
| 3 | 2.4 | 66 | 4 | 0.65 | 93.1 |
| 6 | 0.9 | 147.1 | 8 | 0.02 | 107.8 |
| 10 | 0.52 | 110.1 | 11 | 0.05 | 146.2 |
| 12 | 0.03 | 119.3 | 20 | 0.6 | 90 |
| 35 | 1.7 | 100 | 36 | 0.053 | 99.3 |
| 37 | 1.34 | 88.3 | 38 | 0.94 | 88.9 |
| 39 | 1.51 | 89.8 | 40 | 2.5 | 101.3 |

TABLE 1-continued

| | Tau BiFC in cells | | | Tau BiFC in cells | |
|---|---|---|---|---|---|
| Compounds # | $IC_{50}$ (μM) | Cell survival rate (% @ 10 μM) | Compounds # | $IC_{50}$ (μM) | Cell survival rate (% @ 10 μM) |
| 41 | 7 | 126.8 | 42 | 3 | 128 |
| 43 | 1.84 | 112.3 | 45 | 9.5 | 114.8 |
| 50 | 0.73 | 76 | 51 | 7.42 | 84.2 |
| 52 | 1.4 | 139.6 | 53 | 1.3 | 158.2 |
| 55 | 1 | 120.1 | 58 | 1.2 | 113.8 |
| 59 | 0.5 | 120.3 | 61 | 3.1 | 111.7 |
| 63 | 0.74 | 111.4 | 64 | 0.19 | 112.5 |
| 65 | 0.072 | 103.3 | 66 | 0.012 | 96.8 |
| 67 | 0.06 | 199.9 | 68 | 0.06 | 177.2 |
| 69 | 0.19 | 204.7 | 70 | 0.033 | 125.1 |
| 71 | 0.86 | 116.4 | 72 | 0.035 | 89.5 |
| 73 | 1.1 | 138.5 | 76 | 0.04 | 195.8 |
| 82 | 0.43 | 120.2 | 83 | 0.3 | 98 |
| 84 | 1.6 | 151.1 | 87 | 0.4 | 75.3 |
| 90 | 0.2 | 156.6 | 91 | 0.2 | 133.4 |
| 92 | 0.24 | 119.5 | 93 | 0.06 | 129.2 |
| 94 | 2.7 | 95.3 | 95 | 0.8 | 100.8 |
| 96 | 0.4 | 106.1 | 99 | 0.1 | 113.1 |
| 110 | 0.76 | 74.6 | 134 | 0.2 | 115.8 |
| 149 | 0.1 | 113.9 | 151 | 0.65 | 69.5 |

Experimental Example 3: Inhibition Effects of CYP Coenzyme Activity by Novel Compounds 5 The inhibition effects of CYP coenzyme activity by the compounds prepared according to Examples 1 to 171 was confirmed. Specifically, human liver microsomes (0.25 mg/mL), a 0.1 M phosphate buffer solution (pH 7.4), substrate drug cocktails (phenacetin 50 μM, diclofenac 10 μM, S-mephenytoin 100 μM, dextromethorphan 5 μM, and midazolam 2.5 μM) of five kinds of drug metabolism enzymes, and the compounds with a concentration of 0 μM or 10 PM were added, respectively. Then the mixture was cultured in advance at 37° C. for 5 minutes, and then further cultured at 37° C. for 15 minutes together with the addition of an NADPH generation system solution. Thereafter, a reaction was terminated by adding an acetonitrile solution containing an internal standard material (terfenadine), centrifugal separation (14,000 rpm, 4° C.) was performed for 5 minutes, and then a supernatant was injected into an LC-MS/MS system. Metabolites of the substrate drugs were simultaneously analyzed to evaluate the drug metabolism inhibition ability.

Metabolites of each CYP coenzyme indicator drug generated through the reaction were analyzed using the Shimadzu Nexera XR system and TSQ vantage (Thermo). Kinetex C18 (2.1 mm×100 mm, 2.6 μm, particle size; Phenomenex, USA) was used in an HPLC column, and (A) distilled water containing 0.1% formic acid and (B) acetonitrile containing 0.1% formic acid were used as mobile phases, and the gradient program shown in Table 2 was applied.

TABLE 2

| Time (minute) | Flow rate (mL/min) | % A | % B |
|---|---|---|---|
| 0 | 0.3 | 100 | 0 |
| 1.0 | 0.3 | 60 | 40 |
| 4.0 | 0.3 | 50 | 50 |
| 4.1 | 0.3 | 100 | 0 |
| 7.0 | 0.3 | 100 | 0 |

The generated metabolites were quantified using an MRM (multiple reaction monitoring) quantification mode, and Xcalibur (version 1.6.1) was used for data analysis. Table 3 shows the inhibition effects of CYP coenzyme activity of the novel compounds prepared according to the embodiments of the present invention.

TABLE 3

| Compounds # | CYP1A2 | CYP2C9 | CYP2C19 | CYP2D6 | CYP3A4 |
|---|---|---|---|---|---|
| 1 | 76.9 | 63.2 | 90.7 | 98.4 | 89.4 |
| 2 | 84.3 | 57.7 | 88.8 | 74.3 | >100 |
| 4 | 85.1 | 81.5 | 90.7 | 97.3 | >100 |
| 8 | 94.1 | 85.1 | >100 | >100 | >100 |
| 11 | 80.1 | 33.2 | 83.4 | 81.9 | 97.6 |
| 12 | 88.1 | 7.4 | 81.3 | 87.8 | 91.6 |
| 35 | 99.9 | 81.3 | >100 | >100 | >100 |
| 36 | 86 | 60.7 | >100 | 98.6 | >100 |
| 37 | 78.1 | 56.9 | 100 | >100 | >100 |
| 42 | 83.6 | 88.8 | 96.2 | >100 | >100 |
| 45 | 36.9 | >100 | >100 | >100 | >100 |
| 50 | 80.7 | 73 | 83.8 | >100 | 95 |
| 55 | 66.9 | 59.5 | 86 | >100 | 87.6 |
| 61 | 45.1 | 75.5 | 93.6 | >100 | 90.1 |
| 63 | 43.3 | 84.2 | >100 | >100 | >100 |
| 67 | 61.8 | 62.6 | 93.1 | >100 | 94.6 |
| 69 | 80.1 | 16.6 | 82.1 | >100 | 95.2 |
| 70 | 50.3 | 48.7 | >100 | >100 | 95.5 |
| 72 | 85.8 | 88.7 | 97.8 | 98.9 | >100 |
| 83 | 47.7 | 51 | 96.4 | 91.1 | 86.4 |
| 84 | 89.4 | 91.2 | 79.4 | 68.8 | 95.1 |
| 87 | 77 | 53.5 | 86.4 | 83.6 | 62.7 |
| 90 | 35.1 | 47.4 | 92.9 | >100 | 51.7 |
| 91 | 88.9 | 57 | 93.7 | >100 | 91.5 |
| 92 | 64.1 | 46.8 | 90.5 | 99.1 | 85.5 |
| 93 | 80.7 | 45.5 | 91.6 | 85.6 | 91.5 |
| 110 | 55 | 60.2 | 51.3 | 70.8 | 55 |
| 134 | >100 | >100 | >100 | >100 | >100 |
| 151 | 94.4 | 83.6 | 85.2 | 94.6 | 94.4 |

Experimental Example 4: Confirmation of Stability of Liver Microsomes of Novel Compounds The liver microsomal stability of the compounds prepared according to Examples 1 to 171 was confirmed. Specifically, four kinds of liver microsomes (human, dog, rat, and mouse, each 0.25 mg/mL), a 0.1 M phosphate buffer solution (pH 7.4), and the compounds with a concentration of 1 μM were added, respectively. Then the mixture was cultured in advance at 37° C. for 5 minutes, and then further cultured at 37° C. for 30 minutes together with the addition of an NADPH generation system solution. Thereafter, a reaction was terminated by adding an acetonitrile solution containing an internal standard material (chloropropamide), centrifugal separation (14,000 rpm, 4° C.) was performed for 5 minutes, and then a supernatant was injected into an LC-MS/MS system. The substrate drugs were analyzed to evaluate the metabolic stability for 8 kinds of compounds.

The amount of substrate remaining through the reaction was analyzed using the Shimadzu Nexera XR system and TSQ vantage (Thermo). Kinetex XB-C18 (2.1 mm×100 mm, 2.6 μm, particle size; Phenomenex, USA) was used in an HPLC column, and (A) distilled water containing 0.1% formic acid and (B) acetonitrile containing 0.1% formic acid were used as mobile phases. Analyst software (version 1.6.3) and Xcalibur (version 1.6.1) were used for data analysis. The calculated results are shown in Table 4 below.

TABLE 4

| Compounds # | Human (%) | Dog (%) | Rat (%) | Mouse (%) |
|---|---|---|---|---|
| 1 | 44.1 | 5.7 | 28.3 | 86.1 |
| 2 | 92.7 | 92.1 | 97.2 | 6.4 |

TABLE 4-continued

| Compounds # | Human (%) | Dog (%) | Rat (%) | Mouse (%) |
|---|---|---|---|---|
| 4 | 70.1 | 75 | 4.5 | 35.6 |
| 8 | 80.9 | 96 | 40.7 | 83.7 |
| 11 | 87.5 | 79.6 | 49.6 | 65.6 |
| 12 | 52.2 | 81.6 | 25.8 | 45.2 |
| 35 | 82.2 | 24.2 | 56.4 | 10.7 |
| 36 | 65.9 | 60.6 | 20.1 | 37.9 |
| 37 | 55.7 | 61 | 25.9 | 32.7 |
| 42 | 53.4 | 30.7 | 46.5 | 47.9 |
| 50 | 81.1 | 88.9 | 85.7 | 89.5 |
| 55 | 70 | 85.6 | 60.8 | 71.2 |
| 61 | 70.4 | 32.6 | 66.2 | 33.5 |
| 63 | 87.4 | 82.6 | 72.1 | 9.5 |
| 69 | 97.6 | 71.9 | 64.4 | 34.2 |
| 70 | | 64.2 | 98.3 | 55.8 |
| 72 | 86.3 | 84.8 | 72.8 | 58.6 |
| 83 | 64.1 | 31.9 | 62.2 | 11 |
| 87 | 82.1 | 80.6 | 73.9 | 83.1 |
| 92 | 74.6 | 74.7 | 72.7 | 51.9 |
| 93 | 83.9 | 60.4 | 63.3 | 37.3 |
| 110 | 55 | 60.2 | 51.3 | 70.8 |
| 134 | >100 | >100 | >100 | >100 |
| 151 | 94.4 | 83.6 | 85.2 | 94.6 |

Experimental Example 5: Study of Pharmacokinetics of Novel Compounds

Pharmacokinetics of the compounds prepared according to Examples 1 to 171 were studied using experimental animal models. Specifically, an SD rat of 7 to 8 weeks of age (Core Tech, Hana Trading Co., Ltd.) having a body weight of about 250 g to 300 g was purchased, and was managed in a simple breeding room for small animals set to a temperature of 22° C.±2° C., a relative humidity of 50%±5%, a lighting time of 12 hours (light up at 8:00 A.M., turn off at 8:00 P.M.), and an illuminance of 150 lux to 300 lux. During the entire test period, feed was freely provided, RO water was freely provided, and fasting was performed for 16 hours before the oral administration of a drug. After preparing a drug under the conditions shown in Table 5 below, the drug was intravenously injected (IV) or orally administered (PO). 500 UL of transfused blood was collected in a tube containing sodium heparin and centrifuged at 2° C. to 8° C. at 8,000 rpm for 6 minutes to obtain plasma from the blood. The obtained plasma was added to 180 μL of acetonitrile containing internal standard materials, vortexed, and then centrifuged at 15,000 rpm at 4° C. for 5 minutes to obtain a supernatant. The obtained supernatant was analyzed by LC-MS/MS. HPLC and MS conditions used for the analysis are shown in Tables 6 and 7 below.

TABLE 5

| Experimental group | Administration route | Formulation composition) | Dosage (mg/kg) | Dosage volume (μL) |
|---|---|---|---|---|
| 1 | IV | 10% NMP, 90% PEG 400 | 1 | 250 |
| 2 | PO | 10% NMP, 90% PEG 400 | 10 | 500 |

TABLE 6

| | |
|---|---|
| HPLC system | Nexera XR system (Shimadzu, Japan) |
| Column | Kinetex C18 column (2.1 mm × 100 mm, 2.6 μm, particle size; Phenomenex, USA) |

TABLE 6-continued

| | |
|---|---|
| Injection volume | 2 μL |
| Mobile phases | (A) 0.1% aqueous formic acid solution<br>(B) 0.1% formic acid acetonitrile solution |
| Sample analysis time | 3.5 minutes |
| Retention time | 2.2 minutes |

TABLE 7

| | |
|---|---|
| Analysis system | TSQ vantage triple quadruple (Thermo, USA) |
| Molecular weight | 262.28 g/mol |
| Ion source type & ionization mode | Turbo Spray Ionization, negative mode<br>MRM transition (m/z) 263.090 → 185.1<br>CE (V): 19, S-lens: 83 |
| Lower Limit of Quantification (LLOQ) | Plasma: 20 ng/mL<br>Brain: 2 ng/mL |
| Standard curve range | Plasma: 20 ng/mL to 5,000 ng/mL<br>Brain: 2 ng/mL to 1,000 ng/mL |

Specific PK parameters were acquired using the Phoenix WinNonlin version 6.4 program (Phersight, USA) and wore calculated with a non-compartmental analysis model. The results are summarized in Table 8 below.

TABLE 8

| | Plasma PK parameters | | | | | | | |
|---|---|---|---|---|---|---|---|---|
| Compounds | Administration route | Dosage (mg/kg) | $AUC_{all}$ (hr, ng/mL) | $T_{1/2}$ (hr) | $C_{max}$ (ng/mL) | $T_{max}$ (hr) | CL (mL/min/kg) | F (%) |
| 1 | IV | 1 | 7260.0 ± 580.1 | 1.1 ± 1.0 | — | — | 11.5 ± 0.9 | 32 |
| | PO | 10 | 4652.8 ± 1158.9 | 1.6 ± 1.6 | 1840.0 ± 609.4 | 1.7 ± 2.9 | — | |
| 2 | IV | 1 | 7335.6 ± 1794.1 | 1.2 ± 0.3 | 4279.3 ± 1390.3 | 5.5 ± 1.0 | 2.4 ± 0.7 | 27.1 |
| | PO | 10 | 19890.5 ± 6049.3 | | | | | |
| 11 | IV | 2 | 11800.37 | 1.05 | 10677.27 | 0.08 | 2.84 | 32.5 |
| | PO | 10 | 19169.2 | 2.96 | 6901.11 | 0.25 | — | |
| 50 | IV | 1 | 8149.7 ± 1421.0 | 1.9 ± 0.3 | — | — | 2.0 ± 0.3 | 8.3 |
| | PO | 10 | 6726.6 ± 2700.2 | — | 1325.2 ± 788.2 | 5.0 ± 2.0 | — | |
| 56 | IV | 2 | 17481.28 | 1.57 | 9136.46 | 0.12 | 1.85 | 89.2 |
| | PO | 10 | 77995.11 | 3.21 | 11442.53 | 1.5 | — | |
| 93 | IV | 1 | 6059.4 ± 548.0 | 1.7 ± 0.1 | — | — | 2.7 ± 0.3 | 22.9 |
| | PO | 10 | 13884.8 ± 3420.9 | — | 2572.4 ± 422.7 | 5.0 ± 1.2 | — | |

It will be appreciated by those skilled in the art that the present invention as described above may be implemented into other specific forms without departing from the technical spirit or essential characteristics thereof. Thus, it is to be appreciated that embodiments described above are intended to be illustrative in all aspects and not restrictive. The scope of the present invention is represented by the appended claims to be described below rather than the detailed description, and it is to be interpreted that the meaning and scope of the appended claims and all of the changes or modified forms derived from equivalents thereof come within the scope of the present invention.

The invention claimed is:

1. A compound represented by Formula 3 or a pharmaceutically acceptable salt thereof:

Formula 3

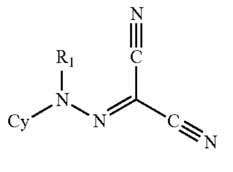

in Formula 3 above, $R_1$ is hydrogen;

Cy is unsubstituted benzothiazol-6-yl, unsubstituted benzothiazol-5-yl, unsubstituted quinolin-3-yl, indolyl, unsubstituted pyrrolopyridinyl, unsubstituted oxodihydrobenzothiazolyl, or unsubstituted oxodihydrobenzoxazolyl; or substituted benzothiazol-6-yl, substituted benzothiazol-5-yl, substituted indazolyl, substituted quinolin-3-yl, substituted indolyl, substituted pyrrolopyridinyl, substituted oxodihydrobenzothiazolyl, substituted oxodihydrobenzoxazolyl, or substituted oxodihydrobenzoimidazolyl; each of which is substituted with (i) methyl, ethyl, propyl, butyl, isopropyl, isobutyl, methoxy, ethoxy, fluoro, chloro, bromo, trifluoroethyl, difluoromethyl, trifluoromethoxy, dimethylcarbamoyl, phenoxy, isopropoxy, methylamino or dimethylamino, or (ii) phenyl, pyridinyl, furanyl, or thiophenyl unsubstituted or substituted with at least one selected from the group consisting of methyl, fluoro, and dimethylamino.

2. A compound is represented by Formula 4, or a pharmaceutically salt thereof:

Formula 4

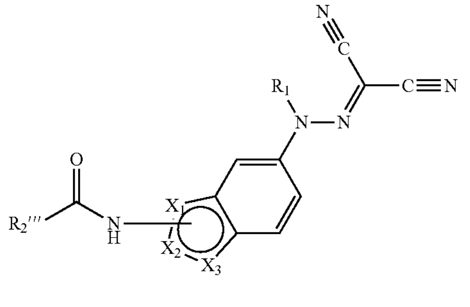

in Formula 4 above, $X_1$ to $X_3$ are different from each other, are each selected from C, N, O, and S, and are each connected to a carboxamido group through a C site;

$R_1$ is hydrogen or $C_{1-6}$ alkyl; and $R_2$" is $C_{1-6}$ alkyl, or aryl or heteroaryl unsubstituted or substituted with at least one selected from the group consisting of $C_{1-6}$ alkoxy, hydroxy, cyano, and $C_{1-6}$ alkyl.

3. The compound of claim 2 or pharmaceutically acceptable salt thereof, wherein $X_1$ to $X_3$ are sequentially N, C, and S or O, N, and C, and are connected to a carboxamido group through a C site;

$R_1$ is hydrogen; and $R_2$" is methyl, or phenyl, pyridinyl, pyrazinyl, or pyrimidinyl unsubstituted or substituted with at least one selected from the group consisting of methoxy, hydroxy, cyano, and methyl.

4. The compound of claim 1 or pharmaceutically acceptable salt thereof, benzo[d]thiazol-6-ylcarbonohydrazonoyl dicyanide,
benzo[d]thiazol-5-ylcarbonohydrazonoyl dicyanide,
(1-methyl-1H-indazol-6-yl)carbonohydrazonoyl dicyanide,
quinolin-3-ylcarbonohydrazonoyl dicyanide,
(2-methyl-2H-indazol-6-yl)carbonohydrazonoyl dicyanide,
(1-methyl-1H-indazol-5-yl)carbonohydrazonoyl dicyanide,
(1-methyl-1H-indol-5-yl)carbonohydrazonoyl dicyanide,
(1H-indol-5-yl)carbonohydrazonoyl dicyanide,
(1H-pyrrolo[2,3-b]pyridin-5-yl)carbonohydrazonoyl dicyanide,
(3-methyl-1H-indazol-6-yl)carbonohydrazonoyl dicyanide,
(3-methyl-1H-indazol-5-yl)carbonohydrazonoyl dicyanide,
(1H-indol-4-yl)carbonohydrazonoyl dicyanide,
(1-methyl-1H-pyrrolo[2,3-b]pyridin-5-yl)carbonohydrazonoyl dicyanide,
(1-propyl-1H-pyrrolo[2,3-b]pyridin-5-yl)carbonohydrazonoyl dicyanide,
(1-isopropyl-1H-pyrrolo[2,3-b]pyridin-5-yl)carbonohydrazonoyl dicyanide,
(1-ethyl-1H-pyrrolo[2,3-b]pyridin-5-yl)carbonohydrazonoyl dicyanide,
(1-(2,2,2-trifluoroethyl)-1H-pyrrolo[2,3-b]pyridin-5-yl) carbonohydrazonoyl dicyanide,
(2-methyl-1H-pyrrolo[2,3-b]pyridin-5-yl)carbonohydrazonoyl dicyanide,
(3-methyl-1H-pyrrolo[2,3-b]pyridin-5-yl)carbonohydrazonoyl dicyanide,
(3-chloro-1H-pyrrolo[2,3-b]pyridin-5-yl)carbonohydrazonoyl dicyanide,
(4-methoxy-1H-pyrrolo[2,3-b]pyridin-5-yl)carbonohydrazonoyl dicyanide,
(2-(dimethylcarbamoyl)-1H-pyrrolo[2,3-b]pyridin-5-yl) carbonohydrazonoyl dicyanide,
(2-phenylbenzo[d]thiazol-6-yl)carbonohydrazonoyl dicyanide,
(2-(4-fluorophenyl)benzo[d]thiazol-6-yl)carbonohydrazonoyl dicyanide,
(2-(4-(dimethylamino)phenyl)benzo[d]thiazol-6-yl)carbonohydrazonoyl dicyanide,
(2-(pyridin-3-yl)benzo[d]thiazol-6-yl)carbonohydrazonoyl dicyanide,
(2-(6-methylpyridin-3-yl)benzo[d]thiazol-6-yl)carbonohydrazonoyl dicyanide,
(2-(6-fluoropyridin-3-yl)benzo[d]thiazol-6-yl)carbonohydrazonoyl dicyanide,
(2-(furan-2-yl)benzo[d]thiazol-6-yl)carbonohydrazonoyl dicyanide,
(2-(thiophen-2-yl)benzo[d]thiazol-6-yl)carbonohydrazonoyl dicyanide,
(2-(5-fluoropyridin-3-yl)benzo[d]thiazol-6-yl)carbonohydrazonoyl dicyanide,
(2-(5-methylpyridin-3-yl)benzo[d]thiazol-6-yl)carbonohydrazonoyl dicyanide,
(2-(pyridin-3-yl)benzo[d]thiazol-5-yl)carbonohydrazonoyl dicyanide,
(2-(5-methylpyridin-3-yl)benzo[d]thiazol-5-yl)carbonohydrazonoyl dicyanide,
(2-oxo-2,3-dihydrobenzo[d]thiazol-6-yl)carbonohydrazonoyl dicyanide,
(3-methyl-2-oxo-2,3-dihydrobenzo[d]thiazol-6-yl)carbonohydrazonoyl dicyanide,
(2-methoxybenzo[d]thiazol-6-yl)carbonohydrazonoyl dicyanide,
(2-oxo-2,3-dihydrobenzo[d]oxazol-6-yl)carbonohydrazonoyl dicyanide,
(3-methyl-2-oxo-2,3-dihydrobenzo[d]oxazol-6-yl)carbonohydrazonoyl dicyanide,
(3-isopropyl-2-oxo-2,3-dihydrobenzo[d]thiazol-6-yl)carbohydrazonoyl dicyanide,
(3-(difluoromethyl)-2-oxo-2,3-dihydrobenzo[d]thiazol-6-yl)carbohydrazonoyl dicyanide,
(2-isopropoxybenzo[d]thiazol-6-yl)carbohydrazonoyl dicyanide,
(3-isopropyl-2-oxo-2,3-dihydrobenzo[d]oxazol-6-yl)carbohydrazonoyl dicyanide,
(3-(difluoromethyl)-2-oxo-2,3-dihydrobenzo[d]oxazol-6-yl)carbohydrazonoyl dicyanide,
(1,3-dimethyl-2-oxo-2,3-dihydro-1H-benzo[d]imidazol-5-yl)carbohydrazonoyl dicyanide,
(1,3-diisopropyl-2-oxo-2,3-dihydro-1H-benzo[d]imidazol-5-yl)carbohydrazonoyl dicyanide,
(1,3-bis(difluoromethyl)-2-oxo-2,3-dihydro-1H-benzo[d]imidazol-5-yl)carbohydraz onoyl dicyanide,
(2-(methylamino)benzo[d]thiazol-6-yl)carbohydrazonoyl dicyanide, or
(2-(dimethylamino)benzo[d]thiazol-6-yl)carbohydrazonoyl dicyanide.

5. A method of preparing the compound of claim 1, comprising the step of reacting sodium nitrite, a 5- to 14-membered heteroaryl or 5- to 14-membered heterocyclyl derivative containing an amine group, and malononitrile in the presence of acid to form an imine bond.

6. The method of claim 5, wherein, when the 5- to 14-membered heteroaryl or 5- to 14-membered heterocyclyl contains a nitrogen bondable thereto other than an amine group, it comprises a protecting group at the nitrogen site, and the method further comprises a step of removing the protection group after the step of forming the imine bond.

7. The method of claim 5, wherein the 5- to 14-membered heteroaryl or 5- to 14-membered heterocyclyl is prepared by reducing a nitrophenyl derivative containing a nitro group instead of an amine group in the same skeleton.

8. A method of preparing the compound of claim 2, comprising the steps of:

reacting carboxylic acid of $R_2$" or an anhydride thereof with

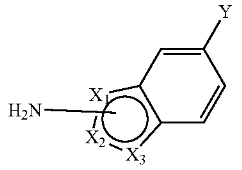

wherein Y is an unprotected or protected amine or nitro group to form an amide bond; and reacting sodium nitrite, a heterocycle derivative comprising $R_2$" connected to a carboxamido group obtained from the previous step, and malononitrile in the presence of acid to form an imine bond.

9. The method of claim 8, wherein, when Y is a protected amine group or nitro group, the method further comprises a step of converting the protected amine group or nitro group into an amine group before the step of forming the imine group.

10. A composition for inhibiting the aggregation of tau protein comprising the compound according to claim 1 as an active ingredient.

11. A composition for inhibiting the hyperphosphorylation of tau protein comprising the compound according to claim 1 as an active ingredient.

12. The compound of claim 2 or pharmaceutically acceptable salt thereof, wherein the compound is one of;

(2-(4-methoxyb27)benzo[d]thiazol-6-yl)carbonohydrazonoyl dicyanide, (2-(2-hydroxybenzamido)benzo[d]thiazol-6-yl)carbonohydrazonoyl dicyanide, (2-(3-cyanobenzamido)benzo[d]thiazol-6-yl)carbonohydrazonoyl dicyanide, (2-(5-methylnicotinamido)benzo[d]thiazol-6-yl)carbonohydrazonoyl dicyanide, (2-(3-hydroxypicolinamido)benzo[d]thiazol-6-yl)carbonohydrazonoyl dicyanide, (2-(pyrazine-2-carboxamido)benzo[d]thiazol-6-yl)carbonohydrazonoyl dicyanide, (2-(5-methylpyrazine-2-carboxamido)benzo[d]thiazol-6-yl)carbonohydrazonoyl dicyanide, (2-(pyrimidine-5-carboxamido)benzo[d]thiazol-6-yl)carbonohydrazonoyl dicyanide, (2-(2-methylpyrimidine-5-carboxamido)benzo[d]thiazol-6-yl)carbonohydrazonoyl dicyanide, (2-(4-methylpyrimidine-5-carboxamido)benzo[d]thiazol-6-yl)carbonohydrazonoyl dicyanide, (2-(3-methylpyrazine-2-carboxamido)benzo[d]thiazol-6-yl)carbonohydrazonoyl dicyanide, (2-(6-methylpyrazine-2-carboxamido)benzo[d]thiazol-6-yl)carbonohydrazonoyl dicyanide, (2-(pyrazine-2-carboxamido)benzo[d]thiazol-5-yl)carbonohydrazonoyl dicyanide, (2-(5-methylpyrazine-2-carboxamido)benzo[d]thiazol-5-yl)carbonohydrazonoyl dicyanide (3-(pyrazine-2-carboxamido)benzo[d]isoxazol-5-yl)carbonohydrazonoyl dicyanide, (3-(5-methylpyrazine-2-carboxamido)benzo[d]isooxazol-5-yl)carbonohydrazonoyl dicyanide, (3-(3-cyanobenzamido)benzo[d]isooxazol-5-yl)carbonohydrazonoyl dicyanide, or (3-(4-methoxybenzamido)benzo[d]isooxazol-5-yl)carbonohydrazonoyl dicyanide.

13. A composition for inhibiting the aggregation of tau protein comprising the compound according to claim 2 as an active ingredient.

14. A composition for inhibiting the hyperphosphorylation of tau protein comprising the compound according to claim 2 as an active ingredient.

* * * * *